(12) United States Patent
Hannaman et al.

(10) Patent No.: US 11,185,688 B2
(45) Date of Patent: Nov. 30, 2021

(54) METHOD AND APPARATUS FOR DELIVERY OF THERAPEUTIC AGENTS

(71) Applicant: ICHOR MEDICAL SYSTEMS, INC., San Diego, CA (US)

(72) Inventors: Andrew W. Hannaman, San Diego, CA (US); Robert M. Bernard, Las Vegas, NV (US); Stephen A. Morse, Woodinville, WA (US); Oliver Ruck, Lewisville, TX (US); Adam Hartman, Denton, TX (US); Thomas David Cox, Plano, TX (US)

(73) Assignee: Ichor Medical Systems, Inc., San Diego, CA (US)

( * ) Notice: Subject to any disclaimer, the term of this patent is extended or adjusted under 35 U.S.C. 154(b) by 57 days.

(21) Appl. No.: 16/144,794

(22) Filed: Sep. 27, 2018

(65) Prior Publication Data
US 2019/0030329 A1 Jan. 31, 2019

Related U.S. Application Data

(63) Continuation of application No. PCT/US2017/024631, filed on Mar. 28, 2017.
(Continued)

(51) Int. Cl.
*A61N 1/32* (2006.01)
*A61M 5/46* (2006.01)
(Continued)

(52) U.S. Cl.
CPC ............ *A61N 1/327* (2013.01); *A61K 31/711* (2013.01); *A61M 5/2033* (2013.01);
(Continued)

(58) Field of Classification Search
CPC ..... A61B 5/042; A61B 5/0422; A61B 5/0492; A61B 2018/0016; A61B 2018/00196;
(Continued)

(56) References Cited

U.S. PATENT DOCUMENTS 2,725,877 A 12/1955 Reiter et al.
2,860,439 A 11/1958 Johnson
(Continued)

FOREIGN PATENT DOCUMENTS

CN 1312728 A 9/2001
CN 1345607 A 4/2002
(Continued)

OTHER PUBLICATIONS

AU550342 Examination Report dated Mar. 5, 2009.
(Continued)

*Primary Examiner* — Kami A Bosworth
(74) *Attorney, Agent, or Firm* — Goodwin Procter LLP

(57) ABSTRACT

Methods and apparatus for the reproducible, consistent and efficacious delivery of a therapeutic agent to a subject. The present disclosure comprises apparatus for the controlled administration of the therapeutic agent through an orifice to the subject, a plurality of penetrating electrodes arranged with a predetermined spatial relationship relative to the orifice, and an electrical signal generator operatively connected to the electrodes.

12 Claims, 25 Drawing Sheets

Related U.S. Application Data

(60) Provisional application No. 62/314,286, filed on Mar. 28, 2016.

(51) Int. Cl.

| | |
|---|---|
| *A61M 5/315* | (2006.01) |
| *A61N 1/30* | (2006.01) |
| *A61K 31/711* | (2006.01) |
| *A61M 5/20* | (2006.01) |
| *A61M 5/32* | (2006.01) |
| *A61N 1/04* | (2006.01) |
| *A61N 1/05* | (2006.01) |
| *A61M 5/24* | (2006.01) |

(52) U.S. Cl.
CPC ...... *A61M 5/31568* (2013.01); *A61M 5/3202* (2013.01); *A61M 5/46* (2013.01); *A61N 1/0412* (2013.01); *A61N 1/306* (2013.01); *A61M 5/2448* (2013.01); *A61M 5/2455* (2013.01); *A61M 2005/206* (2013.01); *A61M 2005/208* (2013.01); *A61M 2005/2086* (2013.01); *A61M 2005/2481* (2013.01); *A61M 2005/31588* (2013.01); *A61M 2202/07* (2013.01); *A61M 2205/14* (2013.01); *A61M 2205/18* (2013.01); *A61M 2205/332* (2013.01); *A61M 2205/3306* (2013.01); *A61M 2205/3313* (2013.01); *A61M 2205/50* (2013.01); *A61M 2205/505* (2013.01); *A61M 2205/581* (2013.01); *A61M 2205/582* (2013.01); *A61M 2205/587* (2013.01); *A61M 2205/6009* (2013.01); *A61M 2205/8206* (2013.01); *A61M 2209/086* (2013.01); *A61N 1/0502* (2013.01); *A61N 1/325* (2013.01)

(58) Field of Classification Search
CPC .... A61M 5/20; A61M 5/2033; A61M 5/2448; A61M 5/2455; A61M 5/31568; A61M 5/3202; A61M 5/425; A61M 5/46; A61M 2005/206; A61M 2005/208; A61M 2005/2086; A61M 2005/2481; A61M 2005/31588; A61M 37/00; A61M 2037/0007; A61M 2205/13; A61M 2205/14; A61M 2205/18; A61M 2205/3306; A61M 2205/3313; A61M 2205/332; A61M 2205/50; A61M 2205/505; A61M 2205/581; A61M 2205/582; A61M 2205/587; A61M 2205/6009; A61M 2205/8206; A61M 2209/086; A61M 5/24; A61M 5/2422; A61M 5/2429; A61M 2005/2073; A61M 2005/2403; A61M 2005/2407; A61M 2005/2414; A61M 2005/1433; A61M 2005/1437; A61M 2005/244; A61M 2205/27; A61N 1/0412; A61N 1/0428; A61N 1/0448; A61N 1/0502; A61N 1/08; A61N 1/30; A61N 1/303; A61N 1/306; A61N 1/325; A61N 1/327

See application file for complete search history.

(56) References Cited

U.S. PATENT DOCUMENTS

| | | | |
|---|---|---|---|
| 4,108,177 A | 8/1978 | Pistor | |
| 4,198,975 A | 4/1980 | Haller | |
| 4,394,863 A | 7/1983 | Bartner | |
| 4,636,197 A | 1/1987 | Chu | |
| 4,832,682 A | 5/1989 | Sarnoff | |
| 5,141,496 A | 8/1992 | Dalto et al. | |
| 5,215,089 A | 6/1993 | Baker, Jr. | |
| 5,273,525 A | 12/1993 | Hofmann | |
| 5,306,236 A | 4/1994 | Blumenfeld et al. | |
| 5,318,514 A | 6/1994 | Hofmann | |
| 5,328,442 A | 7/1994 | Levine | |
| 5,383,851 A | 1/1995 | Mckinnon, Jr. et al. | |
| 5,478,316 A | 12/1995 | Bitdinger et al. | |
| 5,593,429 A | 1/1997 | Ruff | |
| 5,688,233 A | 11/1997 | Hofmann et al. | |
| 5,702,359 A | 12/1997 | Hofmann et al. | |
| 5,846,225 A | 12/1998 | Rosengart | |
| 5,851,197 A | 12/1998 | Marano et al. | |
| 5,873,549 A | 2/1999 | Lane et al. | |
| 5,873,849 A | 2/1999 | Bernard | |
| 5,968,006 A | 10/1999 | Hofmann | |
| 6,041,252 A | 3/2000 | Walker et al. | |
| 6,055,453 A | 4/2000 | Hofmann et al. | |
| 6,077,247 A | 6/2000 | Marshall et al. | |
| 6,110,161 A | 8/2000 | Mathiesen et al. | |
| 6,120,493 A | 9/2000 | Hofmann | |
| 6,159,181 A | 12/2000 | Crossman et al. | |
| 6,165,720 A | 12/2000 | Felgner et al. | |
| 6,199,766 B1 | 3/2001 | Fox et al. | |
| 6,208,893 B1 | 3/2001 | Hofmann | |
| 6,241,701 B1 | 6/2001 | Hofmann | |
| 6,254,573 B1 | 7/2001 | Haim et al. | |
| 6,278,895 B1 | 8/2001 | Bernard | |
| 6,356,783 B1 | 3/2002 | Hubbard, Jr. | |
| 6,516,223 B2 | 2/2003 | Hofmann | |
| 6,520,950 B1 | 2/2003 | Hofmann et al. | |
| 6,558,351 B1 | 5/2003 | Steil et al. | |
| 6,654,636 B1 | 11/2003 | Dev et al. | |
| 6,678,558 B1 | 1/2004 | Dimmer et al. | |
| 6,748,266 B2 | 6/2004 | Bernabei | |
| 6,899,699 B2 | 5/2005 | Enggaard | |
| 6,912,417 B1 | 6/2005 | Bernard et al. | |
| 6,915,159 B1 | 7/2005 | Kuribayashi et al. | |
| 6,918,901 B1 | 7/2005 | Theeuwes et al. | |
| 8,108,040 B2 | 1/2012 | Bernard et al. | |
| 8,187,249 B2 | 5/2012 | Bernard et al. | |
| 8,545,440 B2 | 10/2013 | Patrick et al. | |
| 9,364,664 B2 | 6/2016 | Masterson et al. | |
| 9,526,836 B2 | 12/2016 | Bernard et al. | |
| 9,802,035 B2 | 10/2017 | Masterson | |
| 2002/0078161 A1 | 6/2002 | Cheng | |
| 2002/0123675 A1 | 9/2002 | Trautman et al. | |
| 2003/0083641 A1 | 5/2003 | Angel et al. | |
| 2003/0083645 A1 | 5/2003 | Angel et al. | |
| 2003/0187395 A1 | 10/2003 | Gabel et al. | |
| 2005/0154434 A1 | 7/2005 | Simon et al. | |
| 2005/0215941 A1 | 9/2005 | Bernard et al. | |
| 2007/0005017 A1* | 1/2007 | Alchas | A61M 5/425 604/117 |
| 2007/0021712 A1 | 1/2007 | Bernard et al. | |
| 2008/0058706 A1 | 3/2008 | Zhang et al. | |
| 2008/0262414 A1 | 10/2008 | Barsness et al. | |
| 2010/0152644 A1 | 6/2010 | Pesach et al. | |
| 2011/0288467 A1 | 11/2011 | Bernard et al. | |
| 2012/0078161 A1 | 3/2012 | Masterson et al. | |
| 2013/0023749 A1* | 1/2013 | Afanasewicz | A61B 5/6885 600/386 |
| 2017/0050015 A1 | 2/2017 | Masterson et al. | |
| 2017/0252515 A1 | 9/2017 | Bernard | |
| 2017/0340880 A1* | 11/2017 | Lee | A61M 37/00 |
| 2018/0272120 A1 | 9/2018 | Masterson et al. | |

FOREIGN PATENT DOCUMENTS

| | | |
|---|---|---|
| CN | 1997423 B | 10/2012 |
| EP | 1462134 A1 | 9/2004 |
| EP | 2929909 A1 | 10/2015 |
| IL | 177942 A | 11/2011 |
| IL | 203766 A | 4/2012 |
| IN | 260268 | 4/2014 |
| JP | S61502865 A | 12/1986 |
| JP | H04244172 A | 9/1992 |
| JP | H11276583 A | 10/1999 |
| JP | 2000316991 A | 11/2000 |

(56) References Cited

FOREIGN PATENT DOCUMENTS

| | | |
|---|---|---|
| JP | 2002507459 A | 3/2002 |
| JP | 2002511761 A | 4/2002 |
| JP | 2004041434 A | 2/2004 |
| JP | 2007527779 A | 10/2007 |
| JP | 2008535637 A | 9/2008 |
| JP | 4362767 B2 | 11/2009 |
| JP | 5221127 B2 | 6/2013 |
| JP | 5410847 B2 | 2/2014 |
| JP | 2014532524 A | 12/2014 |
| KR | 101261642 | 4/2013 |
| NZ | 550342 A | 6/2010 |
| NZ | 585119 A | 8/2011 |
| WO | WO-8601120 A1 | 2/1986 |
| WO | WO-9504562 A1 | 2/1995 |
| WO | WO-9618425 A1 | 6/1996 |
| WO | WO-9843702 A2 | 10/1998 |
| WO | WO-9948546 A1 | 9/1999 |
| WO | WO-0007453 A1 | 2/2000 |
| WO | WO-0009184 A1 | 2/2000 |
| WO | WO-0009186 A2 | 2/2000 |
| WO | WO-0113975 A2 | 3/2001 |
| WO | WO-0113977 A1 | 3/2001 |
| WO | WO-0152731 A1 | 7/2001 |
| WO | WO-0202165 A2 | 1/2002 |
| WO | WO-03043525 A2 | 5/2003 |
| WO | WO-03086534 A1 | 10/2003 |
| WO | WO-2004004825 A2 | 1/2004 |
| WO | WO-2004014468 A1 | 2/2004 |
| WO | WO-2005087311 A1 | 9/2005 |
| WO | WO-2008086534 A1 | 7/2008 |
| WO | WO-2010069573 A2 | 6/2010 |
| WO | WO-2010073452 A1 | 7/2010 |

OTHER PUBLICATIONS

CA2559083 Office action dated Dec. 17, 2012.
CN200580014553.1 First Office Action dated Mar. 7, 2010.
CN200580014553.1 Second Office Action dated Aug. 16, 2010.
CN201210297392.3 second office action dated Jul. 8, 2014.
Davis et al. The mechanics of microneedles. Second Joint EMBS-BMES Conference 2002. Conference Proceedings, 24th Annual International Conference of the Engineering in Medicine and Biology Society, Annual Fall Meeting of the Biomedical Engineering Society, Houston, TX, Oct. 2002, 1:498-499.
EP05725237.1 Office action dated Dec. 18, 2012.
EP05725237.1 Search Report dated Mar. 11, 2011.
EP15165174.2 Extended European Search Report dated Aug. 6, 2015.
European Patent Applicaiton No. 15165174.2 Communication dated Mar. 31, 2017.
IN2835/KOLNP/2006 Examination Report dated Jun. 11, 2013.
IN2835/KOLNP/2006 Examination Report dated Mar. 8, 2011.
India Patent Application No. 3520/KOLNP/2011 First Examination Report dated Feb. 15, 2018.
International Patent Application No. PCT/US2017/024631 International Preliminary Report on Patentability dated Oct. 2, 2018.
International Patent Application No. PCT/US2017/024631 International Search Report and Written Opinion dated Jun. 19, 2017.
JP2007-503001 Office Action dated Feb. 1, 2011.
JP2012-066396 Office action dated Jun. 18, 2013.
JP2013-009962 Office action dated Sep. 24, 2014.
KR10-20067020757 Office Action dated Dec. 23, 2011.
KR10-2006-7020757 Office action dated Jul. 30, 2012.
NZ594442 Examination Report dated Aug. 12, 2011.
NZ594442 Further Exam Report dated Jan. 11, 2013.
PCT/US03/10337 International Search Report dated Sep. 4, 2003.
PCT/US05/07936 International Search Report dated Aug. 19, 2005.
Poland et al. "Determination of Deltoid Fat Pad Thickness: Implications for Needle Length in Adult Immunization." JAMA 1997 277(21):1709-1711.
Schneider, et al. Penetration Characteristics of Hypodermic Needles in Potential Skin Stimulants: Series 1. Technical Report No. UM-HSRI-78-29, Highway Safety Research Institue, Jul. 1978, p. 1-144.
SG200706583-2 Written Opinion dated Mar. 2, 2010.
SG201100352-2 Written Opinion dated Jun. 27, 2012.
U.S. Appl. No. 10/117,457 Final Office action dated Oct. 20, 2004.
U.S. Appl. No. 10/117,457 Office action dated Apr. 15, 2004.
U.S. Appl. No. 10/117,457 Office action dated Dec. 23, 2003.
U.S. Appl. No. 10/510,399 Final Office action dated Feb. 17, 2011.
U.S. Appl. No. 10/510,399 Office action dated Jun. 28, 2007.
U.S. Appl. No. 10/510,399 Office action dated Jul. 22, 2010.
U.S. Appl. No. 10/591,806 Final Office action dated Oct. 23, 2014.
"U.S. Appl. No. 10/591,806 Office Action dated Jun. 9, 2015".
U.S. Appl. No. 10/773,564, application filed Feb. 5, 2004.
U.S. Appl. No. 11/376,619 Final Office action dated Mar. 8, 2011.
U.S. Appl. No. 11/376,619 Office action dated Aug. 26, 2010.
U.S. Appl. No. 11/376,619 Office action dated Sep. 12, 2011.
U.S. Appl. No. 13/114,878 Final Office action dated Oct. 6, 2016.
U.S. Appl. No. 13/114,878 Offic action dated Jul. 6, 2015.
U.S. Appl. No. 13/114,878 Office Action dated Mar. 24, 2016.
U.S. Appl. No. 13/114,878 Office action dated Oct. 24, 2014.
U.S. Appl. No. 13/114,878 Office Action dated Oct. 6, 2016.
U.S. Appl. No. 13/450,320 Office action dated Aug. 22, 2014.
U.S. Appl. No. 13/450,320 Office Action dated Dec. 9, 2015.
"U.S. Appl. No. 13/450,320 Office Action dated Jul. 22, 2015".
U.S. Appl. No. 15/153,558 Office action dated Jan. 17, 2017.
U.S. Appl. No. 15/351,262 Office Action dated Jun. 22, 2018.
European Patent Application No. 17776508.8 Extended Search Report dated May 20, 2020.
European Patent Application No. 18188950.2 European Search Report dated Mar. 7, 2019.
Indian Patent Application No. 3520/KOLNP/2011 Official Communication dated Jun. 17, 2019.
Singapore Patent Application No. 11201808236Y Search Report and Written Opinion dated Jan. 28, 2020.
U.S. Appl. No. 10/591,806 Final Office action dated Jan. 31, 2014.
U.S. Appl. No. 10/591,806 Final Office action dated Jun. 19, 2013.
U.S. Appl. No. 10/591,806 Office action dated Oct. 11, 2012.
U.S. Appl. No. 11/981,516, application filed Oct. 31, 2007.
U.S. Appl. No. 11/981,517, application filed Oct. 31, 2007.
U.S. Appl. No. 11/981,547, application filed Jan. 31, 2007.
U.S. Appl. No. 11/981,702, application filed Oct. 31, 2007.
U.S. Appl. No. 13/114,878 Final Office action dated Mar. 31, 2014.
U.S. Appl. No. 13/114,878 Final Office action dated Sep. 10, 2013.
U.S. Appl. No. 13/114,878 Office action dated Dec. 20, 2012.
U.S. Appl. No. 13/450,320 Office action dated Mar. 12, 2013.
U.S. Appl. No. 13/450,320 Final Office action dated Aug. 9, 2013.
U.S. Appl. No. 13/450,320 Final Office action dated Feb. 4, 2014.
U.S. Appl. No. 15/719,266 Office Action dated Oct. 10, 2018.
Chilean Patent Application No. 201802720 Search Report and Office Action dated Jan. 22, 2020.
Chilean Patent Application No. 201802720 Search Report and Office Action dated Oct. 20, 2020.
Colombian Patent Application No. NC2018/0010352 Office Action dated Jan. 22, 2020.
Eurasian Patent Application No. 201892146 Office Action dated Sep. 24, 2020.
JP2018-549291 Office Action dated Feb. 3, 2021.
U.S. Appl. No. 16/279,687 Office Action dated Dec. 3, 2020.

* cited by examiner

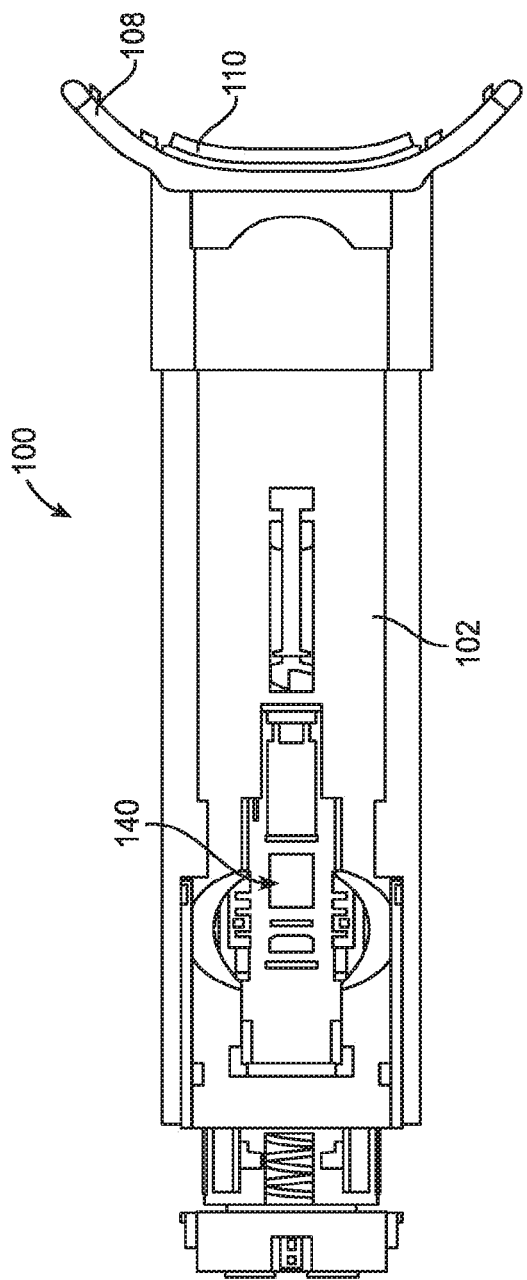
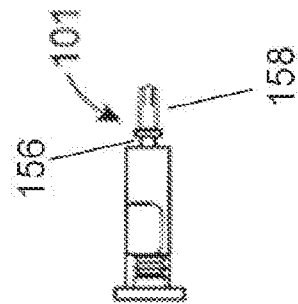
FIG. 3A
FIG. 3B

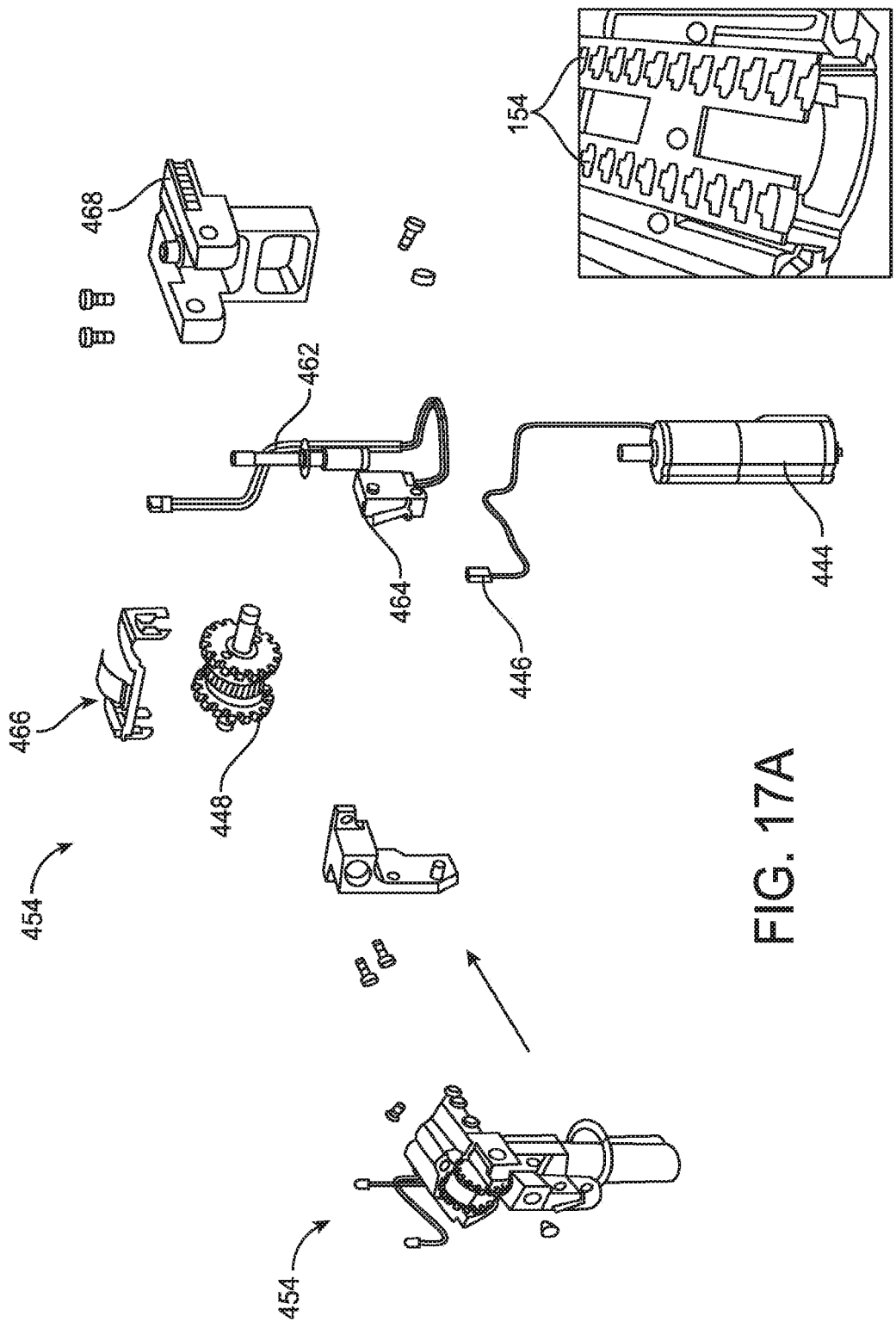

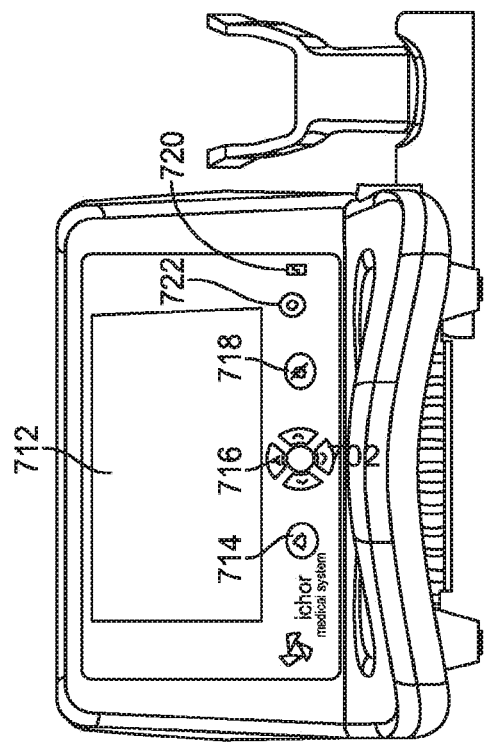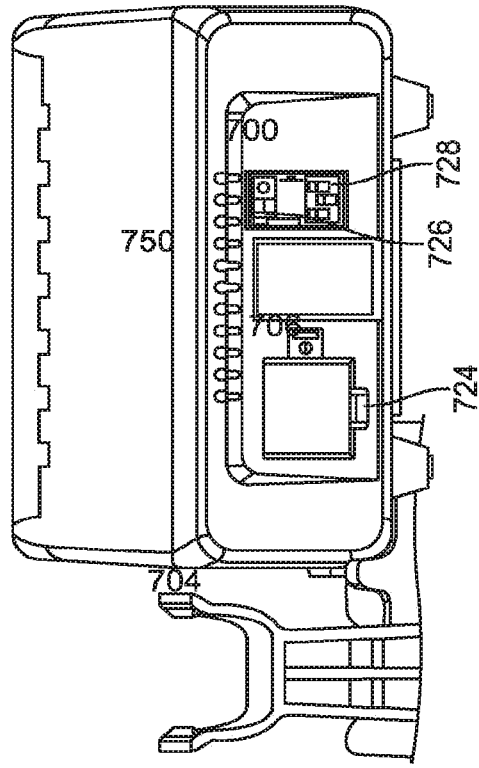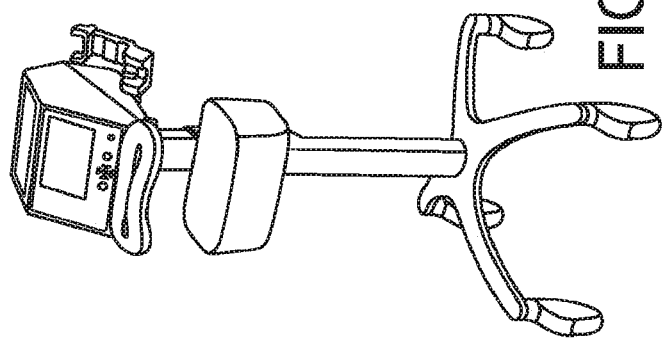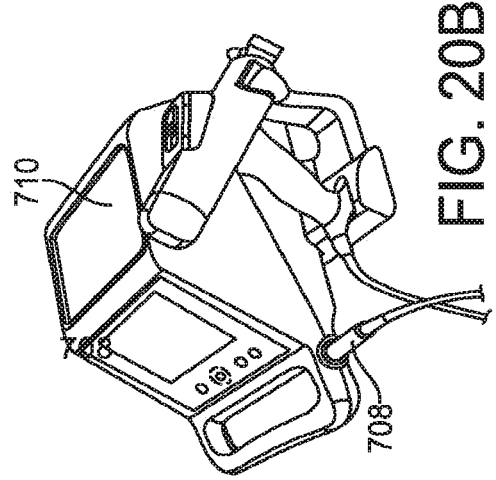
FIG. 20A
FIG. 20B
FIG. 20C
FIG. 20D

METHOD AND APPARATUS FOR DELIVERY OF THERAPEUTIC AGENTS

CROSS-REFERENCE TO RELATED APPLICATION

The present application is a continuation of International Application No. PCT/US2017/024631, filed on Mar. 28, 2017, entitled "METHOD AND APPARATUS FOR DELIVERY OF THERAPEUTIC AGENTS", which claims the benefit of U.S. Provisional Patent Application No. 62/314,286, filed Mar. 28, 2016, each of which are hereby incorporated by reference in their entirety.

FIELD

The present disclosure is directed to the administration of prophylactic and therapeutic agents to patients and, more particularly, to the reproducible, consistent, and efficacious delivery of prophylactic and therapeutic agents, such as nucleic acids, drugs, peptides, and proteins or combinations thereof, to defined regions in selected tissues of interest, facilitated by the local application of electrical fields, in a safe, effective, and consistent fashion across heterogeneous recipient populations with minimal user training.

BACKGROUND

Prophylactic and therapeutic agents have long been delivered to patients using various conventional routes of administration, such as topical, oral, intravenous, parenteral, and the like. Once administered to the patient by the selected route, the delivery of the agent to the tissue of interest and its beneficial interaction with the tissue is largely dependent on its inherent physicochemical factors, but may be facilitated by, for example, selected components of the delivery composition such as carriers, adjuvants, buffers and excipients, and the like.

The local application of electrical signals has been shown to enhance the distribution and uptake of macromolecules in living tissue. Application of such electrical signals in tissue in association with the administration of a prophylactic or therapeutic agent can have desirable effects on the tissue and/or the agent to be delivered. Specifically, techniques such as electroporation and iontophoresis have been utilized to significantly improve the distribution and/or uptake of a variety of agents in tissue. Such agents include pharmaceuticals, proteins, peptides, and nucleic acids, including both DNA and RNA sequences. Potential clinical applications of such techniques include the delivery of chemotherapeutic drugs in tumors, the delivery of nucleic acid sequences for prophylactic and therapeutic immunization, and the delivery of nucleic acid sequences encoding therapeutic proteins or peptides.

Many devices have been described for the application of electrical signals in tissue for the purpose of enhancing agent delivery. The majority of these have focused on a means for effective application of the electrical signals within a target region of tissue. A variety of surface and penetrating electrode systems have been developed for generating the desired electrophysiological effects.

These procedures comprise the administration of an agent of interest to a target tissue site in conjunction with the application of electrical fields of sufficient magnitude and duration to induce the desired effects on the delivery, distribution, and/or potency of the agent. The electrical fields are propagated via two or more electrodes in electrically conductive communication with the tissue. Electrode configurations suitable for use with these techniques include tissue penetrating electrodes, surface contact electrodes, and air gap electrodes. Specific electrode configurations include, but are not limited to, elongate needle or rod electrodes, point electrodes, meander electrodes (i.e., shaped wire), planar electrodes, and combinations thereof. The specific type and arrangement of electrodes is selected based on the target tissue type and the objectives of the procedure.

An important consideration for the use of with these techniques is that enhancement of agent activity is contingent on achieving spatial and temporal co-localization of the agent of interest with the electrical field. Specifically, the desired outcome is best achieved when the electrical fields are propagated within the target tissue in the presence of the agent of interest.

A broad range of methods and devices have been described for the application of electrical fields in tissue in the presence of an agent of interest for the purpose of enhancing agent delivery in skin and muscle tissue. The devices include the use of both surface and tissue penetrating electrode systems as well as combinations thereof. In spite of the promise associated with electrically mediated agent delivery and the potential clinical applications of these techniques, progress has been hampered by the lack of an effective means to achieve the overall objective of efficient and reliable agent delivery using these techniques. One of the most significant shortcomings of current systems is the inability to achieve reliable and consistent application from subject to subject. Significant sources of this variability are due to differences in the technique and skill level of the operator. Other sources of variability that are not addressed by current systems include differences in the physiologic characteristics between patients that can affect the application of the procedure. Other considerations for the development of suitable devices include their ease of use and the implementation of designs that reduce the frequency and significance of potential user errors.

Given that safe, reliable, accurate, and consistent application of clinical therapies is highly desirable, the development of improved application systems is well warranted. Such development should include a means for minimizing operator-associated variability while providing a means to accommodate the differences in patient characteristics likely to be encountered during widespread clinical application of electrically mediated agent delivery. In other words, specific areas for refinement include the ability to maintain consistent performance across heterogeneous recipient populations and a reduction in the level of training and skill required for effective use by the user. In addition, the device should be designed to facilitate avoidance of user or device errors and minimize their impact when they occur.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY OF THE DISCLOSURE

The present disclosure provides methods and apparatus for the reproducible, consistent, and efficacious delivery of therapeutic agents, such as nucleic acids, pharmaceutical drugs, peptides, and proteins or combinations thereof, to patients or subjects utilizing Electrically Mediated Therapeutic Agent Delivery (EMTAD). As used herein, a patient is alterntaively called a subject, and vice-versa. Use of the term "patient" does not require that the subject be under a doctor's care, althouth they may be.

In one aspect, provided is an apparatus for the delivery of a therapeutic agent to a predetermined site within a patient or subject comprising an assembly for controlled administration of the therapeutic agent to the subject comprising a reservoir for the therapeutic agent, at least one orifice through which the agent is administered, and a controlled source of energy sufficient to transfer a predetermined amount of the therapeutic agent at a predetermined rate from the reservoir through the orifice to the predetermined site within the subject. In addition, the apparatus can comprise a plurality of penetrating electrodes arranged with a predetermined spatial relationship relative to the orifice, and means for generating an electrical signal operatively connected to the electrodes.

Other aspects of the present disclosure include methods comprising Therapeutic Agent Administration (TEA) in controlled spatial and temporal relation with Electric Signal Administration (ESA).

Benefits and advantages to certain implementations according to present principles are manifold. Some implementations allow the selection of depth of needle and electrode insertion, allowing insertion into various types of desired tissue, (e.g., dermis, muscle, etc.) across heterogeneous populations of varying body mass and body composition. These implementations also facilitate adaptation of the methods for use in specific target populations, for instance, but not restricted to, men for cancer therapeutic agents such as prostate cancer therapeutic agents, individuals for vaccination and/or treatment such as pregnant women for Zika virus vaccination or treatment, small children for pediatric vaccines including cancer vaccines, and so on. Provided herein are systems and methods comprising design features render the systems and methods resistant to accidental discharge or potential misuse, e.g., due to dropping, jarring, and/or falling. In some embodiments are provided devices configured for multiple injection depths. Systems and methods according to present principles allow numerous safety interlocks to reduce the frequency and/or impact of user errors. These include features to facilitate proper preparation and configuration of the dose to be administered, ensuring that the device is applied with requisite force to the tissue of the recipient, ensuring that a safety cap has been removed, and so on. Systems, apparatus and methods according to present principles can allow for a highly consistent therapy to be delivered irrespective of administrator or the type of recipient. Systems, apparatus and methods described herein can allow for, e.g., a consistent force profile to be obtained prior to and during delivery of the therapy, so that recipients with varying skin and muscular characteristics can be dosed consistently.

Provided herein is an apparatus for the controlled delivery of a therapeutic agent to a predetermined tissue site within a subject comprising: a cartridge assembly comprising an outer cartridge, an inner cartridge, a needle hub, a vessel configured to contain the therapeutic agent, wherein the outer cartridge provides a vessel receiver configured to receive the vessel; an applicator comprising a cartridge assembly receiver configured to receive the cartridge assembly or a portion thereof, and an insertion detector, wherein the insertion detector is configured to sense loading of the vessel in the vessel receiver; a vessel interlock, wherein the vessel interlock is configured to lock out the apparatus from actuation until the vessel is loaded properly in the vessel receiver; at least one injection orifice in fluid communication with the therapeutic agent when the agent is loaded in the vessel and through which the therapeutic agent is administered; a plurality of penetrating electrodes arranged with a predetermined spatial relationship relative to the orifice; an electrical field generator configured to generate an electrical signal operatively connected to the electrodes; and a controlled source of energy sufficient to transfer a predetermined amount of the therapeutic agent at a predetermined rate from the vessel through the orifice to the predetermined site within the subject.

In some embodiments, the apparatus further comprises a needle. In some emdociments, the electrodes are a plurality of elongate electrodes. In another embodiment, the vessel interlock is configured to prevent inadvertent actuation of cartridge function. The vessel interlock may comprise a mechanical interlock. In some embodiments, the apparatus comprises a second interlock comprising a light emitter/collector, a cartridge breech, a force interlock, an alignment guide and a splay shield, a trigger lock, a safety switch, an exterior cartridge cap or a combination thereof. In certain embodiments, the mechanical interlock comprises tabs that are moved from a first position to a second position by the vessel when the vessel is properly loaded, whereby when the tabs are in the second position, the device may be actuated. In another embodiment, the vessel interlock further comprises at least one vessel lockout hole. In yet another embodiment, the cartridge breech provides an optical line of sight through a vessel lockout hole. It yet another embodiment, the a vessel detection cap may engage the cartridge breech through a vessel detection spring. In some embodiments, the vessel detection spring is configured to push the reservoir into engagement with the needle hub. In some embodiments, the vessel interlock further comprises a tab extending from a cartridge surface, and wherein the tab is configured to interact with a corresponding detent feature located in the applicator such that loading of the cartridge into the applicator is physically blocked unless the tab is deflected by a properly loaded vessel.

In some embodiments, the first interlock comprises a splay shield, wherein said exterior cartridge cap comprises an inner surface proximal to said splay shield, and wherein said inner surface further comprises at least one hook capable of engaging a corresponding wall defined on said splay shield. In certain instances, the apparatus further comprise a third interlock. In another instance, the third interlock is a force interlock. In yet another instance, the force interlock senses a force applied against the predetermined tissue site of the subject and prevents administration of the therapeutic agent to the subject when insufficient force is applied. In some embodiments, the force interlock further forms an electrical lock within the applicator. The force interlock may further comprise at least one cartridge force sensor contact.

In some instances, the apparatus provided herein further comprises a key to the vessel, wherein the key is configured to slides over a barrel of the vessel to ensure appropriate mating within the cartridge assembly. In certain instances, the first interlock comprises a splay shield that comprises a rib and an edge configured to engage with the predetermined tissue site of the subject and configured to place the apparatus into tension perpendicular to the direction of the needle deployment for administration of the therapeutic agent. The first interlock of the apparatus provided herein may comprise a splay shield which comprises a force contact pick up. The force contact pick up may comprise at least one first pad, at least one second pad, and a flexible circuit. In some embodiments, the first interlock further comprises a splay shield, and said splay shield is mechanically biased by at least one force contact spring.

The cartridge assembly of the apparatus as provided herein may further comprise a stick shield. In some embodiments, the stick shield further comprises a stick shield nub, a stick shield hole, and a stick shield spring. In some embodiments, the first interlock comprises the splay shield that comprises at least one hole for slidable movement of the stick shield. In certain embodiments, the apparatus provided herein further comprises at least one stick shield support to interface with the outer cartridge. In an exemplary embodiment, the stick shield support is a stamped metal support arm. In another exemplary embodiment, the stick shield supports moves over at least one retaining wall in a sequential order. In some embodiments, the apparatus provided herein comprises a first retaining wall which can prevent proximal movement of the stick shield in case of discharge of said apparatus at a first selected depth and a second retaining wall which can prevent proximal movement of the stick shield after discharge of said apparatus at a second selected depth in a subject. In some embodiments, the stick shield support is integrated as an injection molded plastic feature of an outer cartridge cap.

In another embodiment, the stick shield support abuts the stick shield and prevents the stick shield from moving in the proximal direction in a ratcheting fashion. In yet another embodiment, the apparatus as provided herein further comprises a gear rack implemented on the stick shield to reduce proximal movement. In certain cases, the stick shield support prevents the stick shield from moving in the proximal direction when at least 5 N of force is applied. In another case, the stick shield support prevents the stick shield from moving in the proximal direction when at least 15 N of force is applied. In some cases, the stick shield support is integrated as an injection molded plastic feature of the alignment guide and splay shield. In some embodiments, wherein upon loading of the cartridge assembly into the applicator, the vessel moves forward to mate with the needle hub and contacts the cartridge to the needle at the time of administration of the therapeutic agent. In another embodiment, the inner cartridge moves in a slidable manner in relationship to the outer cartridge along a common longitudinal axis. In some instances, the inner cartridge engages with an inner cartridge cap at a distal end, wherein the inner cartridge cap locks the electrodes in place and provides a bearing surface for the stick shield.

The apparatus as provided here in may further comprises a sensor. In some embodiments, the sensor is selected from the group consisting of a cartridge loading sensor, a cartridge loaded sensor, a cartridge force sensor, an insertion mechanism position sensor, the insertion detector, an optical detector, and an electrical sensor. In some embodiments, a loading drive subassembly comprises a cartridge loading sensor and a cartridge loaded sensor. In some embodiments, the loading drive subassembly further comprises at least one cartridge guide rail and a loading motor. In some embodiments, the loading drive subassembly further comprises a connection to a pinion gear assembly pulling the cartridge assembly into the cartridge assembly receiver via a rack on a base of the outer cartridge. In some embodiments, the pinion gear assembly engages the rack on the outer cartridge. In some embodiments, the rack comprises at least a first rack tooth. In some embodiments, the first rack tooth provides a tactile sensation when the cartridge assembly is inserted into the cartridge assembly receiving volume. In some embodiments, the first rack tooth provides torsional stability. In some embodiments, the cartridge loading sensor detects an initiating flag on the cartridge assembly to initiate loading. In some embodiments, the cartridge loaded sensor detects an initiating flag on the cartridge assembly to cease loading. In certain embodiments, the apparatus further comprises a continuing flag for the cartridge loading to continue. In some embodiments, the apparatus further comprises an insertion detector that comprises a light emitter/collector IR sensor. In some embodiments, the sensor detects a vessel label and verifies the therapeutic agent.

Provided herein is an apparatus for the controlled delivery of a therapeutic agent to a predetermined tissue site within a subject comprising: a cartridge assembly comprising a housing, a needle hub, a vessel configured to contain the therapeutic agent, wherein the housing comprises a vessel receiver configured to receive the vessel; an applicator comprising a cartridge assembly receiver, and an insertion detector, wherein the insertion detector is configured to sense loading of the vessel in the vessel receiver; and at least one injection orifice of an injection needle through which the therapeutic agent is administered; a plurality of penetrating electrodes arranged with a predetermined spatial relationship relative to the orifice; an electrode support comprising a plurality of apertures corresponding to the predetermined special relationship of the electrodes and through which the electrodes extend, wherein the electrode support structure prevents inadvertent perpendicular motion of the electrodes relative to the direction of electrode deployment; an electrical field generator configured to generate an electrical signal that is operatively connected to the electrodes; and a controlled source of energy sufficient to transfer a predetermined amount of the therapeutic agent at a predetermined rate from the reservoir through the orifice to the predetermined site within the subject.

In some embodiments, the apparatus further comprises a needle. In some embodiments, the apparatus further comprises an electrode insertion spring or a needle insertion spring. In some embodiments, the proximal portion of the electrode is separated from the distal portion of the electrode by an electrode shoulder or an electrode bend. In some embodiments, the electrode support provides an operative connection between a conductive contact region located on the distal region of the electrodes and the controlled source of energy when the electrodes are deployed into the predetermined tissue site within the subject. In some embodiments, the electrode support comprises a needle hole positioned to allow for passage of the injection needle therethrough. In some embodiments, the electrode support comprises a planar structure positioned perpendicularly relative to the elongate orientation of the electrodes. In some embodiments, the planar structure further comprises an aperture which is a hole or a slot configured to allow passage of the electrode therethrough to the predetermined tissue site. In some embodiments, the aperture comprises at least one tubular structure arranged perpendicularly to the planar structure. In some embodiments, the planar structure is oriented perpendicular to the longitudinal axes of the electrodes. In some embodiments, the electrode support is an adaptive electrode support. In some embodiments, the adaptive electrode support is a compression spring. In some embodiments, the compression spring is made from a metal, a polymer or an elastomeric material. In some embodiments, the electrode support comprises at least one telescoping tube. In some embodiments, the electrode support further comprises a stick shield spring. In some embodiments, the electrode support further comprises at least one lateral support member attached to the electrodes with at least one optional hinge feature. In some embodiments, the electrode support comprises a metal, a polymer, a ceramic, a composite, or a compressible matrix material. In some embodiments, the compressible matrix material is selected from the group consisting of a cellulose, a foamed plastic, a rubber polymer, a microcellular plastic, foamed silicon, foamed polychloroprene, carbon foam matrix. In some embodiments, the electrode support is made from an unconducive material. In some embodiments, the electrode support is made of a thermoplastic material. In some embodiments, the thermoplastic material is selected from the group consisting of a polycarbonate, polystyrene, polypropylene, an acrylic, or a polyethylene.

In some embodiments, the electrode support supports transcutaneous deployment of the electrode and maintains at tissue depths up to 60 mm. In some embodiments, an electrode proximal portion of each electrode is coupled to or contacts an electrode contact, wherein each electrode is positioned on the exterior of the inner cartridge of the cartridge assembly, wherein the electrode contact is configured for power communication with corresponding connections on the applicator. In some embodiments, the electrode contact further comprises an outer cartridge exterior contact. In some embodiments, the electrode contact provides an electrically conductive interface with corresponding electrodes while not interfering with forward travel of the electrodes mounted on the inner cartridge. In some embodiments, the cartridge assembly further comprises a vessel loading port. In some embodiments, an outer cartridge, said outer cartridge comprising an inner cartridge containment volume. In some embodiments, the applicator further comprises an injection drive assembly, wherein the injection drive assembly mates with the cartridge assembly. In some embodiments, the applicator further comprises a an applicator cartridge assembly receiving port. In some embodiments, the applicator further comprises a a procedure activation trigger. In some embodiments, the applicator further comprises a a connector for connection to the controller, a top housing, a side housing, and an inner protective shell. In some embodiments, the vessel further comprises a vessel cap. In some embodiments, the apparatus further comprises an egress port. In some embodiments, the apparatus further comprises a plunger stopper. In some embodiments, the apparatus further comprises a multiconductor cable. In some embodiments, the apparatus further comprises an exterior cartridge cap chamfer surface. In some embodiments, the apparatus further comprises an exterior cartridge cap hook. In some embodiments, the apparatus further comprises a main power port. In some embodiments, the apparatus further comprises a main power switch, a power button, and a power indicator. In some embodiments, the apparatus further comprises a at least one connector for switch.

Provided herein are embodiments wherein an apparatus described herein comprises a hybrid motor/spring mechanism for contacting at least one of said injection orifice or said plurality of electrodes with said predetermined tissue site.

In some embodiments, the apparatus further comprises a at least one connector for switch. In some embodiments, the apparatus further comprises an USB port. In some embodiments, the apparatus further comprises a reminder tab. In some embodiments, the apparatus further comprises a battery indicator. In some embodiments, the apparatus further comprises a mute button. In some embodiments, the apparatus further comprises at least one menu navigation button. In some embodiments, the apparatus further comprises an eject cartridge button. In some embodiments, the apparatus further comprises a display screen. In some embodiments, the apparatus further comprises a tray. In some embodiments, the apparatus further comprises an applicator connector port. In some embodiments, the apparatus further comprises an applicator cradle. In some embodiments, the apparatus further comprises a cradle. In some embodiments, the apparatus further comprises a storage bin. In some embodiments, the apparatus further comprises a handle. In some embodiments, the apparatus further comprises a abutment wall. In some embodiments, the apparatus further comprises at least one applicator electroporation electrode contact. In some embodiments, the apparatus further comprises at least one electrical connector. In some embodiments, the apparatus further comprises a cartridge loading subassembly. In some embodiments, the apparatus further comprises a motor drive and at least one electrical contact for motor drive. In some embodiments, the apparatus further comprises a loading drive motor. In some embodiments, the apparatus further comprises a motor trigger connector. In some embodiments, the apparatus further comprises a motor drive shaft. In some embodiments, the apparatus further comprises at least one electromechanical subassembly. In some embodiments, the apparatus further comprises at least one cartridge loading, electrode insertion, and injection subassembly. In some embodiments, the apparatus further comprises at least one injection depth selection button and an injection depth selection indicator. In some embodiments, the apparatus further comprises a procedure countdown timer. In some embodiments, the apparatus further comprises at least one gear cover bracket and at least one mounting bracket.

In some embodiments, the apparatus further comprises a system trigger switch. In some embodiments, the apparatus further comprises a system trigger switch. In some embodiments, the apparatus further comprises a procedure fault indicator and a procedure complete indicator. In some embodiments, the apparatus further comprises a depth selection button. In some embodiments, the depth selection button is selected from the group consisting of a toggle, a switch, and a sliding switch. In some embodiments, the apparatus further comprises a plurality of channel and a plurality of retaining post. In some embodiments, the apparatus further comprises an insertion mechanism gear drive ring and an insertion gear ring. In some embodiments, rotation of the insertion mechanism gear ring rotates the retaining post into the channel.

In some embodiments, the apparatus further comprises an insertion mechanism flag, an insertion mechanism drive motor, an insertion mechanism position sensor, an injection drive plunger, an injection drive motor, or an injection drive gearing. In some embodiments, the apparatus further comprises a cartridge lock ring. In some embodiments, the rotation of the cartridge lock ring rotates the retaining posts. In some embodiments, the cartridge assembly is for single use. In some embodiments, the applicator is for multiple uses. In some embodiments, the applicator further comprises a top housing, a side housing, an inner protective shell, a front cap, and an end cap. In some embodiments, the applicator further comprises a user interface, a procedure activation trigger, a procedure countdown timer, a procedure fault indicator, or an application placement indicator. In some embodiments, the apparatus further comprises a controller. In some embodiments, the controller comprises a controller assembly. In some embodiments, the applicator further comprises a connector for connection to the controller. In some embodiments, the controller further comprises an electrical field controller.

In some embodiments, the penetrating electrodes and/or the injection needle come in contact with the predetermined tissue site with velocity of at least 50 mm/second. In some embodiments, the penetrating electrodes and/or the injection needle come in contact with the predetermined tissue site with velocity of at least 500 mm/second. In some embodiments, the therapeutic agent is a nucleic acid. In some embodiments, the nucleic acid is DNA. In some embodiments, the predetermined tissue site is located in a skeletal muscle of the subject. In some embodiments, the skeletal muscle of the subject is medial deltoid muscle or vastus lateralis muscle. In some embodiments, an injection depth at medial deltoid muscle is about 19-30 mm. In some embodiments, an injection depth at vastus lateralis muscle is about 25-38 mm.

In some embodiments is provided an apparatus comprising a hybrid motor/spring mechanism for contacting at least one of said injection orifice or said plurality of electrodes with said predetermined tissue site. In some cases, the apparatus further comprises a measurement and logic circuit to monitor the current usage of motor during the injection stroke and compare said usage to a predetermined standard.

Provided is an apparatus described herein, further comprising a controller and a force contact circuit wherein a feedback loop exists between said controller and said force contact circuit such that upon insertion of said plurality of electrodes in said predetermined tissue site, detection of a change in an applied force prompts initiation of a check as to whether the electrodes remain properly deployed in said predetermined tissue site.

In some cases is an apparatus described herein wherein the plurality of electrodes and/or one or more needle are deployed by rotational motion.

Provided is a method of providing a therapeutic agent to a predetermined tissue site in a subject in need thereof, comprising contacting said subject with an apparatus described herein. Provided are systems for providing a therapeutic agent to a predetermined tissue site in a subject in need thereof, comprising an apparatus described herein.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIGS. 3A-3B show views of aspects of a device described herein. FIG. 3A shows a lateral view of a cartridge assembly 100 according to present principles. FIG. 3B shows a lateral view of a reservoir 101 embodied as a syringe, according to present principles.

FIG. 5A illustrates a top view of an inner cartridge 103 according to present principles. FIG. 5B illustrates a bottom view of an inner cartridge 103 and cartridge breech according to present principles. FIG. 5C illustrates a detail side perspective view of an inner cartridge 103 according to present principles. FIG. 5D shows a lateral view of a cartridge breech 112 according to present principles. FIG. 5E illustrates vessel interlock 120 with improved locking features to prevent the cartridge breech 112 from inadvertently moving forward.

FIG. 7A shows details of one or more electrode contact 130 and various elecrode contact portions according to present principles. FIG. 7B shows details of electrodes 122 and various electrode contact portions according to present principles.

FIG. 8A shows a top view of a force contact interlock system according to the present principle. FIG. 8B illustrates details of a force contact interlock system according to present principles.

FIG. 9A shows a needle 105 and distal inner cartridge electrodes 137 for tissue insertion according to present principles. FIG. 9B illustrates details of a stick shield 134 according to present principles. FIG. 9C illustrates an alignment guide 108 and splay shield 108 according to present principles. FIG. 9D illustrates stick shield supports intergral to outer cartridge cap 106.

FIG. 10A shows an exterior cartridge cap 110 according to present principles. FIG. 10B shows a side view of an exterior cartridge cap 110 according to present principles. FIG. 10C shows an exterior cartridge cap 110 in use in an alignment guide 108 and splay shield according to present principles. FIG. 10D shows an exterior cartridge cap 110 with extension members designed to hold the inner cartridge 103 in place during handling and loading.

FIG. 11A shows a stick shield retaining hook 182 of a stick shield 134 according to present principles. FIG. 11B shows details of a stick shield 134 according to present principles. FIG. 11C shows stick shield supports 132 keeping a stick shield 134 in place according to present principles.

FIG. 13A shows side view of an applicator 400 according to present principles. FIG. 13B shows top views of an applicator 400 according to present principles.

FIGS. 17A-17B show views of an applicator in a device described herein. FIG. 17A is an exploded view of an applicator according to present principles, showing a loading drive subassembly 454. FIG. 17B shows a rack 154 in a loading drive subassembly 454 according to present principles.

FIG. 18A shows details of a cartridge loading subassembly 456 according to present principles, showing where the insertion/injection drive assembly of the applicator mates with the cartridge assembly. FIG. 18B shows a cross-sectional view of a cartridge assembly according to present principles, showing where the insertion/injection drive assembly of the applicator mates with the cartridge assembly. FIG. 18C shows details of cartridge loading, electrode insertion, and injection subassemblies 452 of an applicator 400 according to present principles.

FIGS. 20A-20D show views of a device described herein. FIG. 20A shows various components of a controller system according to present principles. FIG. 20B shows details of an applicator connector port 708 and a tray 710 of a controller system according to present principles.

FIG. 20C shows details of a stimulator display screen of a controller system according to present principles. FIG. 20D shows details of a rear view of a controller system according to the present principles.

Like reference numerals refer to like elements throughout. Elements are not to scale unless otherwise noted.

DETAILED DESCRIPTION

Figure 1:
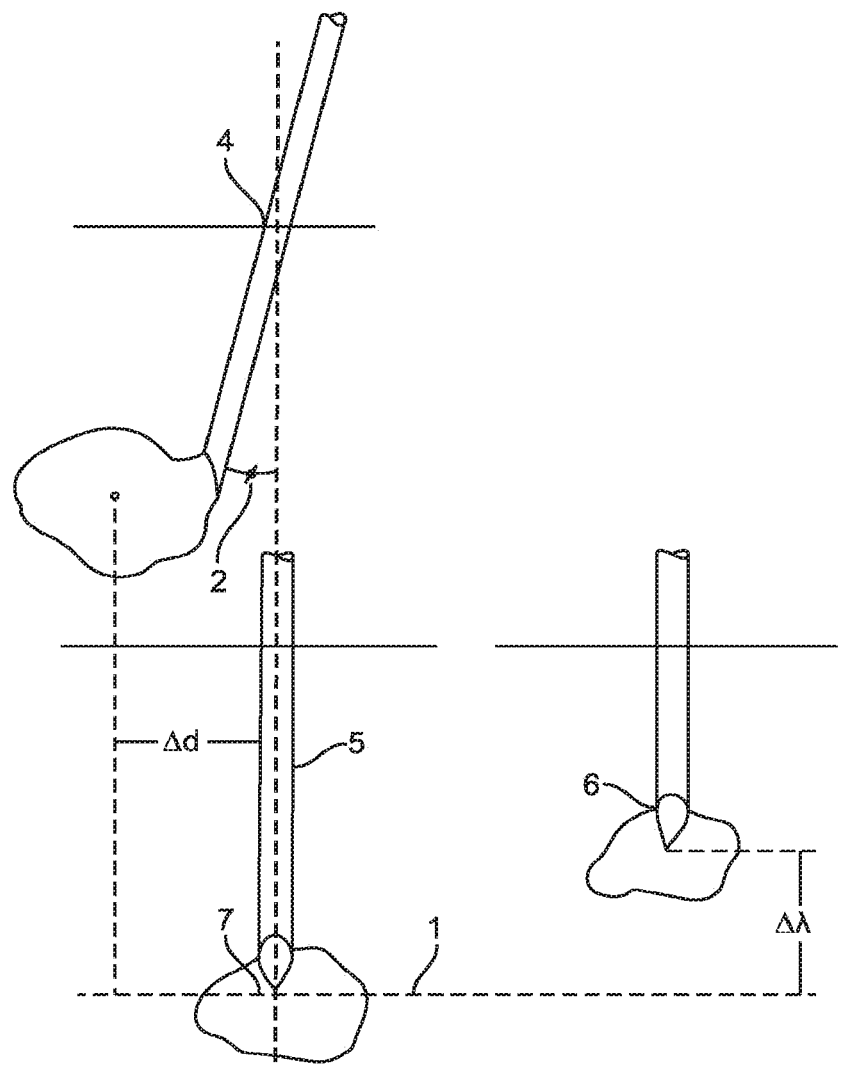
FIG. 1 illustrates potential sources of spatial variability associated with conventional needle syringe injection.

The following description and examples illustrate embodiments of the invention in detail. It is to be understood that this invention is not limited to the particular embodiments described herein and as such can vary. Those of skill in the art will recognize that there are numerous variations and modifications of this invention, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the invention may be described in the context of a single embodiment, the features may also be provided separately or in any suitable combination. Conversely, although the invention may be described herein in the context of separate embodiments for clarity, the invention may also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the inventions.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the invention, and vice versa. Furthermore, compositions of the invention can be used to achieve methods of the invention.

The term "about" in relation to a reference numerical value and its grammatical equivalents as used herein can include the numerical value itself and a range of values plus or minus 10% from that numerical value. For example, the amount "about 10" includes 10 and any amounts from 9 to 11. For example, the term "about" in relation to a reference numerical value can also include a range of values plus or minus 10%, 9%, 8%, 7%, 6%, 5%, 4%, 3%, 2%, or 1% from that value.

The present disclosure provides improved system, methods and apparatus for the reproducible, consistent, and efficacious delivery of therapeutic agents, such as nucleic acids, drugs, peptides, proteins and combinations thereof with Electrically Mediated Therapeutic Agent Delivery (EMTAD).

In one aspect, the present disclosure provides an apparatus for the delivery of a therapeutic agent to a predetermined site within a subject comprising an administrator for controlled administration of the therapeutic agent to the subject comprising a reservoir or vessel for the therapeutic agent, at least one orifice through which the agent is administered, and a controlled source of energy sufficient to transfer a predetermined amount of the therapeutic agent at a predetermined rate from the reservoir or vessel through the orifice to the predetermined site within the subject. In addition, the apparatus comprises a plurality of penetrating electrodes arranged with a predetermined spatial relationship relative to the orifice, and an electrical signal generator operatively connected to the electrodes. The terms reservoir and vessel are used interchangably throughout the specification to refer to a container for the therapeutic agent.

In certain aspects of the present disclosure, EMTAD can be refered to as the administration of a therapeutic agent to a biological tissue of interest and the earlier, concurrent or subsequent application of electrical signals to biological tissue for the purpose of enhancing movement and/or uptake of the therapeutic agent in said tissue. The process of EMTAD is comprised of two elements: 1) Therapeutic Agent Administration (TAA), and 2) an Electrical Signal Application (ESA) sufficient to induce the desired EMTAD effect. In the present disclosure, therapeutic agent administration can be accomplished, for instance, in a controllable fashion, termed Controlled Therapeutic Agent Administration (CTAA). The term CTAA used herein refers to methods and apparatus that provide spatial and/or temporal control over administration of a therapeutic agent relative to the induction of an EMTAD effect. Controllable administration techniques can utilize variations on the conventional needle-syringe (e.g. automatic injection device) and/or various needleless methodologies (e.g. jet injector, transdermal/transcutaneous patch, oral, gel, cream, or inhaled administration). The term ESA used herein refers to the application of electrical signals to facilitate or enhance the delivery of therapeutic agents by improving movement and/or uptake of said agents within tissue, thus inducing an EMTAD effect. When used to facilitate or enhance delivery of a therapeutic agent, ESA processes such as electroporation, iontophoresis, electroosmosis, electropermeabilization, electrostimulation, electromigration, and electroconvection all represent various modes of EMTAD.

Specific applications for apparatus and systems described herein include, but are not limited to, the delivery of vaccines, therapeutic proteins, and chemotherapeutic drugs. Traditionally with such applications, EMTAD is initiated by therapeutic agent injection using a conventional needle-syringe. After the agent has been administered, a device suitable for ESA is applied to the subject at a designated location. Finally, an appropriate ESA protocol is utilized to provide the desired facilitation or enhancement to therapeutic agent delivery. With traditional EMTAD, however, the desired spatial and temporal relationship between agent administration and ESA may not be realized.

Spatial Parameters

In some embodiments of the systems, methods and apparatus described herein, therapeutic agent administration is performed using a conventional needle syringe. The need to deliver certain agents with EMTAD brings an additional level of complexity to the issue of TAA. As depicted in FIG. 1, in any conventional needle-syringe injection, as the needle 5 is inserted into the tissue, the depth 1 and the angle 2 of insertion relative to the surface of the tissue 3 can be difficult to control. Additionally, the point of needle penetration 4 at the tissue surface 3 may not be representative of the location of the orifice 6 and the region of agent administration 7 within the target tissue. As an illustrative example a transcutaneous intramuscular injection may not correspond to the site of insertion on the skin since the two tissues can often move in relation to one another.

While this conventional approach is generally adequate for the delivery of many different therapeutics that do not require EMTAD, these variables lead to a distribution of the therapeutic agent following injection that is often inconsistent and/or indeterminate and can hamper effective EMTAD. In certain embodiments described herein, the most effective use of EMTAD utilizes a predefined relationship between the therapeutic agent and ESA within the subject. As a result, in the absence of spatial control over TAA in a target tissue, using a conventional needle syringe can result in reduced effectiveness of the EMTAD application, as compared to an apparatus, method or system that provides spatial and temporal control. One illustrative example of this concept is the use of electroporation to facilitate the delivery of a therapeutic agent. Electroporation is typically most effective in enhancing therapeutic agent delivery when TAA and ESA are co-localized within the target region of tissue. In many cases, if the agent to be delivered and the induced electroporation effect are not co-localized within the target region of tissue, the delivery of said agent is suboptimal.

Another example of the need for adequate spatial control of TAA in EMTAD is iontophoresis. This mode of EMTAD uses electrical fields to cause movement of charged molecules. In order to achieve the desired movement of the agent, the proper spatial relationship between the electrodes and the therapeutic agent must be realized. If a negatively charged agent were placed in close proximity to the location of a positive electrode, little or no movement of the agent through the tissue would be observed. In contrast, localization of the said negatively charged agent near the negative electrode would result in significant movement of the agent through the tissue in the direction of the positive electrode.

As illustrated by the preceding examples, it is important to control the precise location of TAA relative to the application of ESA to achieve the desired effect. As such, embodiments of the apparatus and methods described herein provide control of the precise location of TAA relative to the application of ESA, and are useful to achieve reproducible, consistent, and well-characterized distribution of one or more therapeutic agents.

Temporal Parameters

In the case of conventional needle-syringe injection TAA is that the rate of injection may vary from one operator to another, thereby causing inconsistent agent distribution in the tissue. Additional temporal variability is introduced when multiple device placements are required to complete the EMTAD process. For example, one application of EMTAD calls for the administration of plasmid DNA encoding for a therapeutic protein, followed by generation of an electroporation-inducing electrical field. Using the traditional method of EMTAD, the plasmid is injected with a needle-syringe, followed by placement and activation of the electroporation device. By requiring two separate device placements (the initial needle syringe followed by the ESA device), this procedure is susceptible to inter-subject variability arising from inconsistent temporal application of each device by the operator. Additionally, the use of two separate device placements leads to an unavoidable time interval in between the clinician's placement and activation of each device. This is compounded in the case where multiple application sites are necessary to achieve adequate delivery of the agent to a specifiable region within the target tissue.

These issues are especially critical for agents, such as nucleic acids, that can be degraded or inactivated in the extracellular environment. Therapeutic agent degradation can lead to a reduction in efficacy and consistency in the application of the therapy. Also, the inter-subject rate of therapeutic agent degradation is not constant, thus contributing to the overall therapeutic inconsistency of conventional needle-syringe injection combined with ESA, and more specifically with electroporation therapy.

Due to the inherent difficulty of spatial and temporal variability with conventional needle-syringe injection used in conjunction with ESA, the precise location and timing of TAA relative to ESA is often unknown. As a result, the effective administration and dosing of therapeutic agents with EMTAD may be inconsistent and irreproducible. Though conventional needle-syringe injection is sometimes adequate for therapeutic agent administration, reproducible and consistent agent delivery is significantly enhanced by controlling the spatial and temporal relationship between administration of the therapeutic agent and induction of the desired EMTAD effect.

Thus, while the traditional EMTAD procedure may be adequate for certain applications, temporal and spatial control is highly desirable for clinical applications that typically require a high degree of consistency and reproducibility. In contrast to the conventional EMTAD approach, embodiments of methods, systems and apparatus described herein facilitate CTAA and ESA to provide more advantageous methods and apparatus for the clinical application of EMTAD. The present disclosure utilizes various aspects of CTAA in conjunction with ESA to provide reproducible, consistent, and efficacious therapeutic agent delivery. The present disclosure describes methods and apparatus to provide spatial and temporal control over administration of a therapeutic agent relative to the application of electrical signals, thereby improving the movement and/or uptake of said agent in the target tissue.

In some embodiments are provided methods and apparatus wherein there exists a controllable spatial relationship for the administration of the therapeutic agent relative to the application of electrical signals. Prior to treatment, the optimal location for TAA relative to ESA is determined. This spatial relationship between TAA and ESA is dictated by treatment parameters, including the nature of the agent being administered and the properties of the target tissue to which the agent is administered. In an exemplary embodiment, electrical signals are preferentially applied distal to the site of therapeutic agent administration. In certain other embodiments, spatial relationship is to apply the EMTAD-inducing electrical signals proximal to the site of agent administration. In certain cases, co-localization between TAA and ESA is preferable. This is often the case when electroporation and/or iontophoresis are utilized for induction of the desired EMTAD effect.

In another aspect of the present disclosure, an apparatus described herein provides a controllable temporal relationship for the sequence and timing of TAA relative to ESA. Prior to treatment, the optimal sequence and timing for combination of TAA and ESA is determined. As with the spatial relationship, the desired temporal relationship between TAA and ESA is dictated by parameters such as the nature of the agent being administered and the properties of the target tissue to which the agent is administered. In certain applications, exposure to the electrical fields associated with ESA may adversely affect the therapeutic agent. In the practice of such applications, generation of such electrical fields is followed by CTAA. However, the typical temporal relationship is CTAA followed by ESA.

The present disclosure provides improved methods and apparatus for the reproducible, consistent, and efficacious delivery of therapeutic agents, such as nucleic acid based constructs, pharmaceutical compounds, drugs, and proteins, with EMTAD. This objective is accomplished by controlling the spatial and temporal administration of a therapeutic agent relative to application of electrical signals. Exemplary therapeutic agents for EMTAD include, but are not limited to, the delivery of vaccines, therapeutic proteins, and chemotherapeutic drugs. In a certain embodiment, EMTAD is initiated by therapeutic agent injection using a conventional needle-syringe. After the agent has been administered, a device suitable for ESA is applied to the subject at a designated location. An appropriate ESA protocol is utilized to provide the desired facilitation or enhancement to therapeutic agent delivery. An exemplary ESA method that has proven to be effective in virtually all cell types is electroporation. Other exemplary methods of electrically mediated delivery include, but not limited to, iontophoresis, electroosmosis, electropermeabilization, electrostimulation, electromigration, and electroconvection. These terms are used for illustrative purposes only and should not be construed as limitations in the present disclosure.

The technique of electroporation utilizes the application of electric fields to induce a transient increase in cell membrane permeability and to move charged particles. By permeabilizing the cell membranes within the target tissue, electroporation dramatically improves the intracellular uptake of exogenous substances that have been administered to the target tissue. The increase in cell membrane permeability and molecular movement due to electroporation offers a method for overcoming the cell membrane as a barrier to therapeutic agent delivery. The application of electroporation as a technique for inducing EMTAD is advantageous in that the physical nature of the technique allows electroporation to be applied in virtually all tissue types. Accordingly, various aspects and embodiments of the present disclosure discuss, but are not limited to, electroporation as a technique for inducing EMTAD.

Therapeutic Agents

The term "therapeutic agent" is used herein in its broadest sense to include any agent capable of providing a desired or beneficial effect on living tissue. Thus, the term includes both prophylactic and therapeutic agents, as well as any other category of agent having such desired effects. Clearly, the scope of the present disclosure is sufficiently broad to include the controlled delivery of any agent, however categorized. Therapeutic agents include, but are not limited to pharmaceutical drugs and vaccines, and nucleic acid sequences (such as supercoiled, relaxed, and linear plasmid DNA, RNA, antisense constructs, artificial chromosomes, or any other nucleic acid-based therapeutic), and any formulations thereof. Such agent formulations include, but are not limited to, cationic lipids, cationic and/or nonionic polymers, liposomes, saline, nuclease inhibitors, anesthetics, poloxamers, preservatives, sodium phosphate solutions, or other compounds that can improve the administration, stability, and/or effect of the therapeutic agent. Additional formulations include agents and additives conferring the ability to control viscosity and electrical impedance of the administered agent.

In the case of nucleic acids, an example of a therapeutic agent would be plasmid DNA dissolved in a phosphate buffered sodium chloride solution with a competitive nuclease inhibitor such as aurintricarboxylic acid (ATA) added to the agent. In some embodiments using nucleic acid-based therapeutics, it may also be advantageous to incorporate a signaling peptide onto the construct. Potentially useful peptides include, but are not limited to, nuclear localization signals, endosomal lyric peptides, and transcriptional control elements. These signals can enable improved delivery and/or processing of the therapeutic agents delivered to the cells via EMTAD. This signaling can be accomplished through the use of methods as described in U.S. Pat. No. 6,165,720 (the entire disclosure of which is incorporated by reference herein). While these techniques can be utilized with other delivery systems, the ability of EMTAD to increase the delivery of nucleic acid constructs to target tissues makes it particularly well suited for use with such signals.

Target Tissues

Target tissues well suited for EMTAD by use of methods, apparatus and systems described herein include both healthy and diseased cells located in, for instance, the epidermis, dermis, hypodermis, connective, and muscle tissue. The technique can also be utilized for application in healthy or diseased organs that must be accessed via minimally invasive or other surgical methods. Such target tissues include the liver, lungs, heart, blood vessels, lymphatic, brain, kidneys, pancreas, stomach, intestines, colon, bladder, and reproductive organs. In some embodiments, a desired therapeutic effect can be derived by use of a method, or apparatus described herein to deliver an amount of agent to cell types normally located within the target tissues as well as other cell types abnormally found within said tissues (e.g. chemotherapeutic treatment of tumors).

As discussed previously, and depicted in FIG. 1, traditional EMTAD suffers from a lack of precision and reproducibility in the spatial and temporal relationship between the administration of the therapeutic agent and the electrical signal. In contrast to the traditional EMTAD approach, the present disclosure describes methods and apparatus for combined CTAA and ESA to provide a more advantageous clinical application of EMTAD. The present disclosure utilizes various aspects of CTAA in conjunction with ESA to provide reproducible, consistent, and efficacious therapeutic agent delivery. The methods and apparatus provided herein provide spatial and temporal control over administration of a therapeutic agent relative to the application of electrical signals, thereby improving the movement and/or uptake of said agent in the target tissue.

Methods

In one aspect, the present disclosure described herein provides systems and apparatus for use in methods for controlled administration of a therapeutic agent followed by ESA. In another aspect, the present disclosure described herein provides systems and apparatus for use in methods for controlled administration of a therapeutic agent preceded by ESA. In a further aspect, the present disclosure described herein provides systems and apparatus for use in methods for controlled administration of a therapeutic agent paccompanied by ESA. These methods include, but are not limited in scope or sequential relationship to, the determination of treatment parameters, subject preparation procedures, CTAA, ESA, and additional measures.

Determination of Treatment Parameters

In some embodiments, treatment parameters are based on the desired amounts and/or duration of dosing of the therapeutic agent. Therapeutic agent dosing can depend, for instance, on the particular indication or treatment application (such as the type and location of the target tissue), as well as various subject parameters (such as age and body mass). Dosing of the therapeutic agent can be controlled by parameters pertaining to administration of the therapeutic agent and ESA. Exemplary controllable parameters pertaining to CTAA include, but are not limited to, agent volume, agent viscosity, and injection rate. Exemplary controllable parameters pertaining to ESA include, but are not limited to, the characteristics of the electrical signals, the tissue volume exposed to the electrical signals, and the electrode array format. The relative timing and location of CTAA and ESA are parameters providing further control over therapeutic agent dosing.

Patient/Subject Preparation

In embodiments described herein, methods described herein may include a patient/subject preparation step. The subject preparation may include, but is not limited to, antiseptic cleansing and anesthetic administration, including local or regional, nerve block, spinal block, epidural block, or general anesthesia. In an exemplary case of intramuscular (IM) ESA, protocols to minimize the effects of electrical stimulation of the muscle may be included in a method described herein, for instance, including thermal control (e.g. cooling the muscle), administration of anesthetics, and/or alternative stimulation patterns sufficient for mitigation of discomfort. It is to be understood that the selected subject preparation techniques do not adversely affect therapeutic efficacy, if acceptable alternatives exist. For example, it has been shown that in some cases, the intramuscular administration of amide based anesthetics can have an undesirable effect on intramuscular delivery plasmid DNA-based therapies, putatively due to the mild myotoxicity of these agents, which can inhibit the muscle cells ability to express the protein encoded by the administered DNA sequence.

CTAA and ESA

In some embodiments described herein, is a method wherein CTAA and ESA are combined, enabling consistent and reproducible therapeutic agent delivery. In some cases, are provided apparatus suitable for CTAA, including for instance apparatus comprising at least one of automatic injection devices and jet injectors.

The present disclosure provides methods and apparatus enabling the transcutaneous deployment of a plurality of elongate electrodes to a target depth in a safe and consistent manner with respect to a target site of agent distribution in recipients with heterogeneous skin thickness and composition in order to support the application of electrical fields in tissue to enhance the intramuscular, intradermal, and/or subcutaneous administration of therapeutic or prophylactic agents such as nucleic acids, pharmaceuticals, antibodies, peptides, proteins, or combinations thereof.

Systems and methods according to present principles enable the consistent transcutaneous deployment of a plurality of elongate, tissue penetrating electrodes to a predetermined target tissue site in order to propagate electrical fields in the skin, subcutaneous tissue and/or skeletal muscle. The present disclosure provided herein is designed to enable a user with minimal training to consistently deploy the electrodes to a target depth while maintaining the proper spatial relationship among the plurality of electrodes, even when the procedure is applied at sites with varying skin characteristics. Such variation can be due either to variation in skin characteristics at different sites within an individual or among heterogeneous recipient populations. In other words, systems and methods according to present principles should allow a consistent profile irrespective of the administrator or the recipient. In certain embodiments, the deployment of the electrodes is accompanied by the insertion of one or more injection needles which are configured for the administration of therapeutic agents to the target region of tissue and arranged in a pre-determined spatial relationship with the electrodes to be used for ESA. In an exemplary embodiment, the electrodes are arranged such that any electrical signals from said electrodes are preferentially applied distal to the site of therapeutic agent administration by the insertion of one or more injection needles. In another embodiment, the electrodes are arranged such that any electrical signals are preferentially applied proximal to the site of therapeutic agent administration by the insertion of one or more injection needles.

Aspects of the present disclosure can be used singly or in combination to support the transcutaneous insertion of electrodes for the in vivo application of electrical fields to enhance the intramuscular, intradermal, and/or subcutaneous administration of nucleic acids, small molecule drugs, antibodies, peptides, proteins, and combinations thereof. In some embodiments, the electrode deployment and subsequent electrical field propagation are performed in coordinated fashion with the distribution of the agent of interest to the target tissue site. In an exemplary embodiment, the administration of the agent and the application of one or more electrical field are performed in a controlled and monitored fashion such that the probability of achieving spatial and temporal co-localization of the distribution of the agent with the site of electric field application is maximized.

Figure 2:
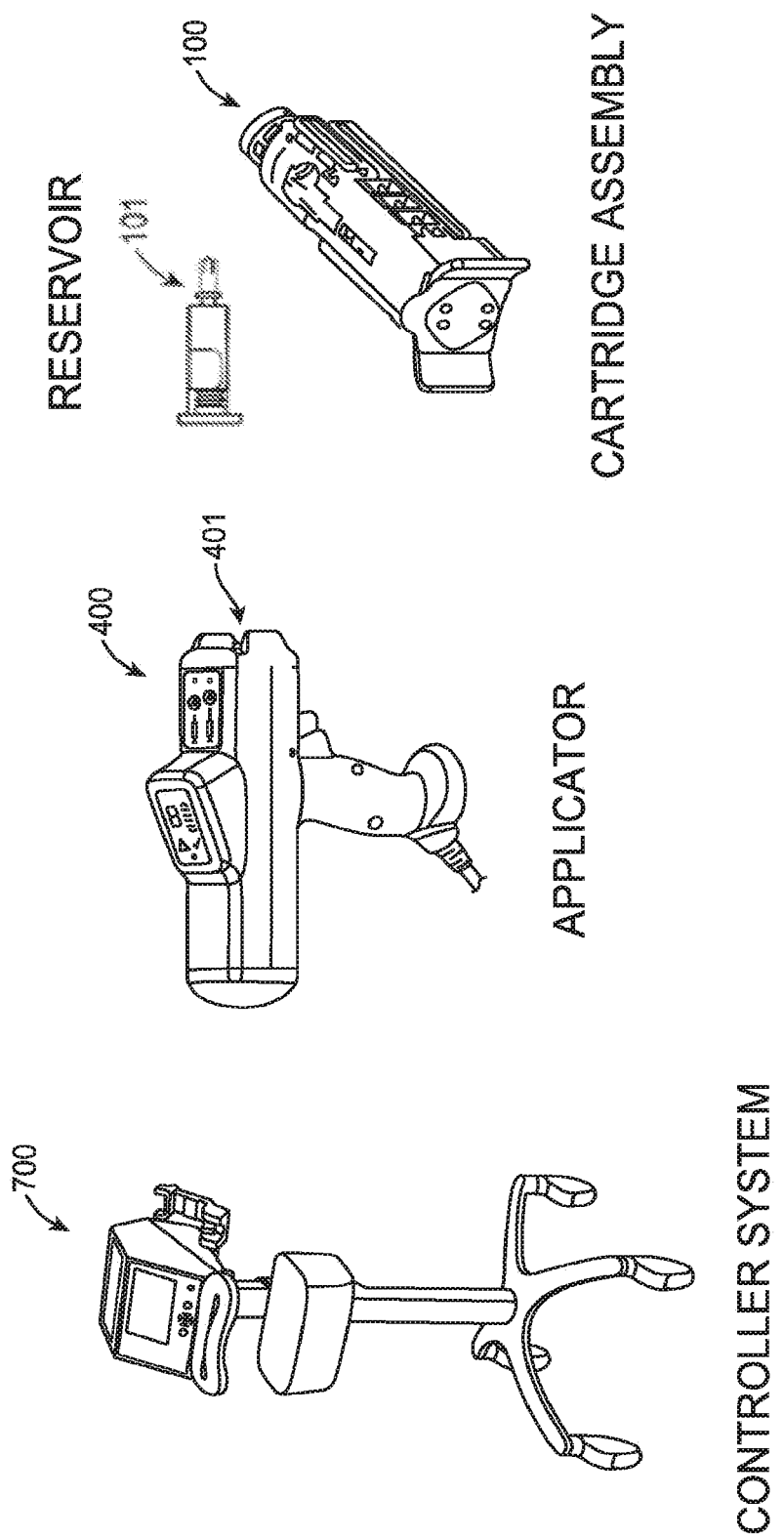
FIG. 2 is an overview of a system according to present principles, including a cartridge assembly 100, an applicator 400, and a controller system 700.

In general terms, the present disclosure provides methods and apparatus for the transcutaneous deployment of electrodes to a predetermined site within the skin, subcutaneous tissue, and/or skeletal muscle of a recipient in conjunction with the administration of an agent of interest and the local application of electrical fields to improve the delivery, uptake, and/or biological effect of the agent. In some embodiments, the present disclosure has been implemented such that set up and usage of the device can be performed effectively and reliably by users with minimal training. In another embodiment, the present disclosure also comprises the implementation of numerous interlocks, sensors, and feedback loops to reduce the frequency and/or potential impact of potential user errors committed during the set up and use of the device. Referring to FIG. 2, one embodiment of an apparatus described herein comprises a "cartridge assembly" 100 detachably interfaced to an "applicator" 400 which is configured to connect to a controller 700 which acts as source of electrical energy for electrode activation and subsequent electrical field generation, as well as diagnostics and other control routines. The controller 700 further provides a user interface, tray, holster for the applicator 400, and various other features are described. As seen in FIG. 2, a reservoir or vessel 101 of suitable uniform size and general shape can inserted in the cartridge assembly 100 in a method of use.

Figure 18A:
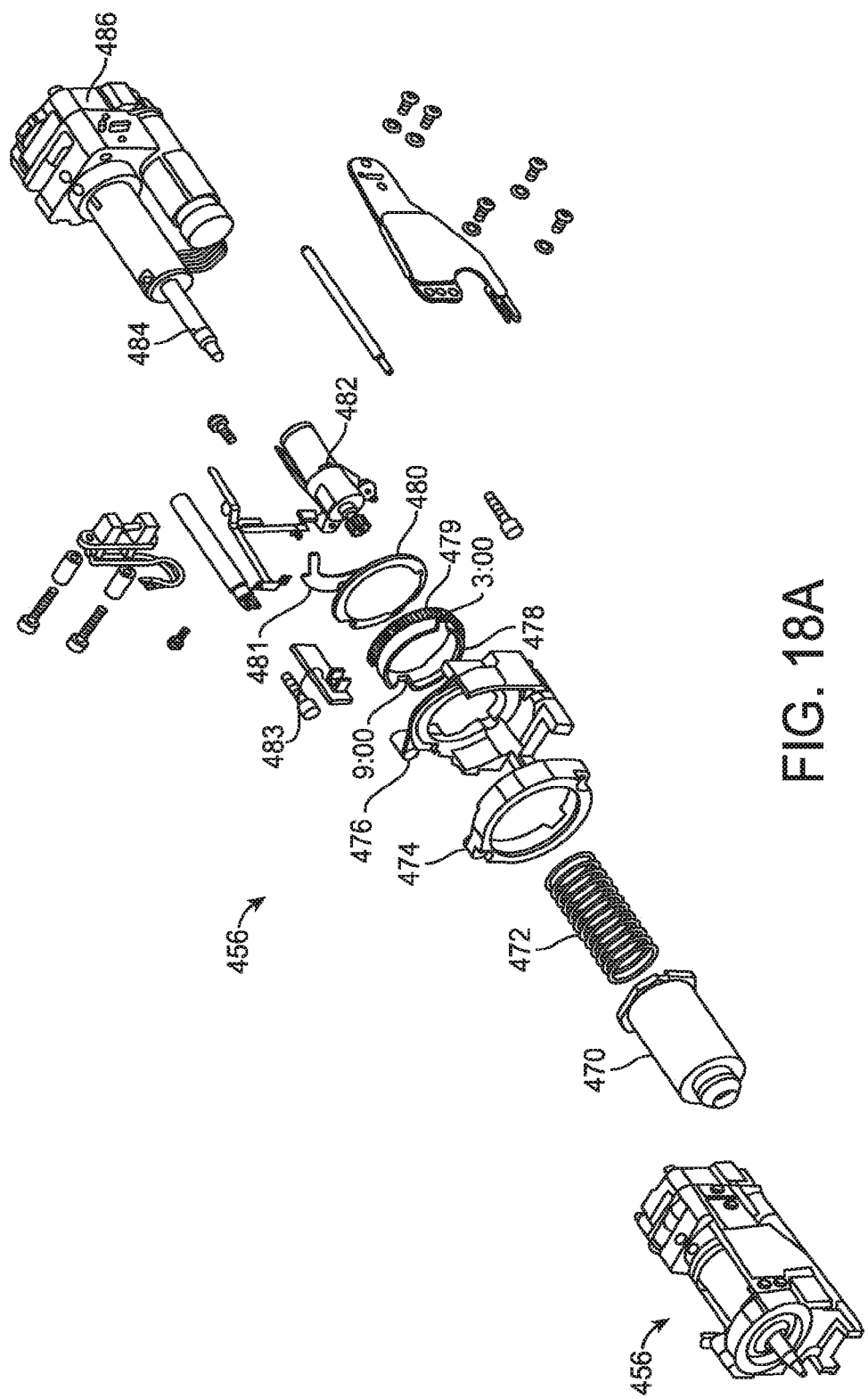
FIGS. 18A-18C show views of aspects of an applicator in a device described herein.
Figure 18B:
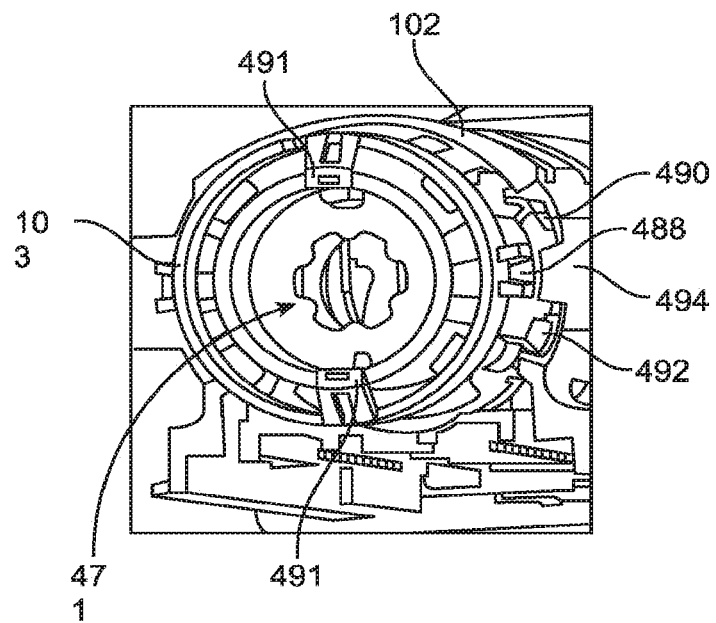
Figure 18C:
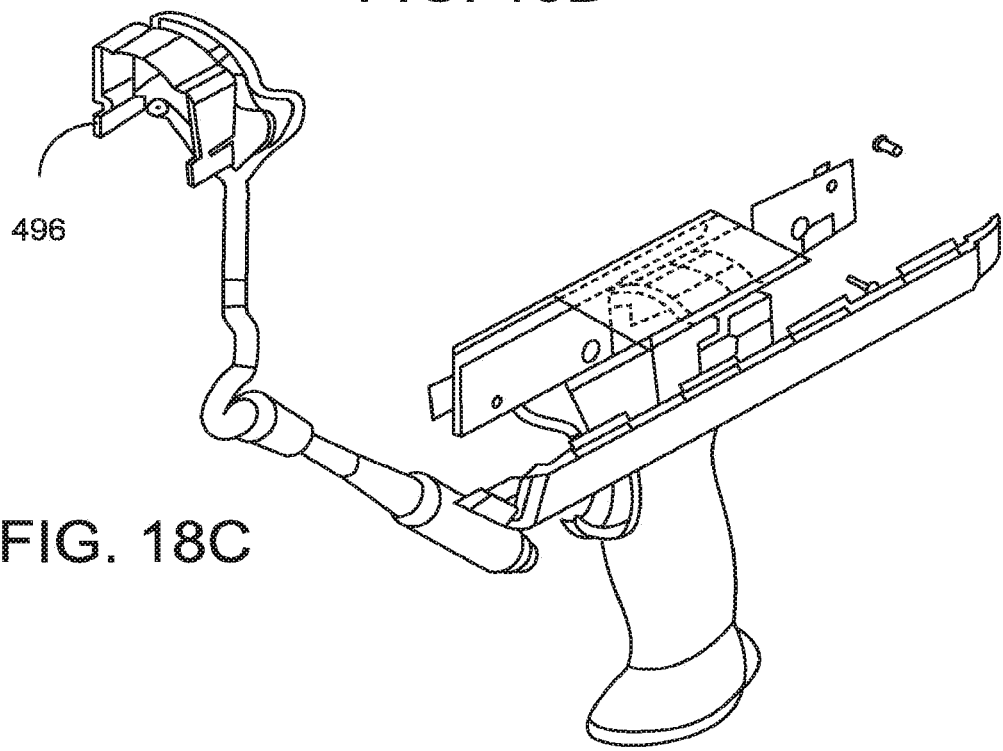
Figure 19:
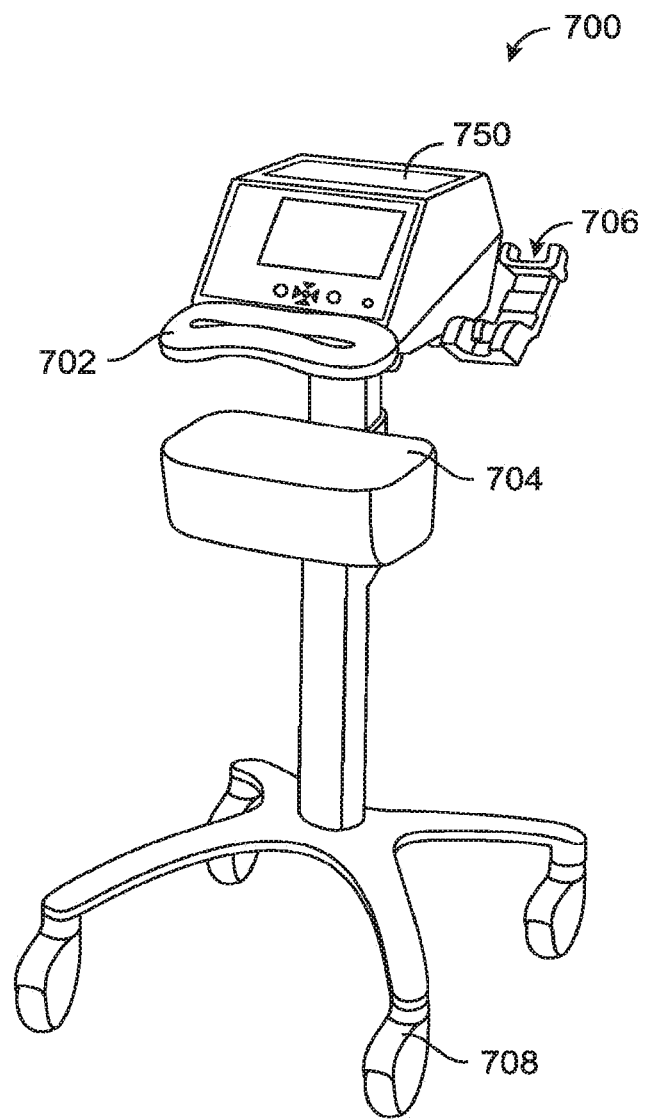
FIG. 19 shows various components of a controller system according to present principles.

Details of a cartridge assembly 100 present in some embodiments of an apparatus described herein, are described for instance, in FIGS. 3A-12, along with corresponding cooperating portions of the applicator 400, in FIGS. FIGS. 13A-18C, followed by, where relevant, portions of the controller 700, in FIGS. 19-20D. Remaining portions of the applicator 400 are described next, followed by remaining portions of the controller 700.

Figure 4:
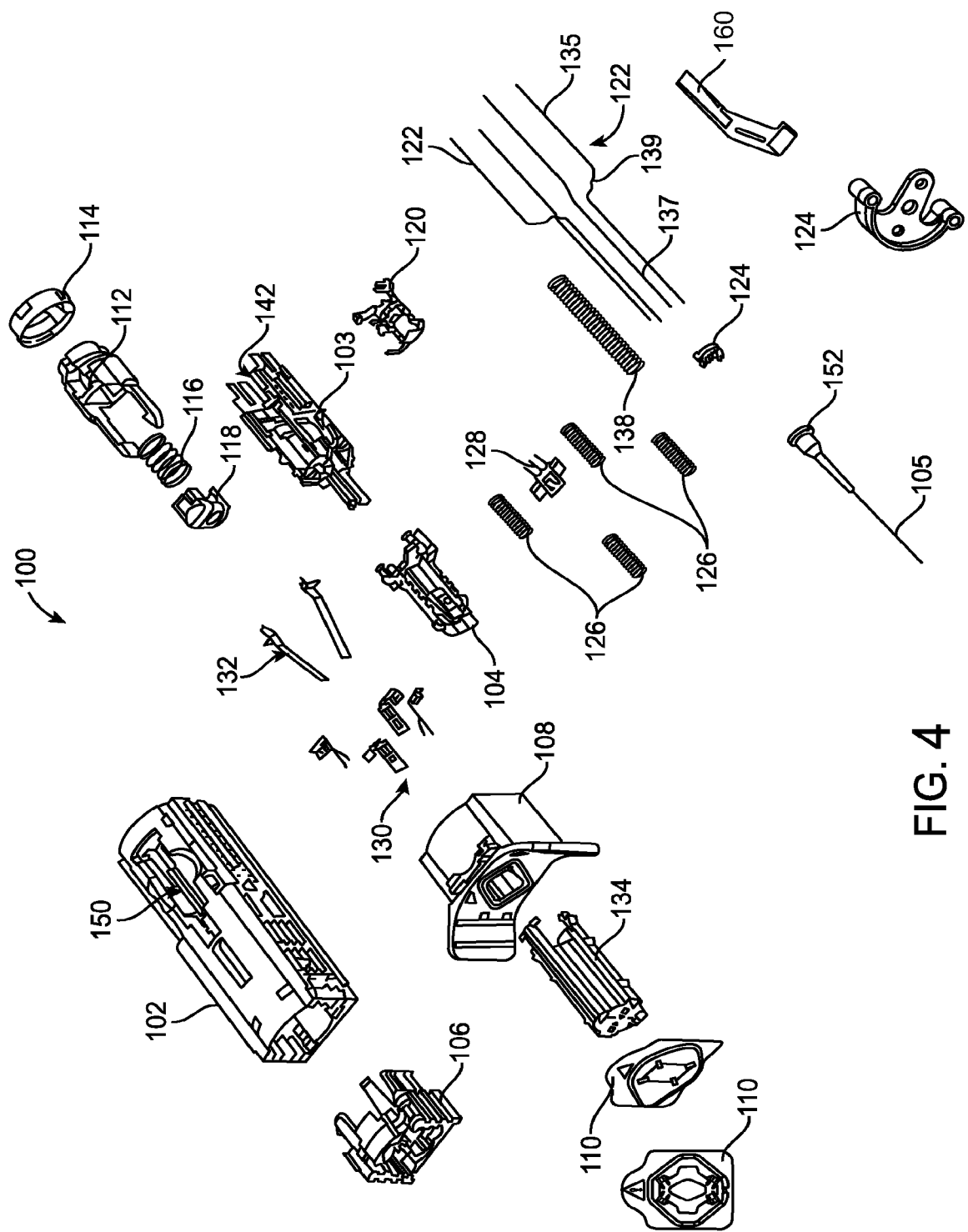
FIG. 4 shows various exemplary components of a cartridge assembly 100 according to present principles.

Referring in addition to FIGS. 3A-4, in some embodiments described herein, the cartridge assembly 100 can comprise a support structure configured to interface with the applicator 400 and accommodating two or more elongate electrodes 122 mounted on the structure to form an array. To avoid unwanted propagation of electrical currents within the device, the design and materials of the electrode mounting structure should be specified such that there is an adequate dielectric barrier between electrodes of opposite polarity within the device. The distal region 137 of the elongate electrodes are engaged with the mounting structure using standard mechanical features and/or bonding agents appropriate for the material composition of the electrode mount structure and the electrodes.

In an exemplary embodiment, the cartridge outer housing structure 102 is configured to interface with a fluid reservoir or vessel 101 containing the agent of interest where the reservoir or vessel 101 and cartridge housing structure 102 are configured to operatively connect to at least one injection orifice (needle 105) through which the agent is administered into the target tissue. In some embodiments, this configuration facilitates the co-localization of the distribution of the agent of interest with the site of electrical field application. In another embodiment, this configuration facilitates the implementation of a pre-determined spatial relationship between the apparatus for ESA and CTAA. In yet another exemplary embodiment, a syringe 101 is inserted into a cartridge 100, wherein upon loading of the cartridge into an applicator 400, the syringe 101 moves forward to mate with the needle hub 152 and to connect the cartridge to the needle.

Certain embodiments of the present disclosure can include the use of syringes, vials, ampoules, cartridges or equivalent structures for storing one or more therapeutic agents. In some embodiments, the reservoir or vessel can comprise at least one of glass and plastic, with the material selected for compatibility with the agent of interest. Coatings may be applied to the reservoir or vessel used to provide desirable lubricious or protective properties. As disclosed above, the electrodes 122 may be hollow and in some cases configured with injection orifices that can be operatively connected to the fluid vessels. Alternatively, the injection orifice can comprise one or more hypodermic needles and/or needle free injection ports positioned relative to the electrodes. Selection of the type and size of injection orifice can dependent on the desired route of administration, tissue distribution, and physical characteristics of the agent of interest. In a certain embodiment, the cartridge structure is designed to ensure a pre-determined spatial relationship between the injection orifice and electrodes in their deployed state such that the distribution of the agent of interest occurs substantially in the tissue bounded by the conductive regions of the plurality of electrodes. To minimize the need for handling of sharps by the user, in a certain embodiment, a cartridge 100 designed for use with hypodermic needles is configured to allow the hypodermic needle to be mated to the cartridge at the time of manufacture rather than the more common convention of mating the needle to the syringe at the time of use. In certain embodiments, an aspect of the present disclosure can incorporate features in the cartridge and/or the needle to ensure retention of the needle during manufacture, distribution, handling, and use as well as features to ensure that proper mating of the reservoir or vessel to the needle prior to the use. In some embodiments, such features can minimize the risks of leakage of the agent from the reservoir or the reservoir orifice interface due to breakage or improper mating.

In certain embodiments, the cartridge can include a tissue contact interface located at the distal end of the subassembly. In certain embodiments, the tissue contact interface comprises a substantially planar structure oriented perpendicular to the elongate orientation of the electrodes and having one or more apertures configured to allow passage of the electrodes through the tissue contact interface. For embodiments incorporating an integrated reservoir or vessel and injection orifice, the interface also has apertures to accommodate injection orifice or needle free injection. To minimize the risk of contamination of the electrodes and injection needle as well as the occurrence of unintended sharps exposure to the user or recipient, in a certain embodiment, the apertures accommodating passage of the electrodes and injection needle are of a size suitable to prevent accidental contact with the electrodes and injection needle. Most commonly, the tissue contact interface is comprised of one or more plastics suitable for at least short term tissue contact.

To avoid potential cross contamination of biological material between recipients, the cartridge assembly 100 can be configured for single use. In some cases, the cartridge includes one or more mechanical, electrical, and/or identification elements which restrict use of the cartridge to a single administration. Examples of mechanical elements of this nature include for instance, but are not restricted to, lockouts and/or detents which secure the electrode mount structure and/or the stick shield (see below) in the deployed state after use. Examples of electrical elements include for instance, fuses or links configured in series with one or more electrodes which are deactivated by the source of electrical energy at the conclusion of the first use of the cartridge. Examples of identification elements include, for instance, serialized radio frequency identification devices, bar codes, or quick response codes configured to be read by the applicator and/or the source of electrical energy. The identification information for a specific cartridge can then be used to prevent accidental or intentional re-use of that cartridge by the applicator and/or the source of energy. In an embodiment, one or more redundant features are incorporated to minimize the potential for re-use of the cartridges.

In an embodiment of an apparatus described herein, as shown in FIG. 2, the applicator 400 comprises a support structure configured to interface with the cartridge assembly 100, a user interface 410-418 (FIG. 13B), electrically conductive electrical connections configured to provide operative connection between the conductive contact region located on the distal region of the elongate electrodes and the source of electrical energy when the electrodes are deployed into the target tissue of the recipient. In some cases, the user interface comprises a handle, one or more display features designed to convey information to the user, and one or more features capable of accepting user input. In certain embodiments, the display features are configured to convey the operating status of the device during its set up and use as well as relevant warning/error messages. Such displays can comprise mechanical features, lights, alphanumeric displays, and/or electronic display screens. In some cases, the features capable of accepting user input are configured to allow the user, at the appropriate stage of the procedure, to de-activate safety features within the device preventing accidental discharge, make selections regarding particular parameters of the procedure (e.g., the intended depth of injection), and to initiate procedure administration and can include buttons, triggers, mechanical slides, and/or levers.

In certain embodiments, the applicator 400 also includes actuation mechanisms which interface with the cartridge assembly and which are configured for transcutaneous deployment of the electrodes, positioning of the injection orifice relative to the target tissues, discharge of the agent of interest from the reservoir or vessel through the orifice and into the target tissue site, and/or conveying electrical signals from an electric field generator such as a controller 700 to the cartridge 100. The applicator 400 can be configured such that the energy to actuate the mechanisms is supplied by the user, or more preferably, the apparatus may incorporate one or more inanimate sources of energy operatively connected to the actuation mechanisms within the applicator. Such inanimate sources of energy include for instance, electromechanical devices (solenoids, motors, lead screws), mechanical components (springs and related devices), and compressed gases.

An exemplary implementation of a cartridge assembly 100 is as described in FIG. 3A, a cartridge assembly 100 includes a reservoir or vessel loading port 140 and a reservoir or vessel containment volume 142 to receive and contain a reservoir or vessel 101 of a medicament. A cartridge assembly 100 is required because, for a device in which an electrical field is to be generated and used as part of a therapy, an electric field generator such as a controller 700 is required to electrically interface with the device containing the electrodes configured to contact the target tissue. As the controller can be configured for multiple uses, and the reservoir or vessel 101 can be intended for single use, the cartridge assembly 100 can be present to hold the electrodes 122 and, the reservoir or vessel 101, to interface with the re-usable device, and for the cartridge assembly 100 to be configured for single use. Thus, the applicator 400 can be a reusable component and the cartridge assembly 100 can be configured for single use. The cartridge assembly 100 can also be rendered in a condition to prevent subsequent use if errors or tampering occur in the insertion of a reservoir or vessel 101, or if defects are present.

The term reservoir or vessel 101 can refer to a syringe, vial, or any other device which can contain a medicament or therapeutic agent and which can interface with a device having an orifice, such as a needle, shown in FIG. 4 as a needle 105 having a needle hub 152. The reservoir 101, for a given type of cartridge assembly 100, generally has a common shape and size. Various components within the cartridge assembly 100 allow for a leeway in exact sizing and/or manufacturing tolerances, but generally a common shape and size are required to reduce the risk that drugs not labeled for use with cartridge 100 are erroneously delivered with the device. If an appropriately sized reservoir 101 is not provided by the user, one or more interlocks within the cartridge assembly 100 may be unable to deactivate, and the system may be rendered unusable until a proper-sized reservoir 101 is inserted.

As seen in FIG. 3B, the reservoir 101 generally can be equipped with a plunger and a port 156 for drug egress. A removable cap 158 can also be provided to maintain the sterility and integrity of the agent until such time as the reservoir is to be inserted and used. The port for drug egress can be proximal to the needle hub 152 in use, and the plunger can be opposite this port for drug egress. As an alternative to an open port for drug egress, in some embodiments, the reservoir or vessel can be configured with a septum component which covers and seals the end of the container opposite the plunger. The septum can be made of elastomeric compounds such as silicone or butyl rubber, with the specific formulation and coating of the material selected for stability and compatibility with the agent contained within the reservoir or vessel. The septum component is typically held in place by a crimp seal or other fastening mechanism. This septum seal configuration obviates the need for a removable cap, but requires that needle 105 be equipped with a suitable piercing member such as a needle, spike, or other features to access the fluid contained in the reservoir or vessel. Specific implementations for this configuration include dual sided needle configurations and spike vial adapters.

The cartridge assembly 100 is not only configured for receiving the reservoir or vessel 101 but also for being received by an applicator 400 in an applicator cartridge assembly receiving port 401 (FIG. 2). Thus, the cartridge assembly 100 includes a device allowing the applicator 400 to pull and retain the same within an interior volume, at least partially. In certain embodiments, the device is one or more racks on the surface(s) of the cartridge assembly 100 that engage a corresponding motorized pinion assembly in the applicator 400. In other implementations, the applicator 400 can interface with the cartridge assembly 100 without the need to pull the same into an interior volume. In yet other implementations, other techniques may be employed to cause the cartridge assembly 100 to engage the applicator 400, e.g., motorized tracks or brackets and the like onto which the cartridge assembly 100 can interface.

The applicator 400 is further provided with interface elements allowing the same to control certain actions within the cartridge assembly 100. In particular, the applicator 400 can be configured to control needle insertion, medicament delivery, electrode insertion, and electrode activation using various subsystems. In some cases these steps are linked, so that a single action of applicator 400 initiates multiple of these steps. In some implementations, all of these steps but the medicament delivery and electrode activation are caused by a single action, as described in the exemplary implementation below.

Upon appropriate activation, such as the use of electrical or optical signals conveyed to mechanical, electrical, or optical elements of the cartridge assembly 100, the applicator 400 can be enabled to test subsystems within the cartridge assembly 100, ensuring that the same are operating properly and are properly configured for medicament delivery with electric field application. For example, such subsystems include that the applicator 400 can test to ensure that the cartridge assembly 100 has not been previously used, that the reservoir or vessel has been properly placed within the cartridge assembly, that appropriate force applied against the body of a subject as applied through an alignment guide/splay shield 108, a test that a depth has been affirmatively selected by the user, and that an exterior cartridge cap 110 has been removed. Moreover, the applicator 400 can be configured to monitor the status of the cartridge functions during execution of the procedure. For example, such subsystems include that the applicator 400 can test to ensure that that electrodes 122 are properly deployed within a subject prior to commencing with administration of the medicament, that the plunger in the reservoir or vessel has been appropriately actuated prior to application of the electrical fields, that the user has maintained appropriate force applied against the body of the subject during the administration procedure, and so on.

In addition to the subsystems that are operated by the applicator 400, the cartridge assembly 100 can incorporate appropriate subsystems, including those that interact with the applicator 400 and those that do not so interact, so as to accomplish the goals of the medicament delivery and electric field application therapy. These include a subsystem for causing needle and electrode insertion, a subsystem for protecting users from sharps following therapy administration, a subsystem for providing different depths of needle/electrodes insertion, a subsystem for ensuring that adequate force has been applied against the tissue of the recipient prior to allowing initiation of the procedure and subsequently during application of the administration procedure and so on. While often described in the context of deployable needles and electrodes, it is noted here that such are not strictly required, and that systems with non-deployable or fixed needles and electrodes also benefits from systems and methods according to present principles, including the subsystems described.

In one exemplary implementation, as shown in FIG. 4, the cartridge assembly 100 includes an outer cartridge 102, in some cases termed a housing. The outer cartridge 102 is terminated at a distal end by an outer cartridge cap 106. The outer cartridge 102 includes an inner cartridge containment volume 150, for receiving an inner cartridge 103, which is received and moves in a slidable manner in relationship to the outer cartridge 102. The inner cartridge 103 includes a reservoir or vessel containment volume 142 in which the reservoir or vessel 101 may be situated. The inner cartridge 103 engages with an inner cartridge cap 104 at a distal end. The inner cartridge cap 104 has a number of functions, including to lock electrodes 122 in place (the inner cartridge 103 itself has seams that the electrodes 122 are placed into) and to provide a bearing surface for a stick shield 134. The inner cartridge cap 104 locks onto the inner cartridge 103.

A cartridge breech 112 is received in a portion of the reservoir or vessel containment volume 142 in the inner cartridge 103, in a portion opposite that of the inner cartridge cap 104. A vessel detection cap 118 engages the cartridge breech 112 through a vessel detection spring 116. A cartridge lock ring 114 locks the system in place, including the cartridge breech 112 to the inner cartridge 103. The vessel detection spring 116 also serves to push the reservoir 101 into engagement with the needle hub 152, and also serves to accommodate tolerances in the size of reservoir 101.

A vessel interlock 120 provides a mechanical interlock to prevent inadvertent or unwanted actuation of cartridge functions. In particular, the vessel interlock 120, also termed a first reservoir insertion trigger, is placed below the inner cartridge 103 and has fingers 121 that extend through slots or holes defined in the inner cartridge 103 (see FIG. 5B). The fingers 121 prevent the cartridge breech 112 from slidably moving relative to the inner cartridge 103, and in particular from moving within the inner cartridge 103 towards the inner cartridge cap 104 before a reservoir has been inserted into a vessel containment volume 142.

When a reservoir or vessel 101 is properly inserted in the reservoir or vessel containment volume 142, the reservoir or vessel interlock 120 is pushed down and the fingers 121 are pushed down, no longer extending into the vessel containment volume 142. This pushing down or depression of the vessel interlock 120 may also be configured to provide an audible, tactile, or haptic "click" that can inform the user of proper insertion. Once depressed, the cartridge breech 112, no longer blocked by the fingers 121 of reservoir or vessel interlock 120, is then permitted to move, and in particular is permitted to move in the direction towards the inner cartridge cap 104.

The cartridge breech 112 is caused to move such by the action of the spring cap/cartridge interface 470 when the cartridge assembly 100 is inserted in the applicator 400 in a fashion described below. When the cartridge breech 112 moves far enough forward, it locks in place, securing the reservoir or vessel 101 in the reservoir or vessel containment volume 142 and ensuring that it is properly positioned relative to the needle hub 152 to ensure an intact fluid pathway from the reservoir 101 to the orifice of needle 105.

For embodiments of the device where the injection needle is incorporated into the cartridge 100, the use of standard "off the shelf" single use hypodermic injection needles may be employed within the device. However, the operational and reliability characteristics of the device may be improved through the incorporation of customized design elements that are not present in hypodermic needles intended for conventional parenteral administration procedures. Specific aspects of the needle hub 152 can include the material from which it is comprised, the inclusion of retention features to prevent the needle hub 152 from becoming dislodged from inner cartridge 103 during distribution and use, and the orientation of any bevel features in the needle relative to the hub.

Conventional single use disposable injection needles are commonly comprised of injection molded polypropylene thermoplastic. However, for many applications, the impact strength, tensile strength, and flexural strength of polypropylene may not be adequate to ensure integrity of the hub when subjected to the forces characteristic of needle deployment and injection with this device. Specific failures of concern include failure in the hub wall due to impact or injection forces as well as failure of the hub needle joint due to same. While adjustments in the design of the hub, including its geometry and wall thickness may be utilized to address prevent these failures, it is not always feasible to modify the design sufficiently to prevent hub failure while ensuring that the hub retains the dimensional properties required for proper mating to a conical male luer slip connectors as described in the relevant standard published by the International Standards Organization (ISO) ISO 80369-7:2016 Small-bore connectors for liquids and gases in healthcare applications—Part 7: Connectors for intravascular or hypodermic application. Specifically, given the forces that the syringe needle and hub are subjected to during deployment, in certain embodiments, a material with improved impact strength, tensile strength, and flexural strength is used. One example is the use of injection molded polycarbonate plastics (such as ZELUX® GS, Makrolon, or Lexan) or copolyesters (such as Eastman Tritan™ Copolyester MX731, MX711, and MX 730). When assessed according to ISO 180:2000 Plastics—Determination of Izod impact strength, a notched impact strength of at least 70 kJ/m2 is considered suitable for this application. When assessed according to the ISO 527-1:2012 Plastics—Determination of tensile properties—Part 1: General principles, a tensile strength of at least 30 MPa is considered suitable for this application. When assessed according to ISO 178:2010 Plastics—Determination of flexural properties, a flexural strength of at least 50 MPa is considered suitable for this application. In some embodiments, the specific resin selected exhibits compatibility with the intended method of sterilization (e.g., gamma radiation) without exhibiting detrimental changes in its physical properties that could compromise its function.

For embodiments where a custom injection needle is utilized, one or more mechanical features are included which are not ordinarily present on conventional syringe hubs that enable the device to be inserted into inner cartridge 103. Such features can include tabs, snaps, or ridges with corresponding mechanical features located on inner cartridge 103. In some cases, the features are implemented such that the hub mates with the inner cartridge 103 in a consistent orientation. Combined with a needle manufacturing process that is capable of consistently orienting the bevel or other needle orifice feature, this insures that biases in injection location or medicament distribution due to the location and design of the orifice can be accounted for in the design of the device. For example, needles with asymmetrical penetrating tip features (e.g., a bevel cut) can exhibit a directional bias during deployment into tissue due to interaction between the tissue and the asymmetrical penetration feature on the needle. If the electrodes have a symmetrical penetrating tip feature (e.g., a trocar tip) then the electrodes would not exhibit a corresponding bias in their deployment characteristics. Therefore, mounting feature for needle hub 152 on inner cartridge 103 can include an offset in the position of the injection orifice on needle 105 relative the electrodes 122 prior to deployment to account for the expected deployment characteristics of the asymmetrical bevel of the needle. The precise dimension of the offset can depend on the nature of the target tissue and the expected range of penetration depths, but in certain embodiments the needle is offset by 0.5-1 mm for each 10 mm of penetration depth. When using electrodes and injection needles with differing tip profiles or where the tip profiles must be consistently oriented with one another, such features are advantageous for insuring co-localization of the medicament distribution with the application of the electrical fields.

The incorporation of a syringe detection cap 118 mounted to a syringe detection spring 116 ensures that the cartridge assembly 100 can accept and properly position the syringe 101 relative to needle hub 152 across the range of manufacturing tolerances expected for syringe 101. The applicator 400 causes the cartridge breech 112 to move forward during the loading procedure when the spring cap/cartridge interface 470 within the applicator 400 moves distally, relative to the cartridge assembly 100. This action occurs when the cartridge assembly 100 is loaded into the applicator 400 and the cartridge assembly 100 is pulled into the applicator 400, e.g., by the action of a loading mechanism, e.g., a rack-and-pinion mechanism described below.

Figure 5C:
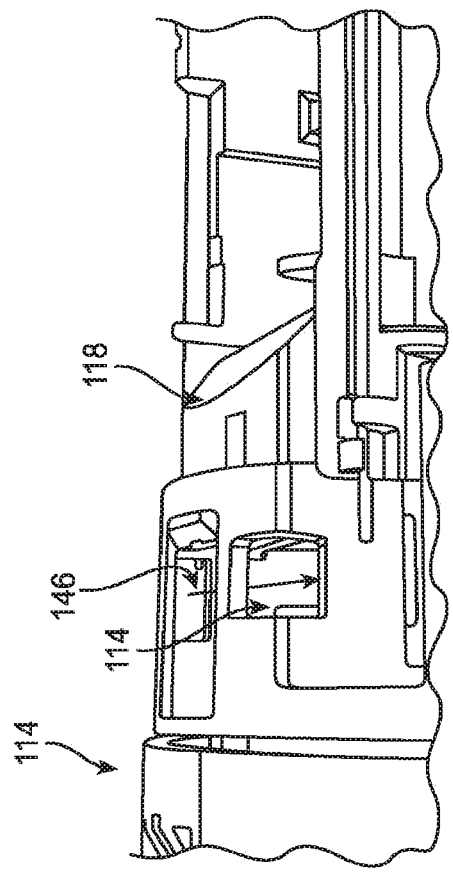
FIGS. 5A-5E show views of aspects of an inner cartridge and cartridge breech in a device described herein.
Figure 5D:
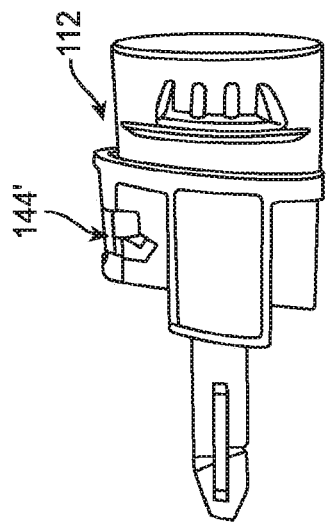
Figure 5A:
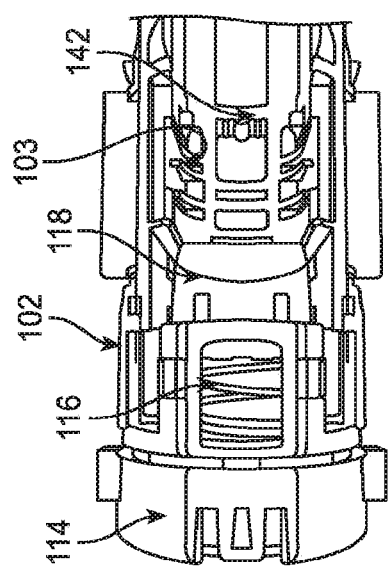
Figure 5B:
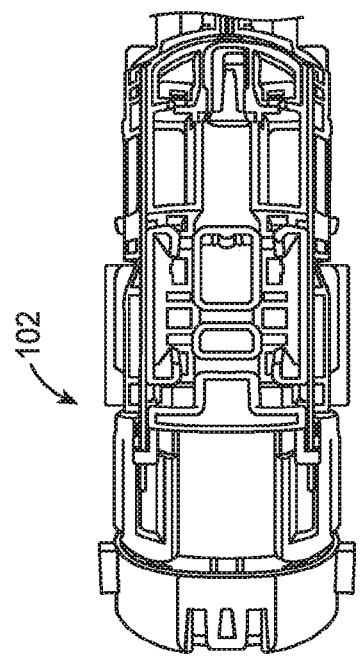
Figure 5E:
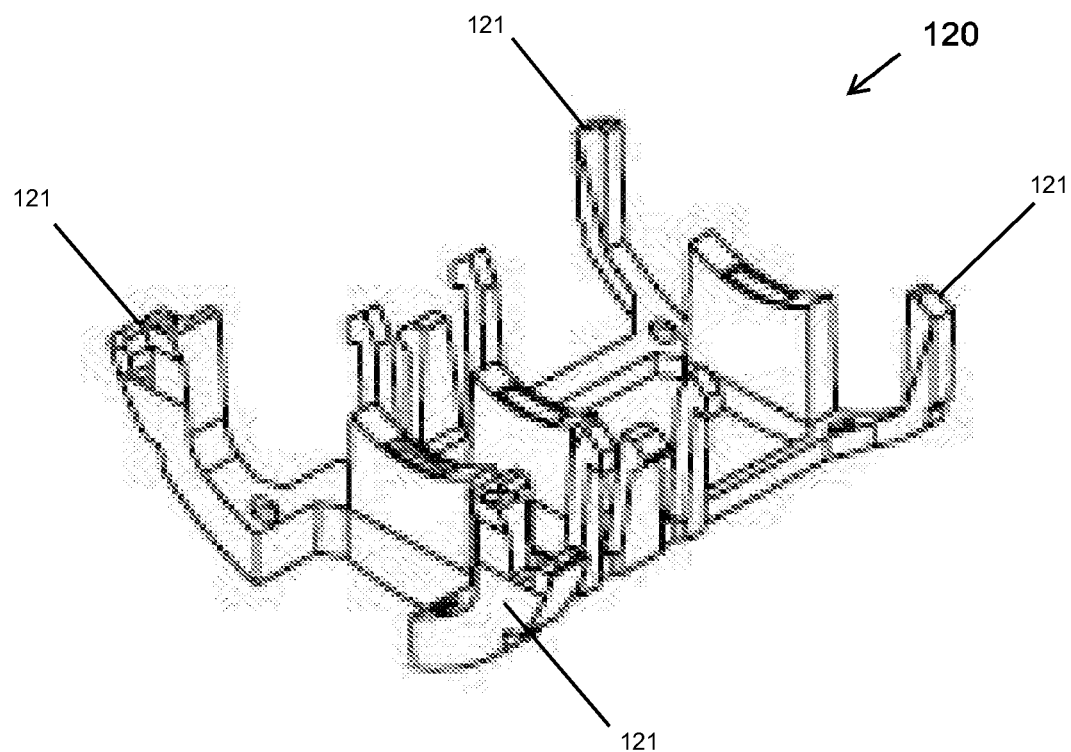
Figure 6:
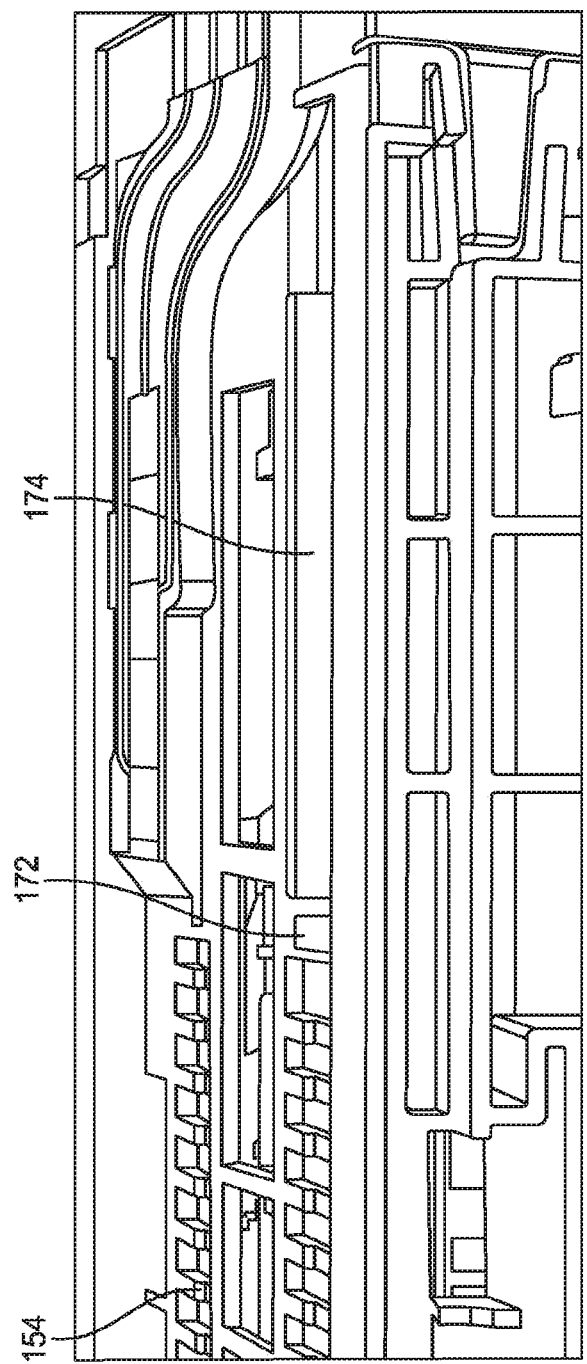
FIG. 6 illustrates details of a cartridge assembly showing a rack 154, a initiating flag 172, and a continuing flag 174 according to present principles.

The movement of the cartridge breech 112 can act as a second interlock. In particular, in one implementation, as seen in FIGS. 5C-5D, a line of sight is visible and detectable, by an appropriately configured sensor, within the cartridge assembly receiving volume 403, through a set of reservoir or vessel locking holes 144' (FIG. 5D). This line of sight is visible when the cartridge assembly 100 is loaded into the applicator 400. The visible light of sight, or occlusion of the same, can act as part of a second interlock that must be deactivated for the controller 700 to allow activation and triggering of the device, including needle and electrode insertion, medicament delivery, and electrode activation.

For example, in one implementation, the reservoir or vessel locking holes 144' (FIG. 5D) must be occluded for the device to operate. If a visible line of sight is present, e.g., as detected by an IR or visible light emitter and detector paired within the cartridge assembly receiving volume 403 of the applicator, the device may be rendered inoperable and generate and display an error message on the applicator display 404 and/or controller 700, including the controller display 712, to notify the user of the state of the device as well as the recommended steps to be performed to address the error.

Thus, in this implementation, one error state can be that no reservoir 101 was loaded into the cartridge 100 or that the syringe was not properly seated into the inner cartridge 103. In this case, the vessel interlock 120 cannot be depressed as there is no reservoir 101 to perform this action. In this case, the cartridge breech 112 cannot be moved forward, in the distal direction, towards the inner cartridge cap 104. The construction of these components can be such that an open breech state results in an open line of sight 146 through first reservoir locking holes 144' (FIG. 5D). An ancillary check is that the cartridge breech 112 cannot be closed, and this can manifest itself as an inability of the cartridge to move the required distance backward or distally into the cartridge assembly receiving volume 403. As these conditions are defined by the system to be an error state, the same can be identified and used in the generation of an error message, e.g., with an appropriate message to the user on a user interface on the applicator display 404 and/or controller 700, including the controller display 712. A similar error state may occur if the reservoir 101 is improperly loaded, or if the vessel interlock 120 is damaged. Generally in this case, an appropriate error message may be accompanied by instructions to the user to remove the cartridge, reinstall a new reservoir, and attempt to reintroduce the cartridge assembly 100 into the applicator 400.

Another error state may be that the cartridge breech 112 is moved forward manually by the user without a reservoir 101 present, such occurring by the user manually pushing the vessel interlock 120 out of the vessel containment volume 142. This situation can also be defined as an error state, and the same can be detected because another (second)

set of reservoir locking holes 144 (FIG. 5C) are placed on a portion of the outer cartridge 102. If no reservoir is in place, but the cartridge breech 112 is moved forward by the action of the vessel interlock 120 being depressed, then the reservoir locking holes 144' (FIG. 5D) align with the reservoir locking holes 144 (FIG. 5C), again creating an open line of sight 146 and a subsequent error state. This error state may also occur if the reservoir or vessel interlock 120 is damaged and its fingers are no longer within the vessel containment volume 142. In a certain embodiment, this error state need not be not remediable by attempting to reinstall a reservoir, as a reservoir may not fit in the vessel containment volume 142 with the cartridge breech 112 locked. In a certain embodiemnt, a new cartridge assembly 100 is required.

In contrast, if an appropriately sized reservoir or vessel 101 is positioned properly in place, then the vessel detection cap 118 is pushed back against the vessel detection spring 116, and the movement of the vessel detection cap 118 occludes the reservoir locking holes 144 (FIG. 5C) and the reservoir locking holes 144' (FIG. 5D). In this case there is no error state, allowing the device to operate. The occlusion, and detection of the occlusion, occurs within the body of the applicator 400, after the cartridge assembly 100 is inserted, and thus is insusceptible to user attempts to defeat this interlock, whether intentional, accidental, or caused by a defect. It is noted that this "no error" state still occurs even if the user intentionally or inadvertently closes the cartridge breech 112 themselves during handling of the cartridge 100.

Depending on which error state occurs, the cartridge assembly 100 can remain usable or not. If the cartridge breech 112 has been locked into place, the cartridge assembly 100 is rendered unusable. If, however, the cartridge breech 112 has not been locked into place, then the cartridge assembly 100 can be removed from the applicator 400 and a new reservoir 101 inserted.

While the above-noted set of two interlocks (one mechanical using vessel interlock 120 and one using a light emitter and collector and reservoir or vessel lockout holes 144 and 144') have been found particularly useful in some implementations, it is to be understood that other types of interlocks can also be employed (FIGS. 5C-5D). For example, instead of having an error state occur when the reservoir locking holes 144 are not occluded, the error state may be configured to occur (via a change in reservoir locking hole location and program logic) when the reservoir locking holes 144 are occluded (and the clear line of sight 146 then corresponding to the non-error state). The vessel interlock 120 can incorporate additional mechanical flag features that are recessed in the cartridge when the interlock is active, but become visible to an appropriately configured sensor when the syringe 101 has been properly inserted and the vessel interlock 120 is depressed into its released position. In other variations, other ways may be employed to determine if a line of sight is present, e.g., optical, acoustic, electrical, or the like, so long as a suitable emitter and collector can be positioned within the applicator 400. Other ways may also be employed to determine if the reservoir or vessel 101 is properly loaded, e.g., mechanical techniques, as it is to be understood by one of ordinary skill in the art given this teaching. Depending on implementation, if an error state is detected, the applicator 400 may be prevented from operating either with the cartridge assembly 100 in place, or the applicator 400 may be prevented from even accepting the cartridge assembly 100 in the first place. For example, the cartridge can be designed such that the vessel interlock 120 includes mechanical tab or locking features which extend from one or more of the cartridge surfaces until an appropriate vessel, such as syringe 101 is properly inserted into the cartridge 100, thus preventing inappropriate vessels from being used and improper positioning of proper vessels. The mechanical tabs are designed to interact with a corresponding detent feature located in the applicator 400 such that loading of the cartridge 100 into the applicator 400 is physically blocked unless the vessel interlock 120 is released—i.e. unless the tab is deflected or moved aside by a properly loaded vessel. This mechanical interaction would provide feedback to the user or the system that an error condition must be resolved before proceeding with the loading of the cartridge 100 into applicator 400. In other variations, more or less than two interlocks may be provided, although the same may be correspondingly associated with a different safety profile.

In certain implementations, other features can also be employed in the above determinations, or to enhance the above determinations. For example, where a motor is employed to pull the cartridge assembly 100 into the applicator 400, sensors may be employed as described below to detect the spatial position of the cartridge assembly 100 during the insertion process. Put another way, the applicator 400 may detect where the cartridge assembly 100 is within the cartridge assembly receiving volume 403. In some cases, such may allow determination of additional error states either directly, or by prompting the activation of additional sensors to assess the state of the device. For example, in a used cartridge, the cartridge breech 112 is locked into position. If the used cartridge assembly 100 is attempted to be re-used, the optical detector detects the cartridge assembly 100 at a different point than it would for an unused cartridge assembly 100. The use of an electrical motor for one or more system functions also provides the opportunity to monitor its operational status including the voltage and current levels supplied to the motor as well as the number of revolutions that the motor has performed during a specific operation. Measurement of these quantities during system operation can be used as a primary or secondary method for detecting potential or actual fault conditions. For example, the use of mechanical interlocks designed to block the loading procedure when the cartridge 100 is not properly configured can be coupled with sensors and logical circuits monitoring the motor to ensure proper loading of the cartridge 100 into applicator 400. For example, the interaction of the mechanical features described above that are designed to prevent the loading of cartridge 100 without a properly inserted reservoir or vessel 102 would result in increased load on the motor drive mechanism, resulting in a higher current draw. Detection of the elevated current draw by the motor would prompt the loading procedure to be halted and a fault condition displayed to the user, for example on stimulator display 712 and/or applicator display 404.

Since it is possible that medicaments not intended for administration by this method could be contained within reservoirs of similar size and configuration as that intended for use by this delivery method. Therefore, an additional aspect of the system is the incorporation of one or more methods to ensure that the reservoir or vessel 101 inserted into the cartridge 100 by the user is specifically, intended for use with the device. The implementation of such features would reduce the risk that an incorrect medicament is administered to a given subject. Customarily, specific information in the user instructions and labeling of the medicament includes the route and method of administration. However, to further reduce the potential for user errors, the incorporation of mechanical, optical, and/or electrical features within the reservoir or vessel and device may be desirable. In one embodiment the syringe may be designed to incorporate one or more unique mechanical features that are not present in other reservoirs which may be similar to those designed for use with this delivery method. For example, the reservoir or vessel may be specified to incorporate a rib or other elongate feature on the flange or barrel of the reservoir. In this embodiment, a corresponding mating feature would be included on the vessel interlock 120 such that the vessel interlock would be deactivated only if a reservoir with the appropriate mating feature were properly inserted into the device. In the event that it is not feasible to directly implement the feature in the design of the reservoir, an alternative embodiment would include the placement of a secondary mechanical component on the reservoir that would be unique to reservoirs intended for use with the device. For example, a ring or other appropriately configured feature designed to slide over the barrel of the reservoir may be used to "key" the reservoir for use with the device by mating with a corresponding feature in the outer cartridge 102, inner cartridge 103, vessel interlock 120, vessel detection cap 118, or other suitable feature within the cartridge 100. An additional embodiment a custom label of suitable size, color, and/or electrical conductivity applied to a predetermined location on the outer surface of reservoirs that are intended for use with the device. Corresponding optical or electrical sensors in applicator 400 would be configured to assess the presence or absence of the label on the surface of the reservoir in order to verify that the medicament inserted into the cartridge is intended for use with the device. The detection method would comprise the use of optical or electrical signals applied to the surface of the label in order to assess its presence or absence. In this way, reservoirs containing medicaments not intended for use with the device (and therefore missing the relevant label) could be detected and excluded from potential misuse.

A configuration of sensors is now described to perform the cartridge loading and syringe detection determination described above, such sensors further forming a portion of a cartridge loading subassembly within the application 400. In more detail, and referring in addition to FIGS. 6, 17B, and 18C, an exemplary way of detecting where the cartridge assembly 100 is located is by use of a cartridge loading sensor 436 and a cartridge loaded sensor 438, which forms a portion of a loading drive subassembly 454, the subassembly 454 further including cartridge guide rails 442 and a loading motor 444 which has a connection to a pinion gear assembly 448 that pulls the cartridge assembly 100 into the cartridge assembly receiving volume 403 via racks 154 on the base of the outer cartridge 102. In more detail, when the cartridge loading sensor 436 detects an initiating flag 172 on the cartridge assembly 100 (see FIG. 6), the motor may be caused to initiate loading. When the cartridge loaded sensor 438 detects the same flag, loading may be caused to cease. A continuing flag 174 may be employed that is required to be present for loading to continue.

The first "teeth" of the rack 154 can be configured to provide a tactile sensation (or audible or haptic) for the user when they are inserting the cartridge assembly 100 into the cartridge assembly receiving volume 403. Such configuration may include the shape and/or size of the rack teeth 154 as well as the amount of flexion permitted by their positioning in the outer cartridge. By adapting the rack teeth implementation, the desired degree of tactile feedback can be achieved while ensuring that it does not provide a significant force against the loading motor 444 from receiving and loading the cartridge assembly 100.

Referring in addition to FIG. 17A, and as noted above, the cartridge assembly 100 is inserted into a cartridge assembly receiving volume 403 within the applicator 400. While various ways may be employed to perform this insertion, one way that has been found particularly useful is by way of a pinion gear assembly 448 engaging racks 154 on the outer cartridge 102. The use of more than one rack provides additional stability, particularly torsional stability during the loading phase. Referring also to the insertion/injection drive assembly 456 of FIG. 18A, in addition to drawing the cartridge assembly 100 within the cartridge assembly receiving volume 403, the insertion action further compresses an electrode/needle insertion spring 472 through a spring cap/cartridge interface 470. The electrode/needle insertion spring 472 is used as the primary driving force for the needle and electrode insertion during medicament delivery.

This hybrid motor/spring action provides numerous benefits. The motor drive is beneficial as it is highly controllable and allows the cartridge 100 to be loaded into the applicator 400 in a semi-automated fashion with minimal input of mechanical force required by the user. As described above, the implementation of motor drive based mechanisms provides monitoring of the operational status of the system. For instance, conveying the current draw and revolution count to the logical and control circuitry in the system provides a supplementary method for detection and diagnosis of potential fault conditions. Despite these advantages, in certain cases electric motors can be poorly adapted to exerting the necessary linear force over sufficiently brief time scales that is most desirable for effective transcutaneous deployment of arrays comprising a plurality of elongate electrodes and, in selected embodiments, hypodermic injection needles. In particular, the penetration of dermal tissues is most consistently achieved by the application of a large linear force over a brief time scale. In some embodiments, the most favorable insertion characteristics are achieved when the penetrating electrodes, and when present, injection needle contact the skin at higher velocity. This is because sharps travelling at increased velocity at the point of skin contact result in less tissue deformation as they cut or penetrate the tissue. Therefore, in some embodiments, rapidly accelerating the sharps prior to contact with the skin is desired. In some embodiments, multiple electrodes and an injection needle are frequently utilized. In another embodiment, the velocity of the electrodes is at least 50 mm/second prior to contact with the skin. In yet another embodiment, the velocity of the electrode is at least 500 mm/second prior to contact with the skin. This deployment approach minimizes the discomfort perceived by the subject during the electrode penetration and is most favorable for maintaining a consistent spatial relationship between the plurality of electrodes. In contrast to electromechanical motors, spring driven mechanisms exhibit a more favorable discharge profile that is capable of imparting the rapid impulse force to the electrodes and injection needle that is desirable for transcutaneous electrode implantation. In particular, the force exerted by a compression spring is at its peak at initial discharge. This is favorable for transcutaneous deployment where a high velocity at the point of skin contact is favorable and, due to the viscoelasticity of skin tissue, the greatest force is required for penetration of the skin, particularly when contacting the skin with a plurality of electrodes and/or injection needles. In addition, a spring based mechanism is capable of generating this force from a simple, durable, and compact form factor that can be readily integrated into a handheld device format. However, a disadvantage of spring based mechanisms is that they typically require the input of substantial mechanical force by the user in order to prime them for operation, especially for springs with high force constants and/or large displacements. The use of a hybrid motor and spring mechanism, as described in the present disclosure, achieves the desired deployment force characteristics while being simple for the user to operate. While the hybrid motor and spring mechanism is a preferred embodiment, depending on implementation, other hybrid mechanisms incorporating two or more drive mechanisms wherein one is capable of generating a rapid impulse force and the other is capable of priming the impulse force mechanism, e.g., a pump capable of compressing gas into a chamber and then discharging the compressed gas in order to apply an impulse force for deployment of the electrodes and, where applicable, hypodermic needle(s).

In any case, once loaded, the desired depth electrode deployment and/or agent administration is affirmatively selected by the physician or other medicament administrator and the same transmitted to the applicator 400. Referring in addition to FIG. 13B, the depth may be selected by depth selection buttons 409 (or other equivalent interface such as a toggle switch or sliding switch) and the result displayed on injection depth selection indicators 408 (or, again, other equivalent interface). The available injection depths are conveyed to the user by appropriate labeling of the applicator 400 and/or the cartridge 100. In some embodiments, any labeling regarding the injection depth is located on the cartridge 100 and remains visible to the user following installation in the applicator 400. For example, the available injection depths may be labeled on the upper surface of the alignment guide/splay shield 108. In order to avoid circumstances in which the user forgets or neglects to select a depth of injection, it is preferable that the device does not allow the user to proceed with the administration procedure until such affirmative selection is made. This can be accomplished by the implementation of appropriate control logic within the system such that subsequent elements of the device set up or usage are not accessible until a valid depth selection has been entered by the user. In certain embodiments, when the user is prompted to affirmatively select the injection depth, the controller display may convey to the user information regarding the proper methods for assessing the subject and determining the appropriate injection depth for the selected administration site.

Referring in addition to FIGS. 18A-18B, upon proper cartridge assembly insertion, the spring cap/cartridge interface 470 engages and also presses against the spring cover hole 471 and tabs 491. While a large spring force presses against the inner cartridge 103, the same is prevented from moving forward by engagement of a set of retaining posts 488 against walls 494 of the outer cartridge 102. However, the force exerted by 470 splays apart tabs 491 (which prevent inadvertent rotation of the lock ring during handling) thereby allowing rotation of the cartridge lock ring 114 by the motor drive mechanism. The rotation of the cartridge lock ring 114 causes rotation of the retaining posts 488. The retaining posts 488 can be rotated into either the channels for first depth 490 or the channels for second depth 492. The length of the channels for first depth 490 correspond to one of the choices of depths, and the length of the channels for second depth 492 corresponds to the other, with one or the other depths being selected by the user using buttons 409. For example, the length of channels 490 may be in the range of 20-30 mm and the length of the channels 492 may be in the range of 12-20 mm. The requirement of a user to affirmatively select a depth provides yet another interlock. Without an affirmative selection, the applicator may not allow activation/needle insertion. The rotation of the cartridge lock ring 114 is thus caused by a clockwise or a counterclockwise rotation directed by the applicator 400 according to the dictates of the user. Requiring rotational motion of a set of posts into such channels to achieve deployment of the electrodes and, if present, injection needle greatly reduces the chances for accidental discharge, even upon violent jarring or falling.

In more detail, the rotation of the cartridge lock ring 114 is transmitted to the cartridge assembly 100 by the retaining posts 488, which are disposed upon proper cartridge assembly 100 insertion into slots on an insertion mechanism gear drive ring 478. In FIG. 18A, the slots on the insertion mechanism gear drive ring 478 are disposed at 3 o'clock and 9 o'clock positions. The insertion mechanism gear drive ring 478 is mounted to a partial insertion gear ring 479, which is driven by an insertion mechanism drive motor 482. Driving the partial insertion gear ring 479 causes the insertion mechanism gear drive ring 478 to rotate either clockwise or counter-clockwise. A flag 481 on a ring 480 and accompanying insertion mechanism position sensor 483 are employed to determine the position of the insertion mechanism gear drive ring 478, and is further used to accurately return the same to the 3 o'clock and 9 o'clock positions when the applicator 400 is to be re-used with another cartridge.

The above implementation provides various advantages. For example, the user has to actively perform a step of selecting the depth before proceeding with the administration procedure. In so doing, the user has to assess the proper depth of injection for the selected injection site and prepare the site as noted in a guide or instructions for use document. As noted, the insertion mechanism, requiring rotational motion to deploy, is significantly hardened against accidental deployment due to falling, dropping, jarring, and so on.

Variations are be understood by a person skilled in the art. For example, while two channels and two retaining posts are employed for each depth, one channel and one retaining post may also be used. Various types of motors and mechanisms may be employed for conveying the rotational motion necessary to rotate the posts into the channels. Other variations are also to be understood, including the use of solenoids and the like. In lieu of the use of channels, motor driven deployment may be used to provide variable depths, which depths may be controlled simply by how far the motor is controlled to drive the deployment. Preferably, in this context, the hybrid drive mechanism described would be configured such that the impulse discharge mechanism (e.g., the spring) is used for initial deployment through the dermis and then the motor drive mechanism is used to advance the electrodes to their desired depth.

One or more interlocks may be in place which must be deactivated before the insertion mechanism gear drive ring 478 is caused to rotate, rotating retaining posts 488 into the channels.

First, a force detection interlock subsystem may be in place that requires the device to be applied to the subject at a force of greater than a predetermined amount prior to allowing the administration procedure to be initiated. This force may be measured by an appropriate mechanical or electromechanical system and the result fed back into the controller 700 and used as an interlock to prevent activation of the device where insufficient force is provided. In some embodiments, the controller 700 is capable of conveying the state of the force detection interlock to the user through visual, haptic, or auditory signals so that a state of inadequate force can be corrected and the user may proceed with administration. In the event that the user attempts to proceed with the administration in a state of inadequate force contact (e.g., by depressing a trigger 407 or other activation button), additional visual, haptic, or auditory signals may be provided by the applicator 400 or controller 700 to notify the user that the interlock must be deactivated prior to proceeding with administration.

The detection of the force applied to the subject can be accomplished in a number of ways. Referring to the particular implementation of FIGS. 4 and 8A-8B, the alignment guide/splay shield 108 is equipped with a force contact pickup 128. The alignment guide/splay shield 108 can be mechanically biased in a distal direction (towards the subject) using one or more force contact springs 126, of which four are shown in FIG. 4. The force contact pickup 128 changes its position by virtue of the force applied to the alignment guide/splay shield 108. In so doing, it also changes the state of an electrical circuit formed by the force contact pickup 128, a set of first pads 162, a set of second pads 164, and a flexible circuit 160. In particular, by testing for continuity between one or more pads 162 and one or more respective pads 164, it can be determined how far backward or proximal the alignment guide/splay shield 108 has been moved by applied force, and thus if sufficient force exists for proper delivery. The state of the circuit is read by the applicator 400 using sensor contacts 434 (see FIG. 16). If sufficient force is indicated, the force contact interlock is deactivated, allowing the user to operate the device.

In one implementation, at the first contact point, the system may not register that any particular force has been applied. At the second contact point, the system may register that it is at partial (but not sufficient) pressure. At the third contact point, the system may register that the prescribed level of pressure required to proceed with procedure administration has been achieved, and the interlock may deactivate. Preferably, the status of the force contact circuit is provided to the user via the applicator display 404.

Variations are to be understood by a skilled person in the art. For example, the force contact interlock may form an electrical lock that is deactivated either within the controller 700 or within the applicator 400 itself. In another variation the force contact circuit may be configured to provide information regarding the status of the device throughout the procedure administration. In particular, the system may include a feedback loop between the force contact circuit and the controller 700 wherein a reduction in the force applied by the user precipitates the generation of a visual, haptic, or auditory signal by the controller 700 and/or applicator 400 so that a state of reduced force can be corrected. In a certain embodiment, a feedback loop exists between the force contact circuit and the controller 700 such that the detection of a change in the applied force prompts the system to initiate a check as to whether the electrodes remain properly deployed into the tissue of the subject, e.g., via an impedance or resistance check between the electrodes. If the check is passed, then the procedure proceeds normally. In the event that the position of the electrodes is no longer acceptable then the procedure may be aborted and the user notified of the state of the device through the generation of a visual, haptic, or auditory signal by the controller 700 and/or applicator 400. This feedback loop is of particular significance during the injection of the medicament. By monitoring the position of the device and the state of the electrodes, the feedback loop between the force contact circuit and electrode resistance/impedance monitor, the system may detect if the electrodes (and therefore the injection needle) are no longer in the subject, allowing the system to halt operation of the injection drive mechanism 456 to cease depressing the reservoir plunger 484 and terminating the injection of the medicament. While this embodiment is most readily implemented with a motor driven injection drive 456, other variations can be implemented in the case of manually operated or spring drive mechanisms wherein the activation of mechanical interlocks may be used to halt actuation of the reservoir plunger following detection of a fault condition. This feature may be particularly useful in stopping the therapeutic agent from inadvertently spraying out into the environment for instance, where the applicator 400 is removed from the tissue of the subject prior to completion of a medicament delivery. For medicaments or therapeutic agents that are potentially hazardous for exposure to users or the environment, such a design may avoid inadvertent discharges/exposures.

Since the quantity of the dose delivered to the subject in a partial dose situation may be critical to inform the decision making of the clinician regarding further treatment, it is preferable that the injection drive mechanism 456 include appropriate sensor and control features to determine the position of the injection drive plunger 484 at the time the injection stroke was halted due to the detection of a fault condition or other circumstance in which halting the injection stroke is necessary. Preferably this is achieved through monitoring of the revolution count of the motor used to drive the injection drive plunger 484, but other methods for monitoring the position of the injection drive plunger 484 including optical or electrical sensors may be employed. Based on the known dimensions of the injection drive plunger 484, the depth of insertion, and the reservoir 101, the use of appropriate logic and control circuits can translate the position of the injection drive plunger into an estimate of the volume of medicament remaining in the syringe at the point at which the injection stroke was terminated. Such information can be conveyed to the user via the display 712.

In addition to providing a termination feature to terminate the injection stroke in the event that a fault condition is detected, the use of a motor injection drive 456 can also provide a supplementary detector for detection of a fault condition or other operational issue. Specifically, the incorporation of appropriate measurement and logic circuits to monitor the circuit drawn by the motor during the injection stroke can be used to confirm that the injection has been administered within defined specifications. Expected ranges for the current drawn by the motor can be established for the various stages of the injection stroke including the initial run up of the injection drive plunger 484 before it contacts the plunger stopper 159, the initial interface between the injection drive plunger 484 and the plunger stopper 159, actuation of plunger stopper 159 forward in the barrel of the reservoir 101, and conclusion of the injection stroke as the plunger stopper 159 contacts the end of the barrel of reservoir 101. By correlating the position of the injection drive plunger 484 with the measured current drawn by the motor to the expected values during each phase of the injection of the agent, the system is capable of identifying potential fault conditions and conveying them to the user. For example, if the user inadvertently inserted a reservoir 101 in which the plunger stopper 159 had been partially actuated (and therefore did not contain the full intended dose of medicament) into cartridge 100, the system could detect that the expected increase in current drawn by the motor injection drive 456 did not occur when the injection drive plunger 484 reached the outer tolerance for plunger positioning. Under this circumstance the system could terminate the administration procedure and notify the user of the detected fault. Additional fault conditions including (but not limited to) faulty components in the applicator 400, breakage of the reservoir 101, and/or a defective cartridge 100 would be potentially detectable via this method.

Figure 9A:
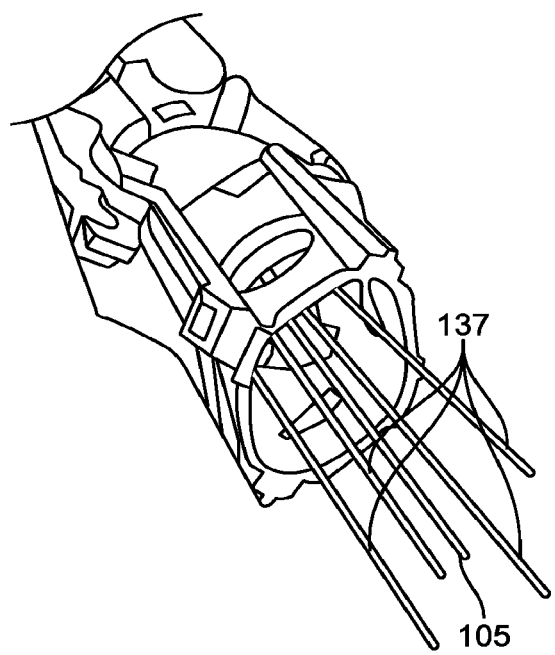
FIGS. 9A-9D show views of aspects of a device described herein.
Figure 9B:
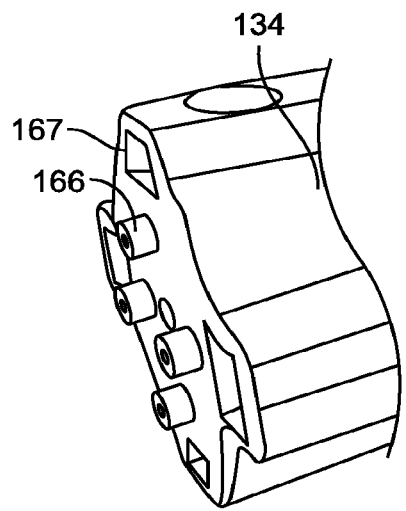
Figure 9C:
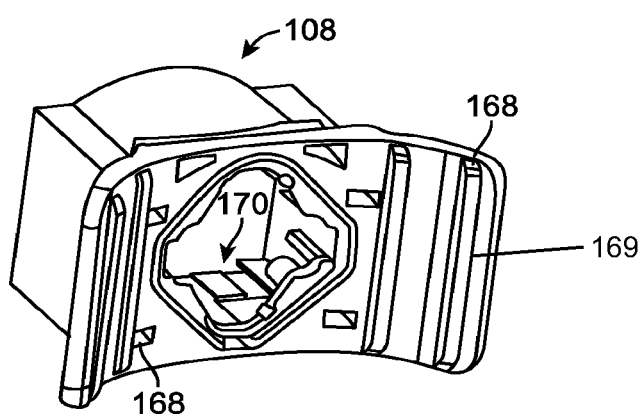

Another 'interlock' to facilitate proper execution of the administration procedure is provided by the alignment guide/splay shield 108, which is illustrated in FIG. 9C. In this figure, the alignment guide/splay shield 108 is shown with splay features 168 and a hole 170 defined therein for slidable movement of a stick shield 134. The stick shield 134 is illustrated in FIG. 9B, and electrode holes 167 are also illustrated. For transcutaneous insertion of electrodes and, where relevant, injection needles, having a consistent skin interface facilitates deployment of electrodes into the target tissue while maintaining the desired spatial relationship between the members of the plurality. In particular, proper deployment is most consistently achieved when the skin is positioned perpendicularly to the direction of deployment. In addition, misalignment of the electrodes and injection needle are reduced when the skin is placed into tension in the orientation perpendicular to the direction of deployment. As can be seen, the splay shield 108 includes mechanical features including ribs 168 and edges 169 to engage with the skin and place it into tension perpendicular to the direction of deployment. Combined with the force contact circuit pick up system described above which ensures a consistent force applied to the skin, the alignment guide/splay shield 108 ensures that the skin is oriented and placed under tension in the direction perpendicular to the direction of electrode deployment. While this embodiment utilizes mechanical rib features to engage the skin at the device interface, numerous other designs and features could be utilized for engagement including the use of alternative materials with a high coefficient of friction when placed in contact with skin (e.g., rubber insets, adhesive patches, and the like) or alternative mechanical features including molded textures, cut outs, and sawtooth features capable of placing the skin into tension.

As can be seen, the alignment guide/splay shield 108 has a preferential direction defined. As described above, spatial and temporal co-localization of the medicament distribution and electric field application are desirable. Notably, the inherent structural properties of skeletal muscle lead to a characteristic ellipsoid distribution pattern of intramuscular injections where the major axis of the ellipsoid aligns with the striations of the muscle fibers. For applications involving intramuscular injections, it is therefore favorable to arrange the electrodes to generate an ellipsoid electric field profile. In order to ensure that the electrode array and resultant electric field profile are properly oriented relative to the striations of the target skeletal muscle, the use of an alignment guiding feature is of particular utility for intramuscular administration. The objective of the alignment guiding feature is to facilitate placement of the device such that the orientation of the electrode array is most favorable relative to the muscle striations and the resulting medicament distribution following injection. For an arm injection, the alignment guide/splay shield 108 would desirably wrap around the arm horizontally like an arm band. A similar orientation would be desired for the leg with the splay shield wrapping around the leg horizontally. It has been found that having the alignment guide/splay shield 108 configured in this manner results in >98% accurate medicament deliveries by users even in the absence of verbal instructions. The preferred direction shown and resulting skin placement is particularly useful for intramuscular injections, because the diamond shaped array of electrodes (see the array of distal ends of electrodes 137 in FIG. 9A, which roughly matches the shape of the stick shield 134 and its associated holes 167) is then oriented properly to deliver a medicament and to cause electroporation of the medicament along the preferred muscular striation direction. A primary feature is that, when aligned properly, the skin should be flush with the skin interface where the orifice is located, e.g., where the needle emerges. In this way, a consistent interface to the skin is obtained.

Where the alignment relative to the target muscle is improper, the arc generally causes a visually evident gap, e.g., 2-5 mm, to occur between the alignment guide/splay shield 108 and the skin. The visually evident gap may be employed as a reminder to the user to reorient the applicator 400. In addition, the applicator 400 can be less stable against the skin of the subject when it is improperly aligned. Alignment guide features wherein the distance between edges of the "wings" of the feature are at least 1.3 times the vertical height of the feature are preferable for facilitating proper placement. In addition, in some cases the design of the feature is such that the tissue interface can be placed flush against the skin in the desired orientation while exhibiting at least a 2 mm air gap when placed at a 90 degree angle relative to the desired orientation.

Variations on the design of the alignment guide are to be understood by a skilled person in the art. For example, instead of an arc shaped alignment guide/splay shield 108, a "V" shaped one may be used. Other variations are also to be understood with the key characteristic being that the device can be placed directly against the skin in the desired orientation whereas a visually apparent gap between the tissue interface and the skin of the recipient of 2 mm or greater is present when the device is misaligned relative to the striations of the target muscle.

As noted above, the orientation of the alignment guide/splay shield 108 is related in some implementations to the shape of the electrode array, because the diamond symmetry of the electrode array has a certain distribution associated with it, and this distribution should bear a certain predetermined relationship to the shape of the alignment guide/splay shield 108. Referring to FIGS. 9A-9B, the electrodes, and more particularly the distal portions 137, are shown, which are four in number. The electrodes are positioned in a diamond shaped array, which means they have second order symmetry, i.e., are twofold symmetric, in that they may be rotated and at two different positions appear the same. The electrodes extend in this array from holes 167 defined in the stick shield 134. The use of a diamond shaped array is particularly useful because it is generally desired for intramuscular injections as discussed above. To reiterate, the second order symmetric array leads to a second order symmetric applied electric field. This type of applied electric field can have a preferred direction along the striations of the muscles if the alignment guide/splay shield 108 is oriented properly. Thus the alignment guide/splay shield 108 and the second order electric field orientation work together in a synergistic fashion to accomplish medicament propagation along the direction of muscle striation.

Broadly speaking, in a diamond shape, or other second-order symmetric shape, there is generally a major (long) axis and a minor (short) axis. The axes may bear a predetermined relationship with a preferred axis of the alignment guide/splay shield 108. For example, if the alignment guide/splay shield 108 is thought of as having wings, with the arcuate shape of the wings encircling the arm, then a line segment connecting the center of the wings may be perpendicular to the major axis of the diamond shaped array.

Variations are to be understood by a skilled person in the art. For example, while a diamond is one possible shape for an electrode array, another exemplary shape is a rectangle, which is also second-order symmetric. The electrodes may be placed into the appropriate positions but may be moved to within a predetermined or desired tolerance, e.g., within 5%, 10%, and so on. Electrodes may be in various other shapes so long as they create a second order rotationally symmetrical electric field.

In another variation, for non-intramuscular injections, other order symmetries may be used. For example, for skin, there is generally no preferred direction of medicament propagation and so even a circular array of electrodes may be employed for intradermal injections.

Other considerations of electrode arrays are as follows. The simplest array configuration comprises two electrodes connected to the opposite poles of the electrical energy source. As disclosed in U.S. Pat. Nos. 5,873,549 and 6,041,252 (incorporated herein by reference in their entirety), utilization of three or more simultaneously active electrodes arranged in a multi-element array can be used to increase target volumes of tissue and improve the uniformity in electrical field propagation within the target tissue. A wide range of geometrical electrode arrangements and activation patterns have been developed for electric field application in tissue. These include electrodes arranged in linear, rectangular, circular, or triangular configurations capable of propagating electrical fields in a volume of tissue of roughly ellipsoid, cuboid, cylindroid, or spheroid shape. Most commonly, the electrodes are arranged parallel to one another and configured for transcutaneous insertion in an orientation substantially perpendicular to the skin surface. In order to ensure that the target volume and shape of tissue is affected by the application of electrical field, it is desirable that the intended spatial relationship between each of the electrodes within the array is achieved following transcutaneous insertion. Specifically, unintended changes in the inter-electrode spacing should be avoided as they can cause changes in the magnitude of the electrical fields propagated within the target tissue, potentially leading to negative consequences for the safety and/or efficacy of the procedure.

Another interlock involves use of an exterior cartridge cap 110. In particular, the alignment guide/splay shield 108 is covered while stored with an exterior cartridge cap 110. The exterior cartridge cap 110 is configured to not just generally protect the distal end of the device until use but also to serve an interlock feature itself. While protection of the distal end of the cartridge assembly 100 serves the purpose of protecting the needle and electrodes from the environment, a commonly-encountered problem is that users often forget to remove such caps. One solution is to make the cap a bright color that is different from the color(s) of the other components in cartridge 100, so as to notify the user of its presence and thus remind the user to remove it. Another part of this solution is to include an extension or reminder tab 190, as shown by the arcuate section adjacent a rectangular section, the arcuate section visible even when the cartridge assembly 100 is placed up against a subject. As this reminder tab 190 is visible, it can serve as a reminder to remove the exterior cartridge cap 110 even when the remainder of the exterior cartridge cap 110 is not visible.

Figure 10C:
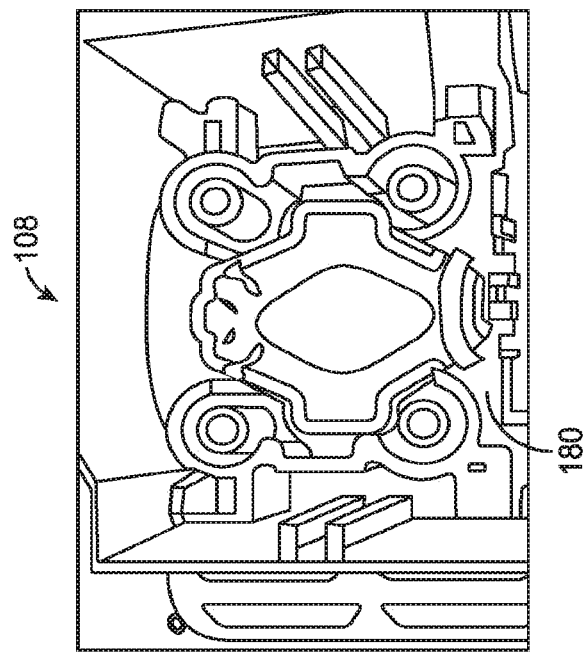
FIGS. 10A-10D show views of aspects of exterior cartridge cap in a device described herein.
Figure 10B:
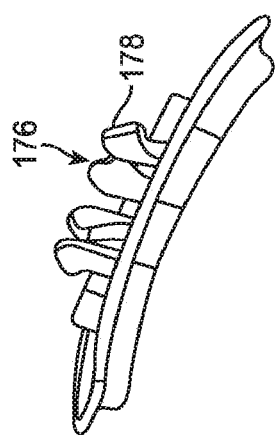
Figure 10A:
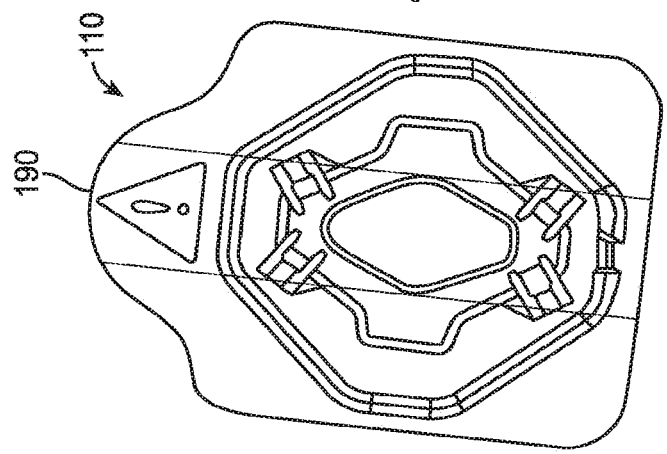
Figure 10D:
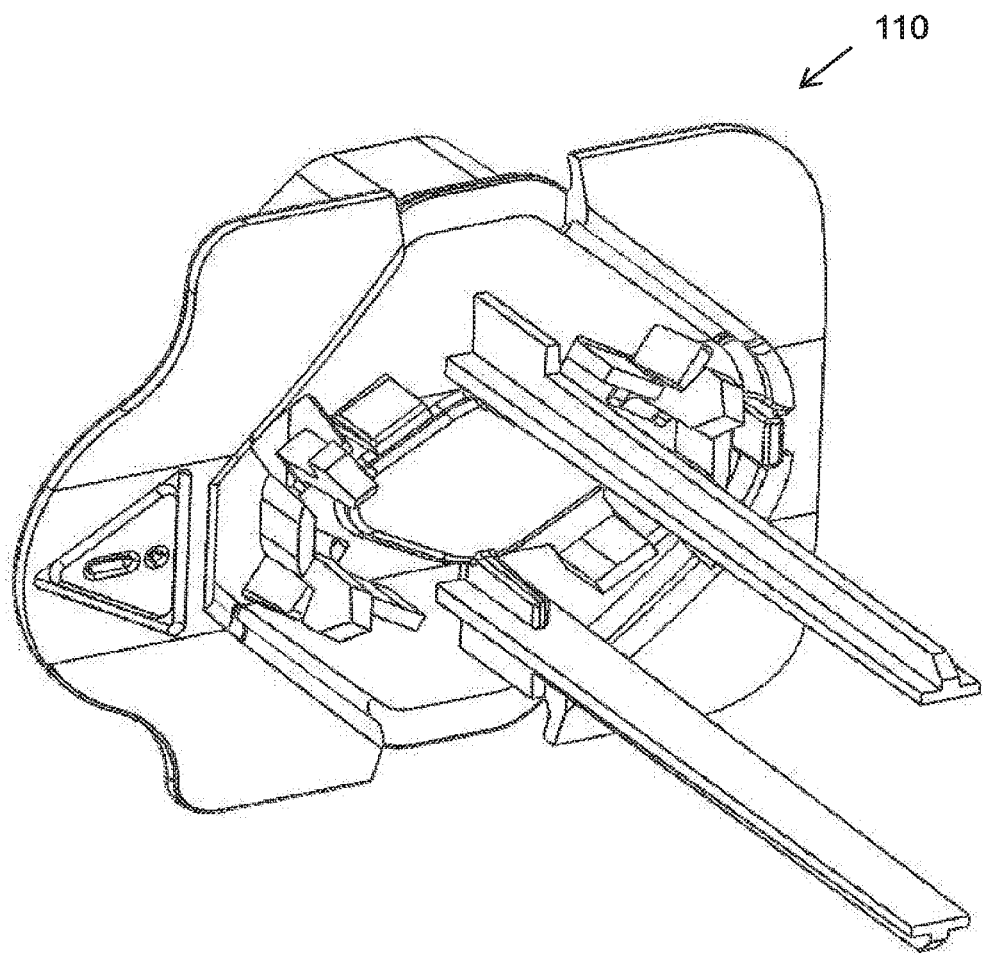

Referring in more detail to FIGS. 10A-10B, the exterior cartridge cap 110 includes an outer surface facing distally, towards the subject, and an inner surface facing the alignment guide/splay shield 108. On the inner surface are provided a number of hooks 176 which engage a corresponding wall 180 defined on the alignment guide/splay shield 108. The hooks hold the exterior cartridge cap 110 in place.

However, if the exterior cartridge cap 110 were inadvertently left in place, and the applicator 400 pressed up against an insertion site with force, the force of the alignment guide/splay shield 108 against the exterior cartridge cap 110 may tend to cause the exterior cartridge cap 110 to "pop off" by being pushed away from its hooked position by the alignment guide/splay shield 108. However, chamfered surfaces 178 are provided on the hooks 176 which tend to act against the stick shield 134 when pressure is applied, causing the hooks 176 to splay outward, increasing their retaining force against the alignment guide/splay shield 108, and preventing the exterior cartridge cap 110 from popping off. In addition, the chamfered surface acts further against the stick shield, preventing the alignment guide/splay shield 108 from moving relative to the stick shield 134. If the alignment guide/splay shield 108 cannot move relative to the stick shield 134, the force detection interlock cannot be deactivated, as the force contact pickup 128 cannot move to the third force contact point discussed above, where full pressure is detected (or for that matter even to the second force contact point). The controller can provide a report when this happens to the controller. For example, a user interface indication such as "You need to remove outer cartridge cap." may be displayed, the same caused by detection of a trigger pull performed in the absence of adequate force.

While certain interlocks have been described above, more or less interlocks may be provided in any given implementation. For example, other ways may be employed for force detection and use as triggering signals for interlocks. Other types of interlocks may also be employed, including trigger locks, safety switches, and the like. Yet other types are to be understood by one of ordinary skill in the art, given this teaching.

Once a depth of insertion is affirmatively selected by the user, and the exterior cartridge cap 110 is removed, and the proper force is detected by the force interlock, activation of the trigger causes clockwise or counterclockwise rotation of the cartridge lock ring 114, with the direction of rotation dependent on the depth of insertion selected by the user. The rotation causes the retaining posts 488 to move into the channels of selected depth, which in turn causes the needle and electrodes to deploy. In particular, the inner cartridge 103, cartridge breech 112, reservoir 101, inner cartridge cap 104, needle hub 152, needle 105, electrodes 122, and associated elements to move forward under the influence of the electrode/needle insertion spring 472. In the present embodiment, these elements are rigidly connected to each other and thus move forward as a unit.

To further minimize the risk of sharps injuries to the user, it is preferable that the cartridge assembly also incorporates a mechanism for sheathing the electrodes and any injection needles following their removal from the recipients' tissue. This can be accomplished through the incorporation of a stick shield feature that houses the electrodes and injection needle (if present) prior to their use and then extends over the electrodes and injection needle (if present) following their deployment and removal from the tissue of the subject. Commonly, the tissue contact interface comprises the distal surface of the shield feature. Although the use of manually operated shield features may be considered, preferably, the device incorporates a mechanism to automatically extend the shield feature over the electrodes and further to engage a locking feature to maintain the shield feature in the extended state once it has been removed from the tissue of the recipient. Examples include a shield feature slidably engaged with the cartridge outer housing and operatively connected to a source of stored energy, such as a spring, which slides the shield forward upon withdrawal of the electrodes from the recipients' tissue. Alternatively, the mechanism can be contained within the applicator and configured to reverse the electrode deployment step, thereby retracting the electrodes and any associated injection needles behind the tissue contact interface. This can be accomplished using simple electromechanical mechanisms for linear motion such as motors or solenoids.

Figure 11A:
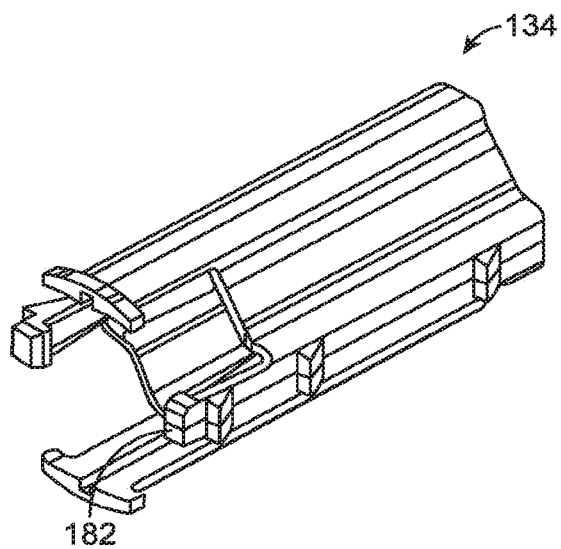
FIGS. 11A-11C show details of stick shields in aspects of a device described herein.
Figure 11B:
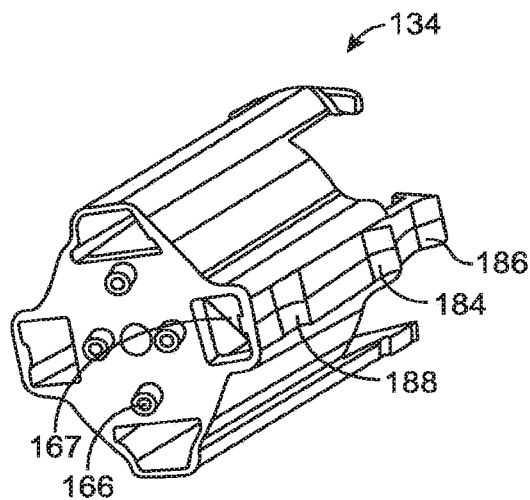
Figure 11C:
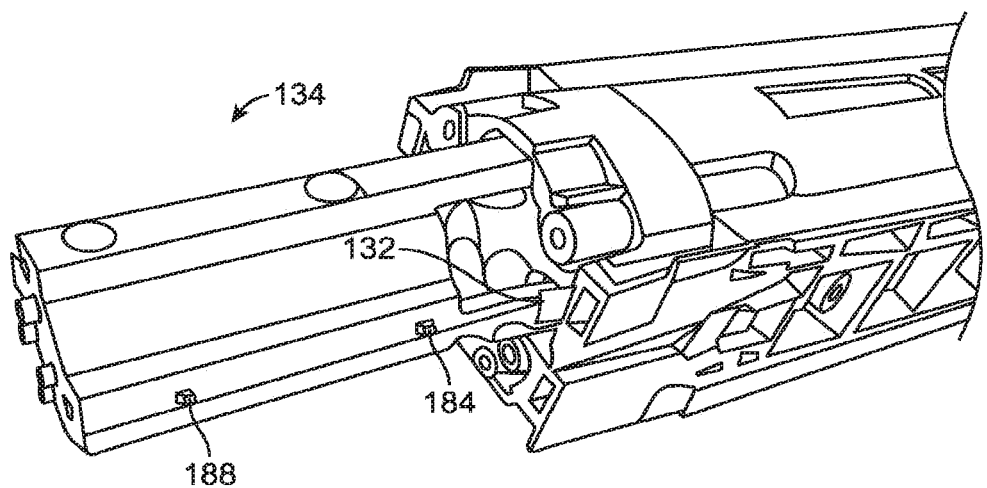
Figure 12:
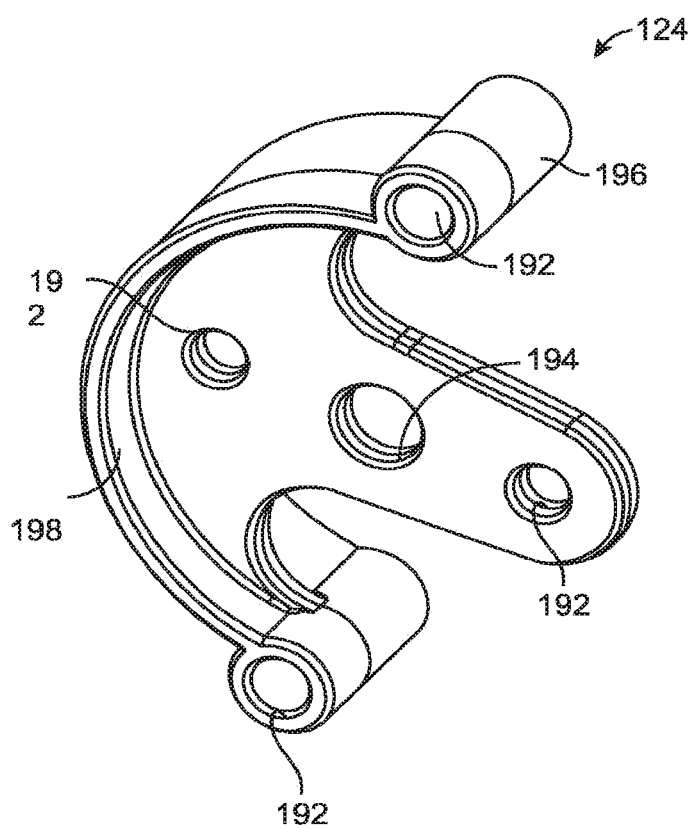
FIG. 12 shows details of an electrode support 124 according to present principles.
Figure 13:
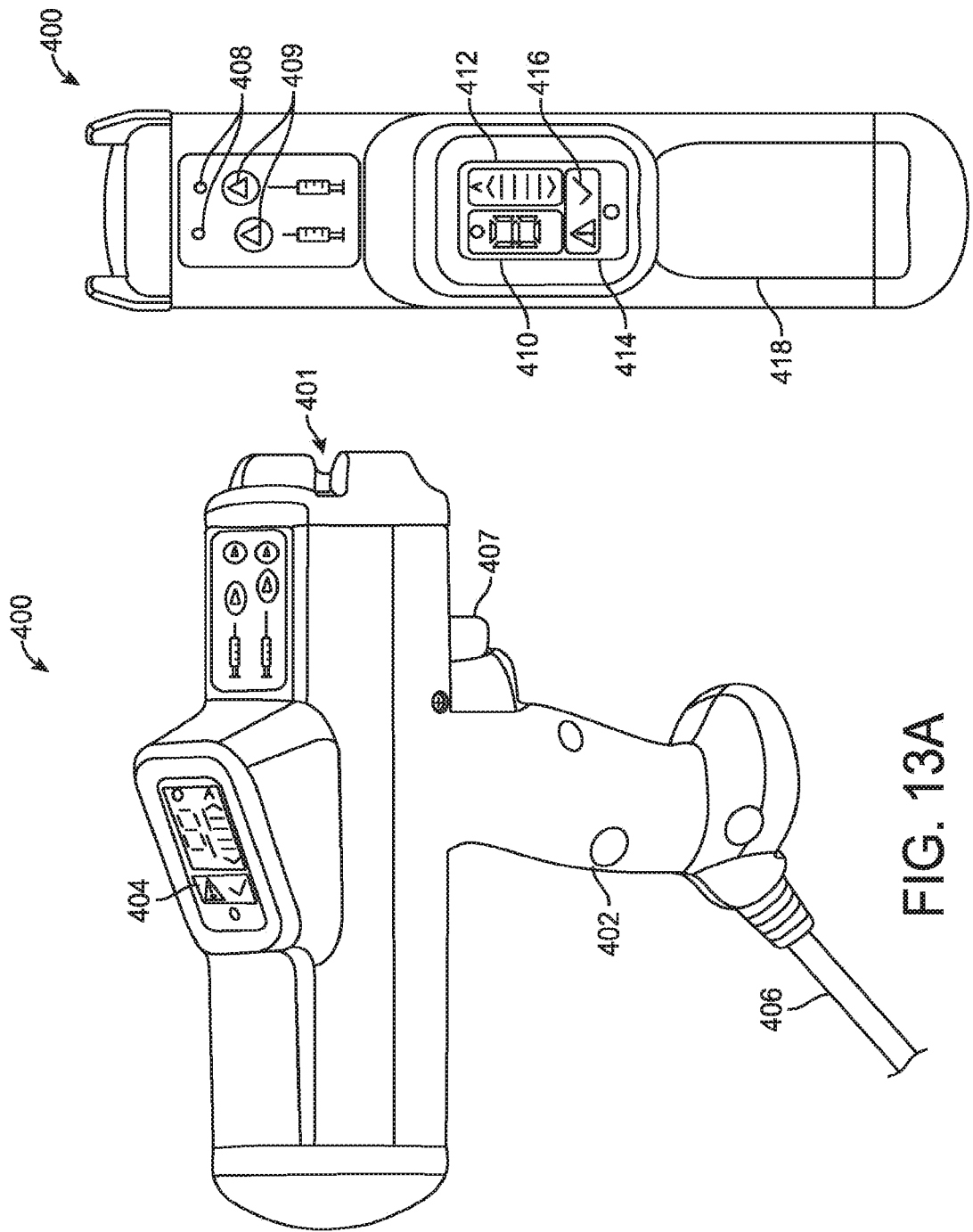
FIGS. 13A-13B show views of an applicator in a device described herein.

In a particular implementation, and referring back to FIG. 4 as well as to FIGS. 11A and 11C, the stick shield 134 is configured to stay in position while the medicament delivery happens, but the movement forward of the inner cartridge 103 and other associated components during medicament delivery causes compression of a stick shield spring 138. This compressed stick shield spring 138 then relaxes as the applicator is removed from the subject, as the stick shield 134 is caused to move forward when the applicator 400 is removed from the subject, covering the needle and electrodes, and protecting the subject and others against the uncovered sharps. Notably, this feature also prevents the visualization of the sharps features during withdrawal, which can facilitate acceptance from subjects experiencing anxiety related to needles.

While the relaxed spring would otherwise be capable of recompressing, and in particular if the user moved the stick shield 134 proximally, it is prevented from doing so by the action of stick shield support arm 132, which are mounted to the interior of the outer cartridge 102 and which serve a ratcheting function as the stick shield 134 moves forward. In particular, and referring to FIGS. 11A and 11C, stick shield support arms 132 move over various sequential retaining walls, and can do so easily when the stick shield 134 is moving distally. However, in the proximal direction, the stick shield 134 is prevented from moving because the stick shield support arms 132 abut the retaining walls in this direction, in a ratcheting fashion, and do not allow passage.

An initial set of retaining walls 188 prevent proximal movement of the stick shield 134 prior to use of the cartridge assembly 100. A set of first depth retaining walls 184 prevent proximal movement of the stick shield 134 after discharge at a first selected depth. A set of second depth retaining walls 186 prevent proximal movement of the stick shield 134 after discharge at a second selected depth. The stick shield 134 is prevented from complete removal from the cartridge assembly 100 by the action of the stick shield retaining hooks 182 acting against the inner cartridge 103. In some embodiments, final lock out at final end of the stick shield.

Figure 9D:
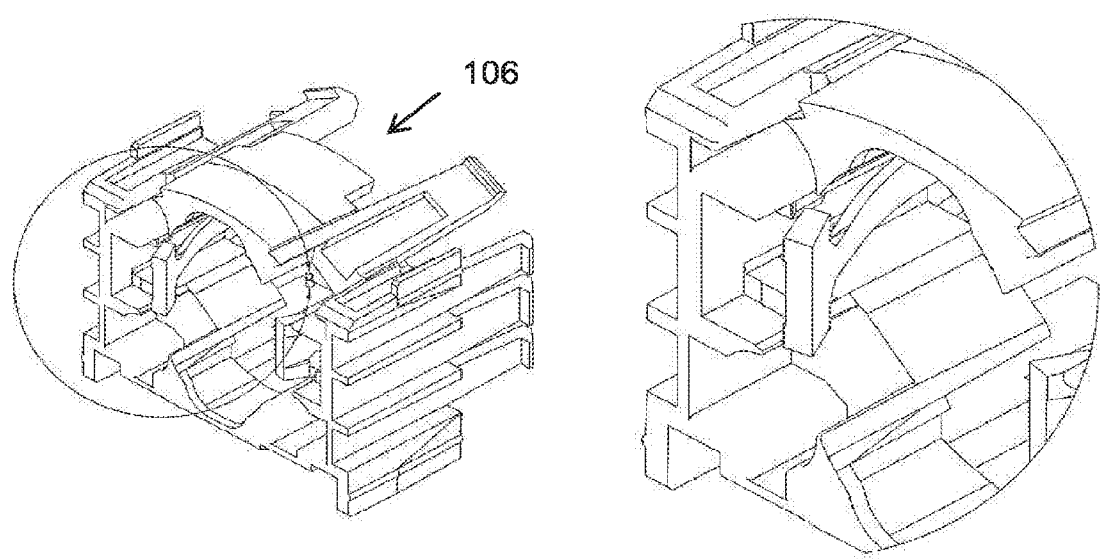

Variations is to be understood by a skilled person in the art. For example, in one implementation the stick shield support arms 132 may be provided by stamped metal support arms that interface with the outer cartridge 102. In some embodiments, for instance, as shown in FIG. 9D, the support arm features are directly integrated as stick shield retention features, for instance injection molded plastic features in the outer cartridge cap 106 and/or alignment guide/splay shield 108. The specific material can be selected to achieve sufficient rigidity to provide support to the elongate electrodes while retaining sufficient elasticity to prevent fracture of the component under load. Material selection should also consider the intended method of sterilization for the electrode array (e.g., gamma radiation, steam sterilization, ethylene oxide, or e-beam) to ensure that the features retain adequate material properties following sterilization. In an exemplary embodiment, the features, as implemented, should be capable of holding the stick shield 134 against proximal movement when at least 5 N, but more preferably at least 15 N of force applied. Other ways of providing a ratcheted function to prevent proximal movement of the stick shield may also be employed including a gear rack implemented on stick shield 134 and a corresponding ratchet feature implemented in outer cartridge cap 106.

Referring to FIG. 4, each elongate electrode 122 within the array comprises a distal portion 137 and a proximal portion 135 that are in conductive communication. The distal portion is configured for tissue penetration and electric field propagation in tissue and the proximal portion is configured with a conductive contact region capable of reliably achieving conductive communication with the electrical connections contained within the applicator with a suitable source of electrical energy. The source of electrical energy can, by temporal variation in the power applied to individual electrodes, cause a spatially and temporally varying electric field within the body of the subject, generally confined to a volume around the region of medicament distribution, and the same can be used to advantage in electroporation therapy.

The relevant characteristics of the electrodes include shape, diameter, tip profile, length, material composition, and conductivity, the specifics of which are selected based on the intended application. Most commonly, the electrodes comprise electrically conductive elongate rods with a curvilinear cross section with diameter 0.1-1.5 mm. The electrodes may be solid core or hollow. Most commonly hollow electrodes incorporate one or more orifices and an operative connection to a fluid reservoir, thereby allowing for the administration of the agent of interest or other associated medicaments including anesthetics, surfactants, proteins, adjuvants, or enhancers from the electrode itself. Depending on the application, appropriate metallic electrode materials include, but are not limited to titanium, gold, silver, aluminum, copper, tantalum, tungsten, molybdenum, tungsten, stainless steel, MP35N and alloys thereof. Electrodes may also be comprised of electrically conductive ceramics or plastics. To minimize unwanted electrochemical reactions at the tissue electrode interface, it is often desirable that one or more of the electrodes are coated in a conductive material providing improved electrochemical stability compared to the electrode material itself. Such coating materials include, but are not limited to, platinum, platinum, iridium, palladium, osmium, gold, silver, titanium, and alloys thereof.

As described above, the tip of the distal portion is configured for tissue penetration. Common tip profiles include, but are not limited to, trocar, bevel, cone, blade, lance, and taper. For transcutaneous electrode deployment, tip profiles with one or more cutting edges are preferred. For certain applications where the penetrating tip profile may be undesirable for generating the required electrical fields, the tip may be comprised of a non-conductive material fixed to the distal tip of the electrode or the penetrating tip may be covered in an adherent coating or tubing comprised of an biocompatible electrically insulating material such aspoly (p-xylylene) polymer, polyolefin, polyvinyl chloride, polyurethane, polyester, polyimide, silicone rubber, thermoplastic elastomer/rubber, ethylene tetrafluoroethylene, fluorinated ethylene propylene, and/or perfluoroalkoxy plastic.

Proximal to the penetrating tip are one or more conductive regions configured for the propagation of electrical fields in tissue. In order to confine the propagation of electrical fields to the target region of tissue, commonly, especially for subcutaneous and intramuscular administration, at least a portion of the electrode length configured for penetration in the tissue is covered in an adherent coating or tubing comprised of an biocompatible electrically insulating material such aspoly(p-xylylene) polymer, polyolefin, polyvinyl chloride, polyurethane, polyester, polyimide, silicone rubber, thermoplastic elastomer/rubber, ethylene tetrafluoroethylene, fluorinated ethylene propylene, and/or perfluoroalkoxy plastic. In this way, electrodes may be configured to only activate at a particular depth within the tissue.

Collectively, the number of electrodes and their inter-electrode distance as well as the penetration depth of the electrodes and the length of their conductive region define the volume of tissue in which the electric fields is applied. These parameters are selected based on the specific objectives for the administration procedure, including target tissue site as well as the volume, dose, and viscosity of the agent to be delivered as well as the variation in skin and subcutaneous tissue thickness in the intended recipient population. Generally, for intradermal administration in human recipients, arrays comprise 2-16 electrodes of diameter 0.2-0.7 mm, an inter-electrode distance of 2-8 mm, a depth of electrode penetration of 0.5-4 mm, and a conductive length of 0.5-4 mm. Generally, for subcutaneous administration in human recipients, arrays comprise 2-8 electrodes of diameter 0.3-0.8 mm, an inter-electrode distance of 4-10 mm, a depth of electrode penetration of 5-15 mm, and a conductive length of 2-8 mm. Generally for intramuscular administration in human recipients, arrays comprise 2-8 electrodes of diameter 0.3-1.2 mm, with an inter-electrode distance of 4-12 mm, a depth of electrode penetration of 10-60 mm, and a conductive length of 2-20 mm.

In order to avoid undesirable visualization and exposure to the electrodes during the usage of the device, the cartridge assembly 100 is preferably configured such that the electrodes 122 are recessed within the device prior to their insertion into the tissue of the recipient. Most commonly, this is accomplished by providing the outer housing structure 102 slidably engaged with the electrode mount support, which in one implementation comprises an inner cartridge 103 having seems formed therein in which the electrodes are disposed. Prior to use, the electrodes are recessed within the outer housing 102. During use, the sliding engagement of the electrode mount structure, e.g., the inner cartridge 103, with the outer housing allows the electrodes 122 to slide forward relative to the distal tip of the outer housing 102, thereby deploying the electrodes 122 from the outer housing 102. The length of the sliding engagement between the electrode mount structure and the outer housing corresponds to the maximum desired depth of electrode penetration for the given application.

As may be seen in FIG. 4, and the electrodes 122 have a proximal portion 135 and a distal portion 137. The proximal portion is separated from the distal portion by a shoulder or bend 139. The shoulder or bend 139 is secured by and between the inner cartridge cap 104 and the inner cartridge 103. The shoulder or bend 139 provides a number of functions. First, while the electrodes at the distal end of the cartridge assembly 100 are required to form an array of a certain size and shape as described above, putting the electrodes 122 in the desired array size and shape at the proximal end of the cartridge assembly 100 is impractical due to the presence of the reservoir 101. In other words, the electrodes 122 have to bend "out-of-the-way" to make room for the reservoir 101. In addition, having the bend, particularly when the bend is locked in place frictionally between the inner cartridge 103 and the inner cartridge cap 104, provides a surface for the electrodes 122 to abut against when the force of the needle and electrodes insertion recoils in the distal direction as the electrodes 122 interact with the tissue during their deployment. The bend, can resistant to axial rotations, which is beneficial so that the electrodes do not exhibit significant torsional movement and rotate away from their electrical contact pads 130 (described below). In addition, in contrast to prior art techniques in which multiple electrodes interfaced with axially separated coaxial rings, requiring a different configuration for each electrode, the present system allows a common electrode type to be used for all four electrodes.

Systems and methods according to present principles provide for the propagation of an electrical field in the skin, subcutaneous tissue, and/or skeletal muscle of a recipient which facilitates the intracellular delivery of a therapeutic agent within said recipient's tissue. In this aspect, the apparatus includes two or more elongate electrodes 122 arranged in a predetermined spatial relationship and configured for deployment into the target tissue in which the agent of interest has been or is to be distributed. The desired enhancement in agent activity is contingent on achieving co-localization of the site of agent distribution with the propagation of electrical fields of sufficient magnitude to induce the desired physiological effects. Therefore it is desirable that the apparatus consistently achieve electrode deployment to the target depth and with specified intraelectrode spacing. Specifically, this ensures that the electrical fields are propagated at the proper tissue site, and, since the magnitude of the electrical fields propagated within the tissue is a function of the intraelectrode spacing, a safe and effective electric field intensity. However, the variation in the thickness, density, and composition of skin and subcutaneous tissue between sites in a given recipient and across recipient populations can lead to significant variation in electrode deployment characteristics. For example, recipients with increased thickness of skin are at increased susceptibility for electrode distortion and/or insufficient depth of penetration which can affect co-localization with the site of agent distribution.

Systems and methods according to present principles further facilitate consistent transcutaneous insertion of electrode arrays comprising 2-16 electrodes of diameter 0.2-1.3 mm with an inter-electrode distance of 2-12 mm, and a depth of electrode penetration of 0.5-60 mm in recipients with skin of heterogeneous thickness, composition, and condition. In order to permit transcutaneous insertion, tissue penetrating electrodes are most commonly elongate and configured with a tissue penetrating tip and a tissue contact region in the distal portion and an electrical contact region in the proximal portion. Given their elongate configuration, they are susceptible to bowing, bending, and/or buckling (collectively termed distortion) when subjected to the compression forces generated during transcutaneous insertion into the recipient. Such distortions during electrode insertion are undesirable as they can lead to improper electrode insertion characterized by insufficient depth of penetration and/or excessive changes in intraelectrode spacing. Of note, humans and animals exhibit significant intra- and inter-species differences in the thickness, composition, and condition of skin, any of which can have significant impact on the forces which the electrodes are subjected to during transcutaneous insertion. In some embodiments, devices for transcutaneous insertion of elongate electrodes are designed to withstand the forces present under the most stringent conditions of electrode insertion that is to be encountered in the target population of recipients. The occurrence of electrode distortion can be partially mitigated by electrode material selection as well as reducing the length and increasing the diameter of the electrodes within the array. However, material selection may be constrained by issues of performance, cost, manufacturability, and biocompatibility. In addition, electrodes of reduced length may preclude adequate coverage of a target population with heterogeneous tissue thickness while larger diameter electrodes are associated with increased discomfort and tissue trauma. Thus, the present disclosure is designed to provide methods and apparatus to facilitate the transcutaneous insertion of electrodes independent of these variables.

A first embodiment of the disclosure the subassembly cartridge housing the electrode array incorporates one or more support dynamic support members in physical contact with one or of the electrodes during tissue insertion and configured to constrain movement of the electrodes perpendicular to the direction of insertion and maintain the desired spatial relationship between the electrodes. For example, and referring to FIG. 12, an electrode support 124 is illustrated in which electrode holes 192 are provided for electrodes and a needle hole 194 is provided for passage of the needle. The tendency of the elongate electrodes to distort or buckle under load is exacerbated by any bending, eccentricity, or bowing of the electrode that may have been introduced during manufacture or assembly. Thus, it is advantageous to employ a device such as the electrode support 124 to constrain the electrodes to prevent, or correct, any bending, eccentricity, or bowing they might exhibit at rest, and to prevent unwanted perpendicular motion of the electrode as a result of the loading that occurs during deployment into tissue.

In the context of the present disclosure, a dynamic support member is defined as a structural element which provides sliding engagement with the elongate electrodes during insertion into the tissue of the recipient and which is configured to undergo a change in position, size, and/or conformation during electrode insertion in order to maintain the desired spatial relationship of the electrodes as they are deployed to the target tissue depth. Since the electrodes are subjected to the largest loading forces at the initial contact with the skin, the engagement of the dynamic support member with the electrodes comprising the array is preferably affected prior to initial contact with the tissue of the recipient and to continue to provide support as the electrodes deploy to the full depth of penetration. It is also favorable that the dynamic support member be designed to provide support to the electrodes and injection needle while minimizing losses in electrode penetration force due to friction.

While the primary function of the dynamic support member is to maintain the desired spatial relationship of the plurality of the electrodes within the array relative to one another and to the injection needle, it is also desirable for the design of the dynamic support member to include features capable of stabilizing the array as a whole. This is preferably accomplished by providing additional structural support features which constrain lateral movement of the support member. In a certain embodiment, these support features are integrated into a sharps protection shield, which also serves to protect the user against accidental exposure to the electrodes and/or injection needle. Disclosed below are various embodiments of dynamic support members consistent with the present disclosure.

One embodiment of the present disclosure, described above as electrode support 124, involves the use of a planar structure positioned perpendicularly relative to the elongate orientation of the electrodes. The planar structure is configured with one or more apertures 192 which correspond to the positions of said electrodes in their specified spatial relationship. The size, shape, and position of the apertures are configured to allow the support structure to slide smoothly along the elongate length of the electrodes within the array while constraining unwanted motion perpendicular to the direction of electrode deployment. Commonly, the apertures may be configured as holes or slots 192 in the planar structure with adequate clearance for the electrode (at least 10% larger than the largest cross section of the electrode, including any coatings or other adherent materials). However, if more substantial support is required for specific electrodes, one or more of the apertures may comprise tubular structures 196 arranged perpendicularly to the planar structure. Apertures comprising such tubular structures increase the surface area contacting the electrode and thereby increase the support provided to the elongate electrodes. The planar structure may be made from any material with appropriate structural characteristics including metal, polymer, ceramic, or composite materials and may be formed, machined, molded, or produced with other methods. To avoid unwanted electrical interactions with the electrodes, it is preferable that the interface between the electrodes and the planar structure is not electrically conductive. The material and manufacturing method should also be selected to minimize the amount of friction at the interface between the electrodes and the dynamic support member. Due to a number of factors including their low cost, ease of manufacturability, and favorable electrical properties, the electrode support is commonly made of a thermoplastic such as polycarbonate, polystyrene, polypropylene, acrylic, or polyethylene. The specific material should be selected to achieve sufficient rigidity to provide support to the elongate electrodes while retaining sufficient elasticity to prevent fracture of the component under load. Material selection should also consider the intended method of sterilization for the electrode array (e.g., gamma radiation, steam sterilization, ethylene oxide, or e-beam) to ensure that the dynamic support member is compatible. The specific dimensions and design of the support structure depend on the properties of the selected material. However, it is desirable to minimize the dimensions of the support structure so that it does not excessively limit the distance that the electrodes can be deployed or to interfere with other functional properties of the device. Rigid planar structures of 0.5 mm-2 mm thickness are typically sufficient Another embodiment of a dynamic support member is the use of a compression spring with apertures accommodating the electrodes and constraining their lateral movement. The compression spring may be made from metal, polymer, or elastomeric materials, and may be formed, machined, molded, or produced with other methods. At rest, the spring is uncompressed or minimally compressed with the electrodes inserted into the apertures along the spring's length. As the electrodes are deployed, the spring compresses in the direction of deployment, with the apertures accommodating the sliding movement of the electrodes perpendicular to the spring coils. This embodiment is of particular utility when combined with a shield or sheath used to house the penetrating electrodes/needles following removal from the tissue site. In these embodiments, the force imparted to the spring by the forward deployment of the electrodes can be used to deploy a sheath or shield over the electrodes as the device is removed from the tissue.

In the implementation of FIG. 4, the stick shield spring 138 may be used to partially support the electrode support 124, and in particular the radius of the spring may be configured to match (or be just slightly greater than) the radius of the wall 198 of the electrode support 124. In this way, the electrode support 124 may be inserted into the middle of the stick shield spring 138 during use. The electrode support 124 may then slide within the interior of the stick shield 134. By being placed in the center of the spring, the electrode support 124 naturally maintains a position in the center of the spring, which provides a desired "halfway point" for support of the electrodes, roughly halfway between their point of support at the inner cartridge cap 104 and their point of penetration at the tissue interface.

Other spring-based electrode supports are contemplated. For example, a formed compression spring is positioned in the region of the electrodes, to provide adaptive electrode support. Formed compression springs may be shaped and proportioned to conform closely to the relative positions of the electrodes, in order to restrict their lateral motion. An optional biasing element may be positioned in conjunction with a formed compression spring, and may serve to bias the electrodes outward against formed compression spring. Formed compression springs may be made from metal, polymer, or elastomer materials, and may be formed, machined, molded, or produced with other methods. The biasing element may be made from metal, polymer, or elastomer materials, and may be formed, machined, molded, or produced with other methods.

Electrode supports based on other mechanisms are also contemplated, for example telescoping tubes. Telescoping tubes serve to support electrodes during insertion into the subject. The telescoping tubes may be sized to move freely relative to each other, or may be sized to move only when an axial force is applied to them.

Other support structures are contemplated, for example support structures based on movable, flexible, or pivoting support members. Lateral support members may attach to the electrodes at optional hinge features. Lateral support members may be formed integrally with the structure housing the electrodes or may be separate components attached by conventional means (snaps, welding, adhesives, fasteners, etc.).

Another embodiment is the use of a compressible matrix material in which the electrodes are embedded. As the electrodes are deployed, the material compresses in the direction of deployment, providing lateral support along the direction of travel. Examples of compressible matrix materials include cellulose, foamed plastic or rubber polymers such as microcellular plastics, foamed silicone or foamed polychloroprene, or carbon foam matrices. Since the materials are designed to contact the electrodes and/or injection needle (if applicable), the materials should be selected to be compatible with indirect tissue contact.

The above described structures thus support transcutaneous deployment of a plurality of elongate electrodes at tissue depths of up to 60 mm while maintaining the desired spatial relationship among the plurality of electrodes and, in specific embodiments, the orifice of a hypodermic injection needle. Such support members engage the plurality of elongate electrodes during transcutaneous insertion, and constraining deflection of the electrodes in one or more directions perpendicular to their elongate orientation. Another aspect of the present disclosure provides methods and apparatus for utilizing the application of biocompatible lubricious compounds to the surfaces of the plurality of electrodes in order to reduce the applied force required to achieve consistent transcutaneous deployment of a plurality of elongate electrodes to depths of up to 60 mm. In an exemplary embodiment, biocompatible silicone compounds such as Dow Corning 360 Medical Fluid or Dow Corning MDX4-4159 can be applied by conventional spray or dip coating to the plurality of the electrodes comprising the array in order to improve the insertion characteristics of the electrodes. The specific selection of the coating and application conditions, such as coating method and thickness depends on the number, size, composition, and tip configuration of the electrodes as well as the target tissue in which the electrodes are deployed.

Figure 7A:
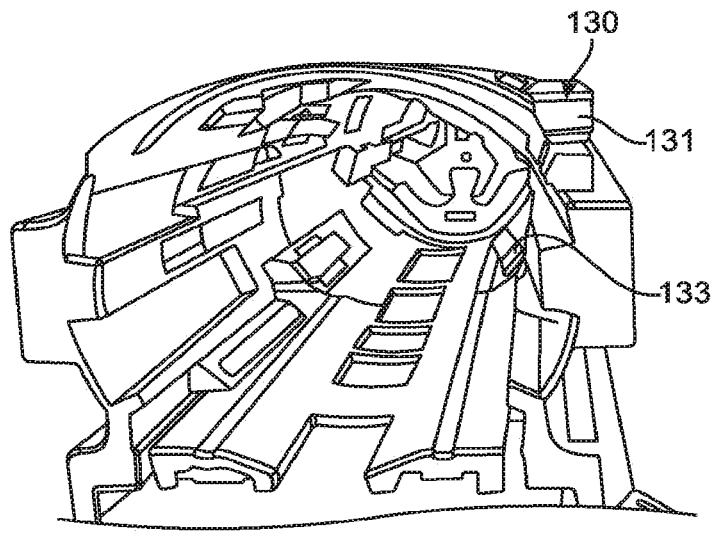
FIGS. 7A-7B show views of aspects of electrodes and/or one or more electrode contact in a device described herein.
Figure 7B:
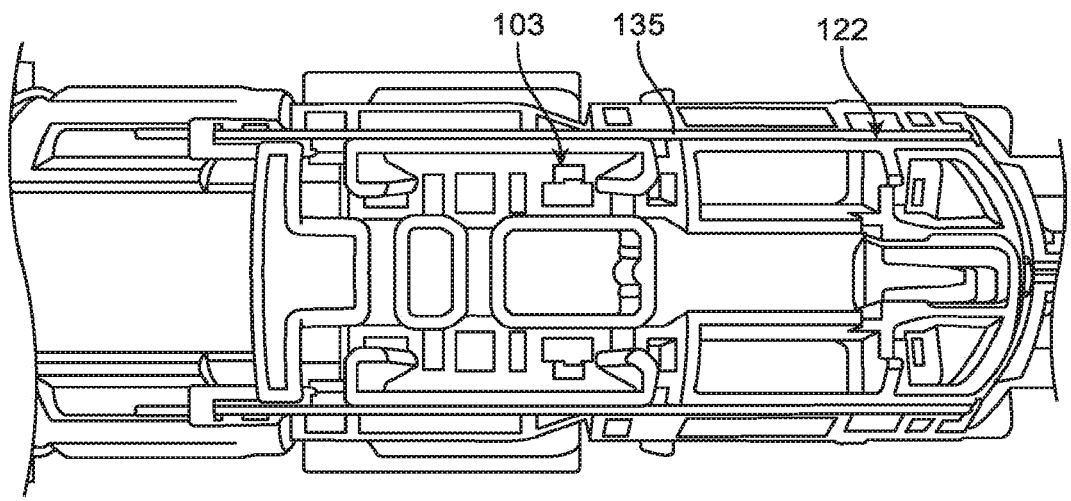
Figure 8A:
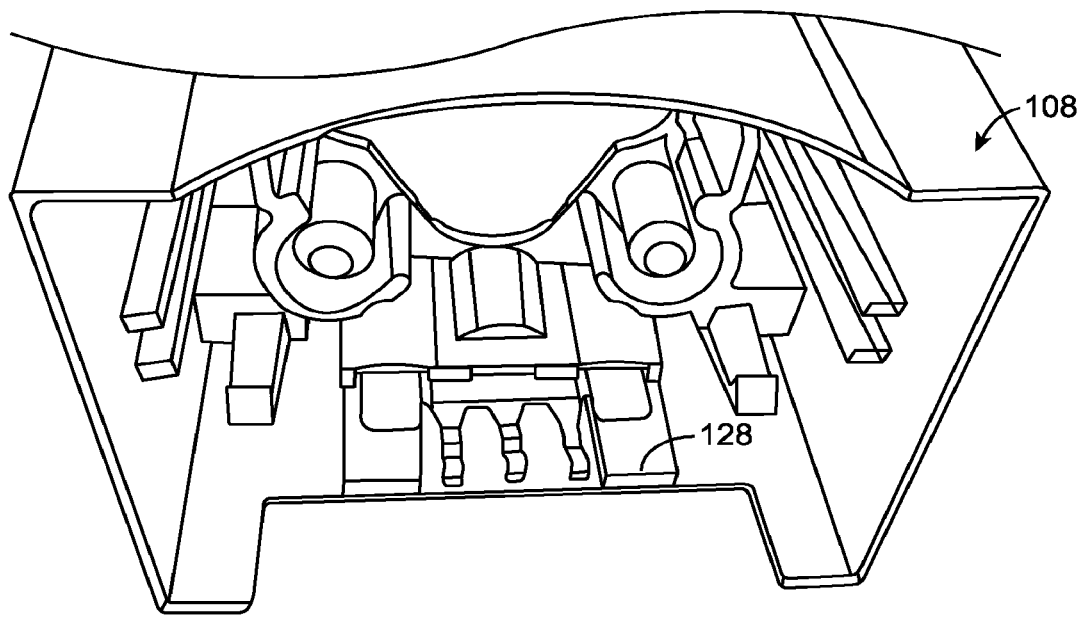
FIGS. 8A-8B show views of aspects of a force contact interlock system in a device described herein.
Figure 8B:
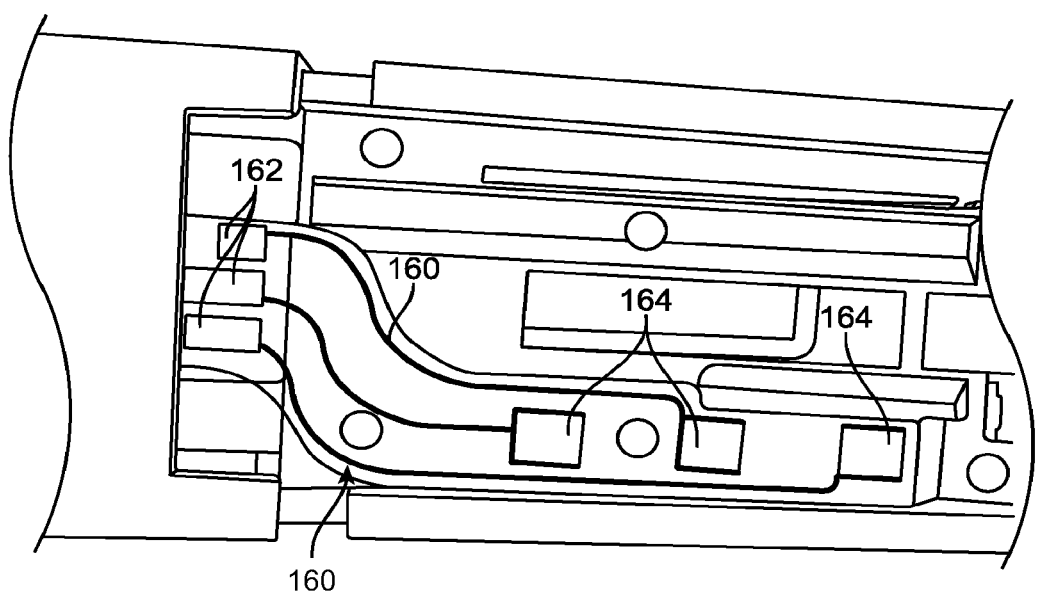

Referring to FIGS. 4 and 7A-7B, a proximal portion 135 of each electrode may be positioned on the exterior of the inner cartridge 103 of the cartridge assembly 100 (FIG. 7B). In this way, when the inner cartridge 103 is slidably disposed within the outer cartridge 102 (FIG. 7A), the proximal portion 135 of each electrode contacts a corresponding electrode contact 130, and in particular an outer cartridge interior portion 133 of the electrode contact 130. The interior portion 133 is configured for power communication with the proximal portion 135 of each electrode. Due to the length of the proximal portions (a single proximal portion 135 pointed-to in FIG. 7A) of the electrodes, and the length of the outer cartridge interior portion 133, the electrical communication can be made at a number of locations along their continuous interface, no matter the longitudinal position of the inner cartridge with respect to the outer cartridge. Each electrode contact 130 further includes an outer cartridge exterior contact 131, configured for power communication with corresponding connections 496 on the applicator 400 (see FIG. 18C). Although not pointed to in the figures, there can a single electrode contact that contacts one of the electrodes, when the electrodes are otherwise electrically coupled, or there can be an electrode contact 130 corresponding to each of the electrodes, and additional corresponding features such as interior portions 133 of the outer cartridge corresponding with each electrode of the apparatus. Thus, despite being referred to in a plural or singular manner, several embodiments are contemplated-aligning with singular and a plural meanings. Each electrode contact 130 is comprised of a conductive material sufficient to convey an electrical signal. In certain embodiments, the design and material selection ensure that the contact provide for adequate engagement to ensure an electrically conductive interface with the corresponding electrode over the range of expected manufacturing variation in electrode and contact position while not inhibiting or interfering with the forward travel of the electrodes 122 mounted on the inner cartridge 103. The design most also permit this engagement to persist when exposed to the expected storage conditions over the labeled shelf life of the product. In a certain embodiment, electrical contacts 130 are made of stamped or formed metal with appropriate temper to facilitate engagement with the electrode and may include coatings such as gold or copper to ensure the integrity of the electrical contacts and avoid corrosion. In addition to ensuring that electrical contact can be maintained with the electrodes at a number of locations along their continuous interface, the incorporation of one or more electrode contact into outer cartridge 102 in this configuration ensures that any wear due to the sliding interaction between the electrodes 122 and the electrode contact 130 occurs within the cartridge 100 designed for single use, thereby allowing for a static interface between the outer cartridge contacts 131 and applicator electrical contacts 496 which minimizes potential mechanical wear on the electrode connections 496 of the applicator designed for multiple uses. This configuration has the benefit of extending the useful functional life of the multi-use applicator.

Remaining portions of the applicator 400 are now described. These portions are generally those that are independent of operation with the cartridge assembly 100. Referring first to FIG. 13A, the applicator 400 includes a handle 402 and a multi-conductor cable 406 designed to carry power and control signals as well as the electrical signals to be applied to the tissue. The cable 406 is generally terminated in a connector with a corresponding connector interface in the controller 700. The applicator 400 further includes a user interface 404, in which aspects of the procedure may be viewed by the user, and in which the user can direct the applicator to perform various functions, in particular, depth selection. The applicator 400 further includes a procedure activation trigger 407, which is used by the subject to initiate the procedure.

Referring in addition to FIG. 13B, the applicator 400 includes a procedure countdown timer 410, which informs the user of the remaining duration of the procedure, and further impliedly indicates to the user that they should not remove the applicator 400 from the subject until such time as the countdown trigger has counted down to zero. A power indicator 418 is provided to indicate a satisfactory and powered connection with the controller 700. A procedure fault indicator 414 is provided to indicate to the user if a fault has occurred, e.g., one of the interlocks described above has not been deactivated. An application placement indicator 412 is provided to inform the user if a proper pressure has been obtained against the tissue of the subject, allowing the procedure to commence.

Figure 14:
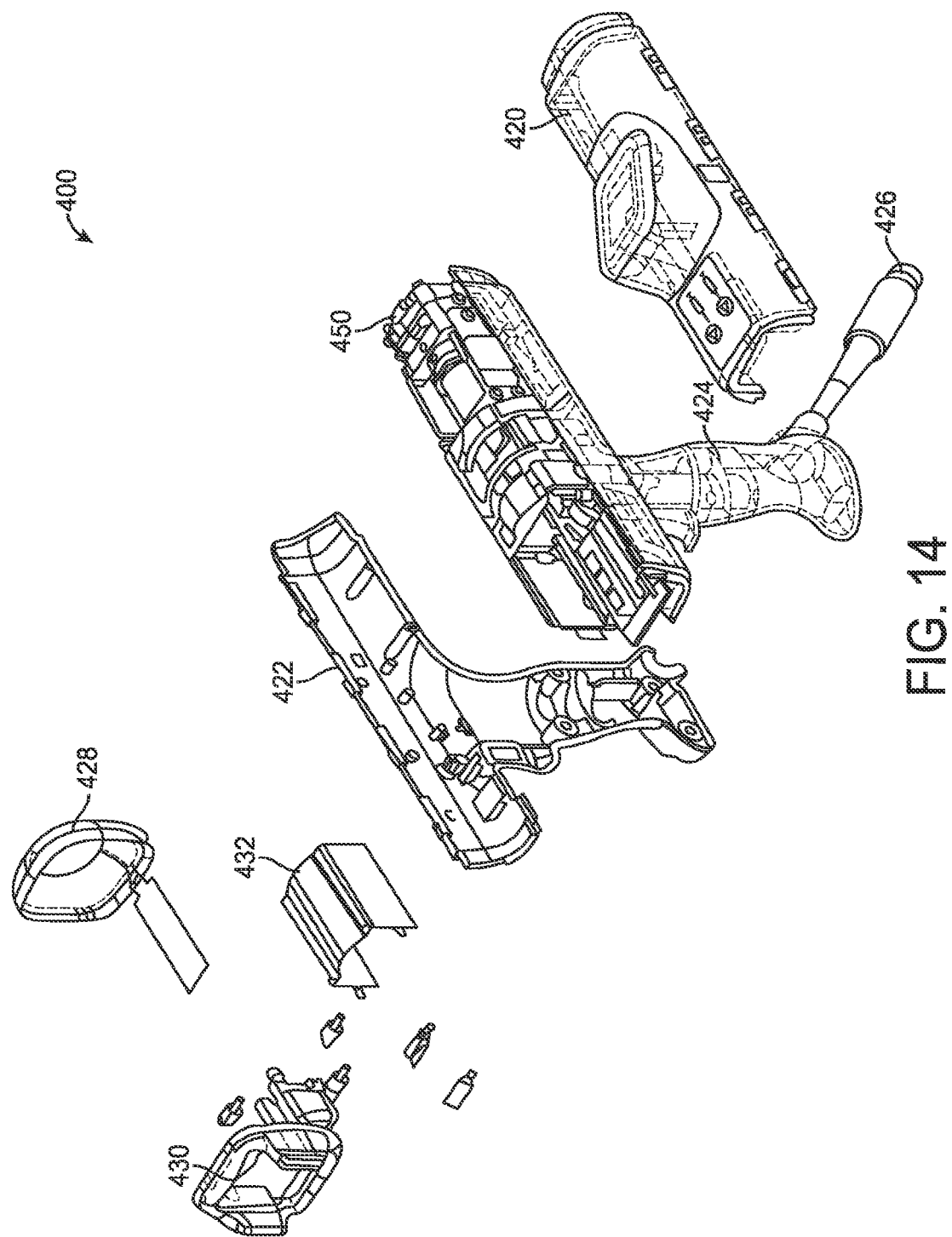
FIG. 14 is an exploded view of an applicator 400 according to present principles.
Figure 15:
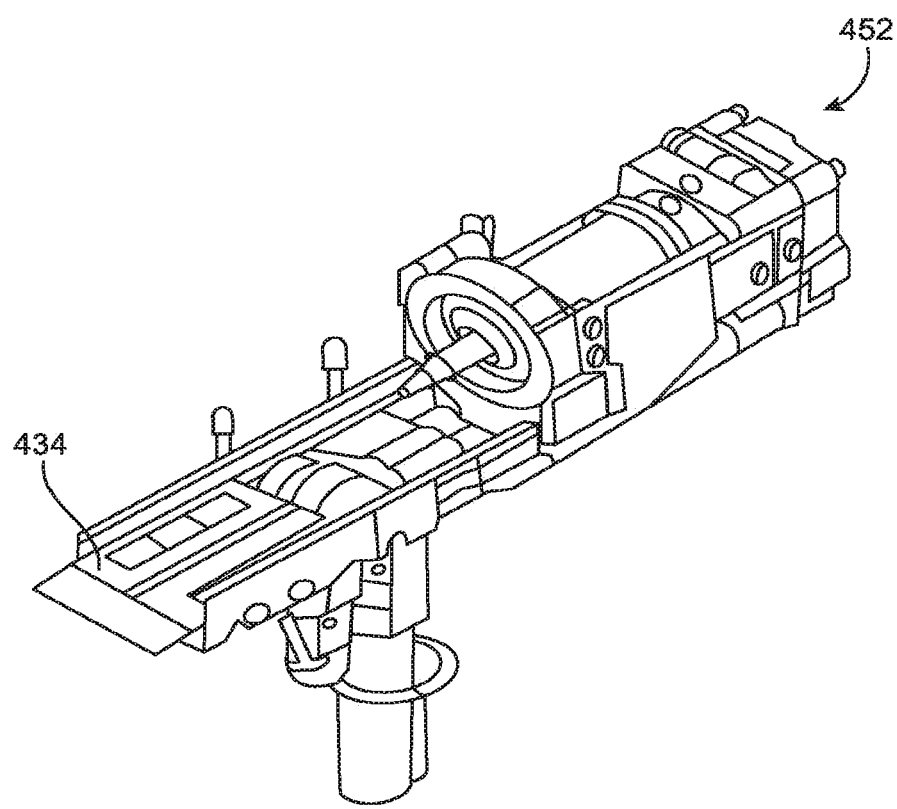
FIG. 15 shows details of a side housing and electroporation electrode connection 496 of an applicator 400 according to present principles.

FIG. 14 indicates a number of structural components of the applicator 400, including a connector 426 (not to scale) for connection to the controller 700, a top housing 420, side housings 422 and 424, and an inner protective shell 432. A front cap 430 is provided, along with an end cap 428. Various electromechanical subassemblies 450 are also provided, several of which have been described above.

FIG. 15A illustrates a more detailed view of the applicator 400, indicating cartridge pressure sensor contacts 434 and subassemblies 452 corresponding to the cartridge loading, electrode insertion, and injection functions as well as the associated sensors.

Figure 16:
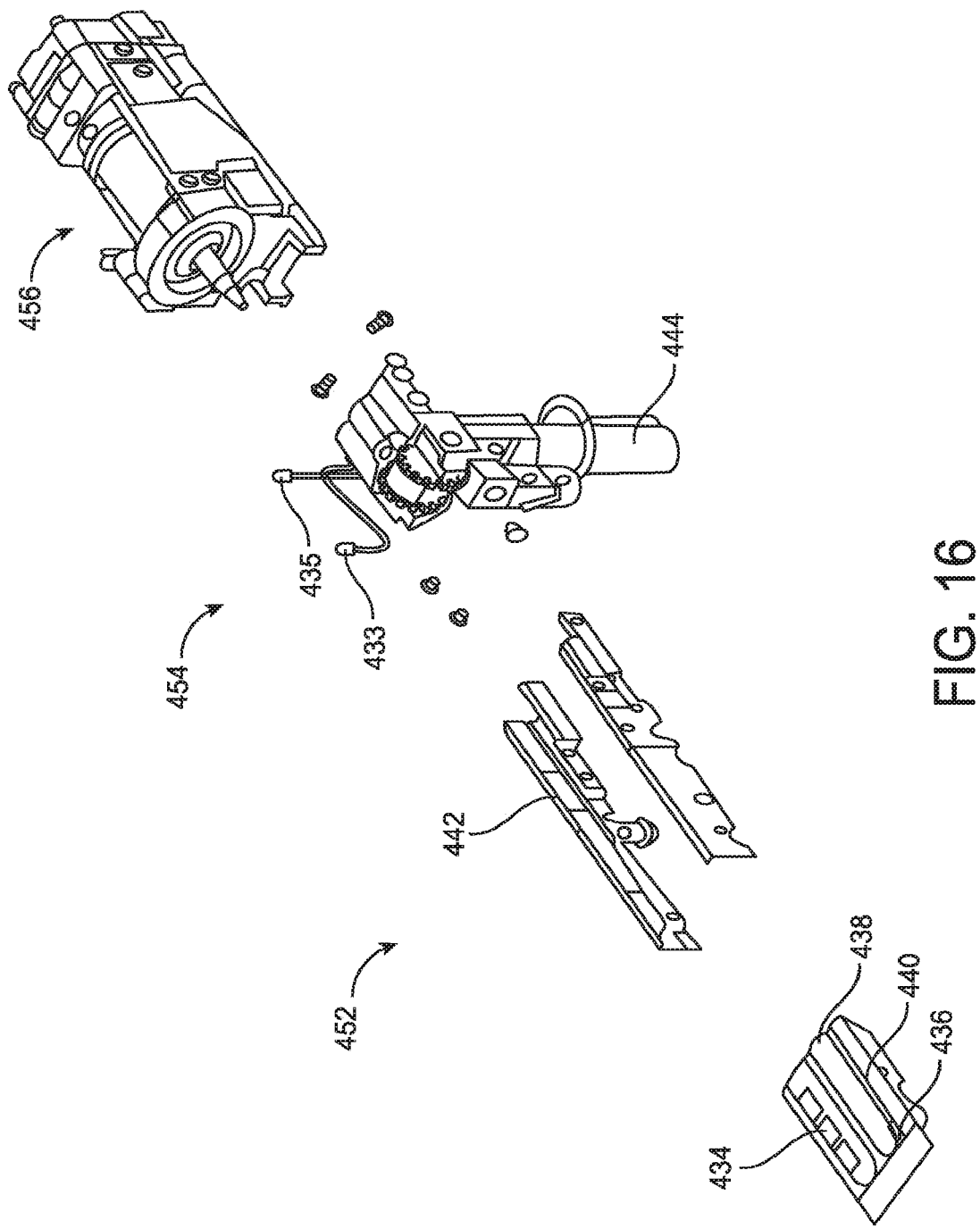
FIG. 16 is an exploded view of an applicator according to present principles, showing a cartridge loading subassembly 456.

FIG. 16 illustrates a more detailed view of the group of subassemblies 452, including the loading drives subassemblies 454 and the cartridge loading subassembly 456. The operation of the subassemblies has been described above.

FIG. 17A illustrates a more detailed view of the loading drive subassembly 454, the general to operation of which has been described above. Here it is noted that the loading is triggered by a flag on the cartridge assembly 100, and that detection of the flag leads to the system being triggered at switch 464. The loading drives subassembly is mounted to the applicator housing using brackets 466 and 468. The action of the motor 444 is transmitted to the pinion gear assembly 448 by the motor drive shaft 462.

FIG. 17B illustrates a more detailed view of the insertion/injection drive assembly 456. Many of these components have been described above. Here it is noted that the operative components are mounted to the applicator housing by a mounting bracket 476. Following insertion of the electrodes 122 and the needle 105, the plunger of the needle 105 is depressed by the injection drive plunger 484, whose action ejects the medicament from the orifice of the needle. The injection drive plunger is driven by an injection drive motor and gear assembly 486.

Generally the injection drive plunger, driven by the injection drive assembly 486, moves forward until such point at which it can no longer move forward, i.e., distally, indicating that it has reached the end of each stroke. This indication is generally given by the current used in the injection drive motor 486 rising substantially, indicating that the reservoir plunger has reached the end of the reservoir and that the injection has been completed. However, in some cases, the number of turns of the motor may be employed to determine how much medicament has been delivered. Such a feature could be used to support metered dosing of medicament or in order to notify the user in cases where the volume of delivery was not within the expected total, e.g., where the full volume of reservoir 101 was expected to be injection, but based on the position of the plunger rod, it was not emptied. These situations may arise where the user failed to hold the applicator 400 against the body of the subject until the procedure was completed, e.g., until the countdown timer had counted down to zero. As noted above, in a mid-procedure timeframe, where the force against the subject is no longer being detected, an impedance check may be performed to determine if the electrodes are still within the subject. If they are not, then it may be presumed that the applicator was prematurely removed, and a signal may be sent to the injection drive motor 486 to cease injection, limiting the amount of medicament ejected outside of the subject.

Referring to FIG. 19, the controller system/assembly 700 can be seen including an electrical field controller/generator 750 and a handle 702 and an applicator cradle 706. The controller may be configured for both table top as well as cart mounted use. In the cart mounted configuration it is the inclusion of a storage bin 704 is favorable. Details of the controller in the cart mounted configuration are shown in FIGS. 20A-20D, including wheel locks to secure the controller assembly against movement in an operational setting, a tray 710 for placing supplies including subject preparation supplies, reservoirs/vials/syringes, and so on. An applicator connector port 708 is illustrated to connect the applicator 400 to the controller assembly 700. A display 712 displays status of an administration procedure, particularly with regard to the IFU attached.

A cartridge eject button 714 is provided to cause ejection of the cartridge assembly 100 from the applicator 400. Menu navigation buttons 716 allow navigation and manipulation of components as seen on the display 712. A mute button 718 is provided to mute alerts or other audible indicators if desired. A power button 722 is provided to power the unit, and the same is activatable if the main power switch 726 (FIG. 20D) has been turned on.

The display also includes a battery indicator 720, which provides an indication of battery level where a battery backup system is provided. Such a battery backup system may be included in the controller/generator 750 to accommodate situations in which power loss prevents a main power source from powering the unit. Such may also be employed as a backup where a procedure has been started under main power, but where a main power loss has been encountered. In this case, logic and control circuitry is implemented to provide for essentially seamless transition from mains to battery power so that the procedure can be finished using the battery backup. It is favorable for the controller to include battery monitoring circuitry that is capable of monitoring whether the battery has sufficient charge to complete the procedure following loss of mains power. In some embodiments, the controller also includes display to notify the user in the event that the current charge status of the battery is not sufficient to complete the procedure in the event of mains power loss.

Referring to FIG. 20D, in which a rear view of the controller 750 is illustrated, the same can be seen to include a USB port 724, a main power switch 726, and a main power input 728.

Figure 21:
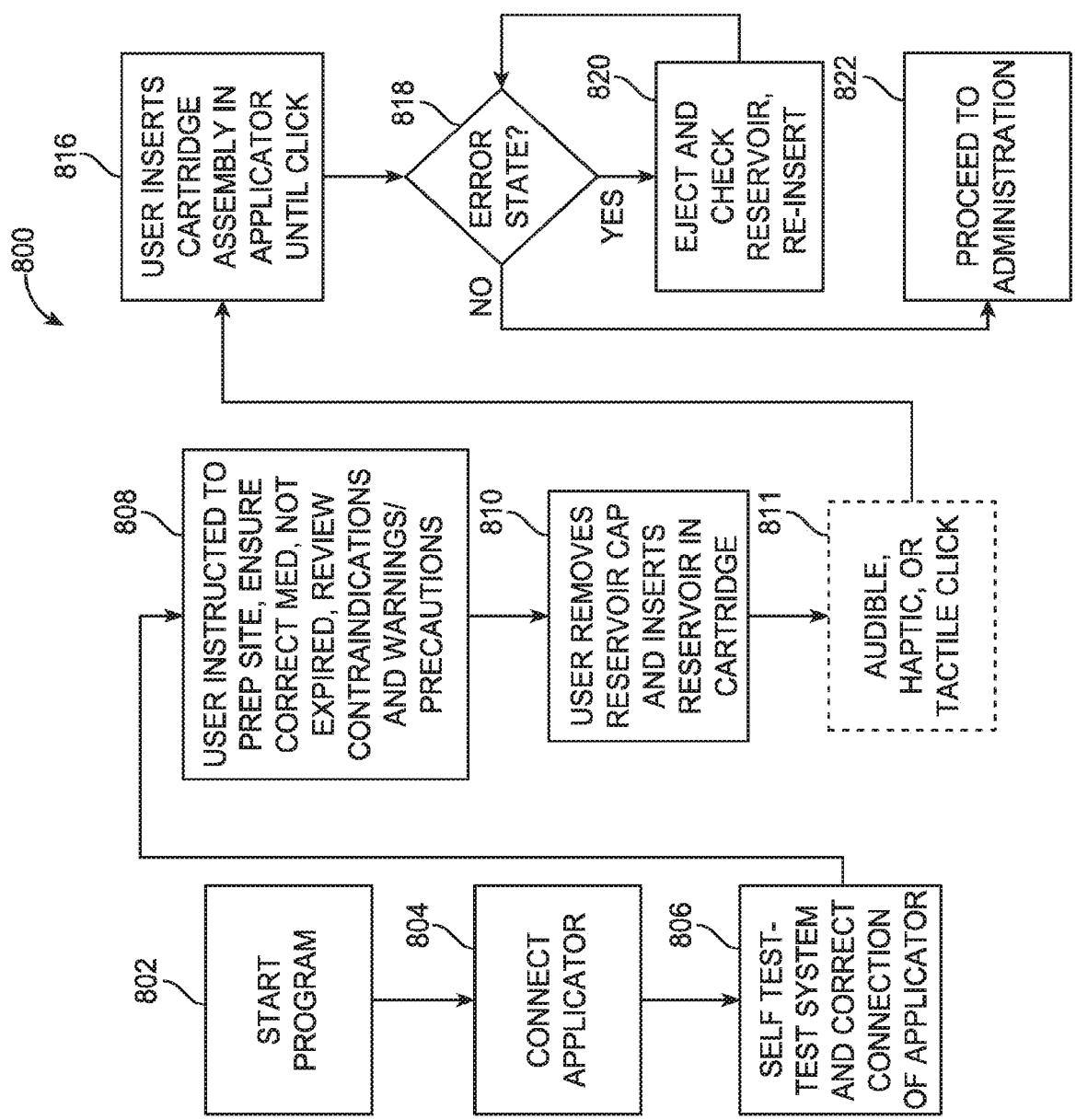
FIG. 21 is a flowchart showing a method of operation according to present principles.

Referring to FIG. 21, in one method of use, as illustrated by the flowchart 800, the controller/generator 750 is powered and its program automatically started (step 802). The applicator is connected (step 804), and an indication or instruction to the user to perform this action may be displayed on the display screen 712, if the applicator has not already been connected. The system may perform a self test (step 806), the self test not only ensuring proper operation of the controller/generator 750 but also ensuring correct connection of the applicator 400 to the controller/generator 750.

The program may cause the display screen to provide instructions to the user on preparation of the site of administration (step 808). This step may include ensuring that the correct medicament agent is being delivered, that the same is not expired, that contraindications have been reviewed, and that warnings/precautions have been followed.

The user then removes the vessel cap and inserts the reservoir 101 in the cartridge assembly 100 (step 810). In some embodiments, the user experiences an audible, tactile, or haptic click (step 811) indicating proper placement of the reservoir in the cartridge assembly.

The user then inserts the cartridge assembly 100 into the applicator 400 (step 816). An error status is then tested for (step 818), e.g., for proper reservoir placement, and if one is detected, the procedure is stopped, an error message is displayed, and the user is instructed to take remedial action. If the error state can be corrected, e.g., the user has inserted the reservoir improperly but not engaged or closed the cartridge breech, then the user may be instructed to remove the cartridge and reinsert the reservoir properly (state 820). In some cases, the cartridge is automatically ejected, and in other cases the user may have to push the "cartridge eject" button to accomplish the same. In other error states, e.g., where the cartridge breech has been closed, the user may be instructed to use a new cartridge.

In any case, once the device set up is completed and a "no error" state has been achieved, the user can proceed to administration of the medicament and electroporation therapy (step 822).

The primary function of the controller is to generate the electrical fields required to achieve the desired delivery of the medicament, to control the operation of the system during set up and use, to monitor the state of the system during set up and use, and to convey the state of the system to the user during set up and use. In some embodiments, the controller is capable of providing recommendations and instructions for use of the device both in the context of user training as well as during resolution of fault conditions during ordinary usage.

The controller system and controller method of operation may be fully implemented utilizing any number of computing devices including microprocessors, microcontrollers, programmable logic controllers. Typically, instructions are laid out on computer readable media, generally non-transitory, and these instructions are sufficient to allow a processor in the computing device to implement the method of the present disclosure. The computer readable medium may be a hard drive or solid state storage having instructions that, when run, are loaded into random access memory. Inputs to the application, e.g., from the plurality of users or from any one user, may be by any number of appropriate computer input devices. For example, users may employ a keypad, keyboard, mouse, touchscreen, joystick, trackpad, other pointing device, or any other such computer input device to input data relevant to the calculations. Data may also be input by way of an inserted memory chip, hard drive, flash drives, flash memory, optical media, magnetic media, or any other type of file—storing medium. The outputs may be delivered to a user by way of a video graphics card or integrated graphics chipset coupled to a display that may be seen by a user. Alternatively, the system may output one or more formats of electronic document or a printer may be employed to output hard copies of the results. Given this teaching, any number of other tangible outputs is also be understood to be contemplated by the present disclosure. For example, outputs may be stored on a memory chip, hard drive, flash drives, flash memory, optical media, magnetic media, or any other type of output. It should also be noted that the present disclosure may be implemented on any number of different types of computing devices, e.g., personal computers, laptop computers, notebook computers, net book computers, handheld computers, personal digital assistants, mobile phones, smart phones, tablet computers, and also on devices specifically designed for these purpose. In one implementation, a user of a smart phone or wi-fi—connected device downloads a copy of the application to their device from a server using a wireless Internet connection. An appropriate authentication procedure and secure transaction process may provide for payment to be made to the seller. The application may download over the mobile connection, or over the WiFi or other wireless network connection. The application may then be run by the user. Such a networked system may provide a suitable computing environment for an implementation in which a plurality of users provide separate inputs to the system and method. In the below system where control of an applicator is contemplated, the plural inputs may allow plural users to input relevant data at the same time.

TABLE OF ELEMENTS

| REF # | PART |
|---|---|
| 100 | Cartridge assembly |
| 101 | Reservoir or vessel (which may be a pre-loaded or non -pre-loaded syringe) |
| 102 | Outer cartridge, aka housing |
| 103 | Inner cartridge |
| 104 | Inner cartridge cap |
| 105 | Needle |
| 106 | Outer cartridge cap |
| 108 | Alignment guide/splay feature |
| 110 | Exterior (safety) cartridge cap |
| 112 | Cartridge breech |
| 114 | Cartridge lock ring |
| 116 | Vessel detection spring |
| 118 | Vessel detection cap |
| 120 | Reservoir or vessel interlock, aka vessel insertion trigger, or vessel interlock |
| 122 | Electrodes |
| 124 | Electrode support |
| 126 | Force contact springs |
| 128 | Force contact pickup |
| 130 | Electrode contact |
| 131 | Exterior Outer cartridge electrode portions for coupling to applicator |
| 132 | Stick shield supports |
| 133 | Interior Outer cartridge electrode portions for coupling to inner cartridge |
| 134 | Stick shield |
| 135 | Proximal Inner cartridge electrode portions for coupling to outer cartridge |
| 137 | Distal Inner cartridge electrode portions for tissue insertion |
| 138 | Stick shield spring |
| 139 | Electrode shoulder or bend |

-continued

TABLE OF ELEMENTS

| REF # | PART |
|---|---|
| 140 | Reservoir or vessel loading port or vessel loading port |
| 142 | Reservoir or vessel containment volume or vessel receiver |
| 144 & 144' | Reservoir or vessel lockout holes (1st or 2nd set) or vessel lockout holes |
| 146 | Optical line of sight |
| 148 | Insertion detector, e.g., emitter/collector IR sensor within applicator |
| 150 | Inner cartridge containment volume |
| 152 | Needle hub |
| 154 | Rack |
| 156 | Egress port |
| 158 | Vessel cap |
| 159 | Plunger stopper |
| 160 | Flexible circuit |
| 162 | First set of pads |
| 164 | second set of pads |
| 166 | Stick Shield nubs |
| 167 | Stick shield holes |
| 168 | Splay feature |
| 170 | Alignment guide hole for stick shield |
| 172 | Initiating flag |
| 174 | Continuing flag |
| 176 | Exterior cartridge cap hooks |
| 178 | Exterior cartridge cap chamfer surfaces |
| 180 | Hook engaging wall of alignment guide/splay shield 108 |
| 182 | Stick shield retaining hooks |
| 184 | First depth retaining wall |
| 186 | Second depth retaining wall |
| 188 | Initial or rest retaining wall |
| 190 | Reminder tab |
| 192 | Electrode support electrode holes |
| 194 | Electrode support needle hole |
| 196 | Electrode support electrode hole support structure |
| 198 | Electrode support wall |
| 400 | Applicator |
| 401 | Applicator cartridge assembly receiving port |
| 402 | Handle |
| 403 | Cartridge assembly receiving volume, which is defined by a housing; or cartridge assembly receiver |
| 404 | User interface |
| 406 | Multi-conductor cable |
| 407 | Trigger |
| 408 | Injection depth selection indicator(s) |
| 409 | Injection depth selection button(s) (could be toggle or other forms in another implementation) |
| 410 | Procedure countdown timer |
| 412 | Application placement indicator |
| 414 | Procedure fault indicator |
| 416 | Procedure complete indicator |
| 418 | Power indicator |
| 420 | top housing |
| 422 | First side housing |
| 424 | Second side housing |
| 426 | Electrical connector |
| 428 | End cap |
| 430 | Front cap |
| 432 | Inner protective shell |
| 433 | Electrical contacts for motor drive 444 |
| 434 | Cartridge force sensor contacts |
| 435 | Connectors for switch |
| 436 | Cartridge loading sensor |
| 438 | Cartridge loaded sensor |
| 440 | Guide or track |
| 442 | Cartridge guide rails |
| 444 | Loading drive motor |
| 446 | Motor trigger connector |
| 448 | Pinion gear assembly |
| 450 | Electromechanical subassemblies |
| 452 | Cartridge loading, electrode insertion, and injection subassemblies |
| 454 | Loading drive subassembly |
| 456 | Cartridge loading subassembly |
| 462 | Motor drive shaft |
| 464 | System trigger switch |
| 466 | gear cover bracket |

-continued

TABLE OF ELEMENTS

| REF # | PART |
|---|---|
| 468 | Mounting bracket |
| 470 | Spring cover/cartridge interface |
| 471 | Spring cover hole |
| 472 | Electrodes/needle insertion spring |
| 476 | Mounting bracket |
| 478 | Insertion mechanism gear drive ring |
| 479 | Insertion gear ring |
| 480 | Flag holder |
| 481 | Insertion mechanism flag |
| 482 | Insertion mechanism drive motor |
| 483 | Insertion mechanism position sensor |
| 484 | Injection drive plunger |
| 486 | Injection drive motor and gearing |
| 488 | Retaining posts (retaining feature) |
| 490 | Channels for first depth |
| 491 | Lock tabs |
| 492 | Channels for second depth |
| 494 | Abutment wall |
| 496 | Applicator electroporation electrode contact |
| 700 | Controller Assembly |
| 702 | Handle |
| 704 | Storage bin |
| 706 | Applicator cradle |
| 708 | Applicator connector port |
| 710 | Tray |
| 712 | Display screen |
| 714 | Eject cartridge button |
| 716 | Menu navigation buttons |
| 718 | Mute button |
| 720 | Battery indicator |
| 722 | Power button |
| 724 | USB port |
| 726 | Main power switch |
| 728 | Main power port |
| 750 | Electrical Field Generator |
| 121 | Finger or Tab as part of Vessel Interlock |
| 169 | Edge for a rib as part of the splay shield |

EXAMPLES

The following example is provided for illustrative purposes only and not to limit the scope of the claims provided herein.

Example 1. Electroporation Mediated Intramuscular Administration of Nucleic Acid Based Biopharmaceuticals with TriGrid Delivery System (TDS-IM) Device The intracellular delivery of nucleic acid sequences in the skeletal muscle of the upper or lower limb can be enhanced with the use of an exemplary device, e.g. TriGrid Delivery System (TDS-IM) model II, as provided herein. In some embodiments, the TDS-IM device is used in conjunction with agents approved for investigational use with the TDS-IM device. In an exemplary embodiment, the approved agent is nucleic acids, i.e., DNA or RNA. In some embodiments, the use of TDS-IM device is restricted to a subject in need thereof.

To start up the system for administration, the main power of the device is connected to the stimulator and the system battery is adequately charged for use. The main power switch is turned on and the front panel power button is depressed. The applicator is connected to the applicator connector. Proper connection of the applicator is confirmed by the illumination of the applicator power indicator. The start screen appears once the system completes all self-checks. The OK button is pressed to proceed with the procedure administration.

To insert a syringe into a TDS-IM cartridge, the syringe cap is removed from the syringe, and the syringe flange is align with the TDS-IM cartridge syringe loading port. The syringe should snap into place and be fully seated in the TDS-IM cartridge. Once the syringe is loaded, the OK button is pressed on the pulse stimulator to continue. The cartridge cap should remain affixed to the cartridge until the cartridge is loaded into the applicator.

To insert the syringe loaded cartridge into the applicator, the cartridge is aligned with the applicator with the cartridge syringe loading port facing upward. When the cartridge is inserted into the applicator, and the cartridge is automatically drawn into its fully loaded position in the applicator. Successful loading of the cartridge is indicated in the stimulator. Once the cartridge is loaded, the applicator is returned to its cradle, and an appropriate injection site on the subject is selected. In some embodiments, the injection site for intramuscular nucleic acid delivery is medial deltoid muscle at approximately three finger widths below the edge of acromion process (shoulder bone). In an exemplary embodiment, the injection depth at medial deltoid is about 0.75"-1.25" (19-30 mm). In some embodiments, the injection site for intramuscular nucleic acid delivery is vastus lateralis muscle (outer thigh) at approximately the midpoint between the hip and the knee. In an exemplary embodiment, the injection depth at vastus lateralis is about 1.0"-1.5" (25-38 mm). Once the injection site is selected, the applicator depth selection button followed by the injection depth selection button corresponding to the injection site/depth are pressed. In some embodiments, the injection depth selection indicator turns to solid illumination, confirming the selected injection depth. In some embodiments, the depth selection button on the right side corresponds to a deeper injection depth. In one embodiment, wherein initially selected injection site is to be changed, the selection button corresponding to the other injection depth is pressed, and the other injection depth is selected when the the select injection depth screen returns.

To start administration of an approved agent via TDS-IM device to the subject, the cartridge cap is removed and discarded. The device is aligned with and firmly pressed against the target injection site. When the device is firmly pressed against the target injection site, all four bars of the applicator placement indicator illuminates, and the procedure countdown timer illuminates with "8" seconds, indicating the time remaining in the administration procedure. The applicator trigger is depressed for the agent to be administered while the pressure is consistently maintained. When the procedure countdown timer reaches "0," the electrical stimulation is delivered. Once the administration procedure is completed, the procedure complete indicator illuminates, and the device can be withdrawn from the injection site. The device may not be withdrawn from the injection site until the procedure is completed or a procedure fault indicator illuminates. In some embodiments, wherein the device detects a problem during the administration procedure, the device aborts the administration procedure and illuminates the procedure fault indicator. In an exemplary embodiment, wherein the device aborts the administration procedure and the device promptly is removed from the subject, the stimulator display of the device provides further instructions.

To eject the cartridge from the applicator after completion of the agent administration to the subject in need thereof, the eject button located on the stimulator is depressed. The applicator automatically advances the cartridge to the position where it can be manually removed from the applicator. Once the cartridge stops moving, the sides of the cartridge as indicated by arrows can be grasped for pulling the cartridge out of the applicator. After the cartridge is removed, completion of the full injection can be verified by inspecting the syringe plunger position. To turn off the device, the applicator is placed in the holster, and the front panel power button is pressed for 5 seconds.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments described herein, or combinations of one or more of these embodiments or aspects described therein may be employed in practicing the present disclosure. It is intended that the following claims define the scope of the present disclosure and that methods and structures within the scope of these claims and their equivalents be covered thereby.

What is claimed is:

1. An apparatus for the controlled delivery of a therapeutic agent to a predetermined tissue site within a subject, the apparatus comprising:
   a cartridge assembly comprising an outer cartridge, an inner cartridge having a vessel receiver located therein, a vessel configured to contain the therapeutic agent, and a needle hub, wherein the vessel receiver is configured to receive the vessel;
   an applicator comprising a cartridge assembly receiver configured to receive the cartridge assembly or a portion thereof, and a vessel insertion detector comprising a sensor that senses the vessel having been loaded in the vessel receiver;
   at least one injection orifice in fluid communication with the therapeutic agent when the therapeutic agent is loaded in the vessel and through which the therapeutic agent is administered;
   a plurality of penetrating electrodes arranged with a predetermined spatial relationship relative to the at least one injection orifice;
   an electrical field generator operatively connected to the plurality of penetrating electrodes;
   a vessel interlock comprising a mechanical interlock comprising a tab extending through the inner cartridge and into the vessel receiver, wherein the tab is moved from a first position to a second position by the vessel after the vessel has been seated within the vessel receiver, whereby when the tab is in the first position, the vessel interlock 1) prevents the vessel from engaging with the needle hub, 2) prevents deployment of the at least one injection orifice, and 3) prevents deployment of the plurality of penetrating electrodes, such that the apparatus is locked out from actuation, and whereby the apparatus is configured to be actuated when the tab is in the second position; and
   a controlled source of energy sufficient to transfer a predetermined amount of the therapeutic agent from the vessel through the at least one injection orifice to the predetermined tissue site within the subject.

2. The apparatus of claim 1, wherein the tab is configured to interact with a corresponding detent feature located in the applicator such that loading of the cartridge assembly into the applicator is physically blocked unless the tab is deflected by a properly loaded vessel.

3. The apparatus of claim 1, wherein the cartridge assembly comprises a splay shield that comprises a rib and an edge configured to engage with skin of the subject and place the apparatus into tension perpendicular to a direction of needle deployment for administration of the therapeutic agent to the predetermined tissue site.

4. The apparatus of claim 1, wherein the cartridge assembly further comprises a stick shield and a stick shield support, wherein the stick shield support abuts the stick shield and prevents the stick shield from moving in a proximal direction in a ratcheting fashion.

5. The apparatus of claim 4, wherein the stick shield comprises a first retaining wall which can prevent proximal movement of the stick shield in case of discharge of said apparatus at a first selected depth and a second retaining wall which can prevent proximal movement of the stick shield after discharge of said apparatus at a second selected depth in the subject.

6. The apparatus of claim 1, wherein the applicator further comprises a loading drive subassembly, wherein the loading drive subassembly comprises a cartridge loading sensor and a cartridge loaded sensor, wherein the cartridge loading sensor detects the cartridge assembly to initiate loading and the cartridge loaded sensor detects the cartridge assembly to cease loading.

7. The apparatus of claim 6, wherein the loading drive subassembly further comprises a connection to a pinion gear assembly, wherein the pinion gear assembly engages a rack on the outer cartridge upon loading the cartridge assembly into the applicator, pulling the cartridge assembly into the cartridge assembly receiver.

8. The apparatus of claim 1, wherein the applicator further comprises a second source of energy comprising:
   a. one or more electromechanical devices comprising at least one solenoid, motor, and/or lead screw;
   b. one or more mechanical components comprising at least one spring and/or related spring device; or
   c. one or more compressed gases;
wherein, the second source of energy provides a driving force for insertion of the penetrating electrodes within the subject before or during transfer of the therapeutic agent.

9. The apparatus of claim 1, wherein the cartridge assembly further comprises one or more electrode contacts operatively connected to a proximal portion of each of the penetrating electrodes, wherein each electrode contact comprises an outer cartridge contact configured for power communication with electrical contacts on the applicator, wherein the electrical contacts on the applicator and each outer cartridge contact have a static interface therebetween.

10. The apparatus of claim 1, wherein the applicator comprises an injection drive plunger, wherein the controlled source of energy is an injection drive motor of the applicator, such that the injection drive motor is configured to move the injection drive plunger so as to enable the transfer of the therapeutic agent.

11. The apparatus of claim 1, further comprising a force detection interlock, wherein the force detection interlock senses a force applied against the subject and prevents administration of the therapeutic agent to the subject when insufficient force is applied.

12. The apparatus of claim 1, further comprising a controller and a force contact circuit wherein a feedback loop exists between said controller and said force contact circuit such that upon insertion of said plurality of penetrating electrodes in said predetermined tissue site, detection of a change in an applied force prompts initiation of a check as to whether the penetrating electrodes remain properly deployed in said predetermined tissue site.

\* \* \* \* \*